(12) United States Patent
Thompson et al.

(10) Patent No.: US 7,858,353 B2
(45) Date of Patent: Dec. 28, 2010

(54) **THERMOPHILIC AND THERMOACIDOPHILIC BIOPOLYMER-DEGRADING GENES AND ENZYMES FROM *ALICYCLOBACILLUS ACIDOCALDARIUS* AND RELATED ORGANISMS, METHODS**

(75) Inventors: David N. Thompson, Idaho Falls, ID (US); William A. Apel, Jackson, WY (US); Vicki S. Thompson, Idaho Falls, ID (US); David W. Reed, Idaho Falls, ID (US); Jeffrey A. Lacey, Idaho Falls, ID (US); Emily D. Henriksen, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 12/322,359

(22) Filed: Jan. 29, 2009

(65) Prior Publication Data

US 2009/0203107 A1 Aug. 13, 2009

Related U.S. Application Data

(60) Provisional application No. 61/025,136, filed on Jan. 31, 2008.

(51) Int. Cl.
| | |
|---|---|
| *C12N 9/42* | (2006.01) |
| *C12N 9/14* | (2006.01) |
| *C12N 9/00* | (2006.01) |
| *C12N 15/00* | (2006.01) |
| *C12P 21/06* | (2006.01) |
| *C12P 19/34* | (2006.01) |
| *C12Q 1/34* | (2006.01) |
| *C08B 37/00* | (2006.01) |
| *D21C 1/00* | (2006.01) |
| *C07H 21/04* | (2006.01) |

(52) U.S. Cl. .................. 435/209; 435/195; 435/183; 435/69.1; 435/320.1; 435/91.1; 435/18; 435/274; 435/277; 536/23.2; 536/23.1; 536/23.7

(58) Field of Classification Search ................ 435/209, 435/195, 183, 69.1, 320.1, 91.1, 18, 274, 435/277; 536/23.2, 23.1, 23.7
See application file for complete search history.

(56) References Cited

U.S. PATENT DOCUMENTS

| | | | |
|---|---|---|---|
| 4,581,333 | A | 4/1986 | Kourilsky et al. |
| 5,098,825 | A | 3/1992 | Tchen et al. |
| 5,882,905 | A | 3/1999 | Saha et al. |
| 5,916,795 | A | 6/1999 | Fukunaga et al. |
| 5,948,667 | A | 9/1999 | Cheng et al. |
| 6,083,733 | A | 7/2000 | Gronberg et al. |
| 6,268,197 | B1 | 7/2001 | Schulein et al. |
| 6,426,211 | B1 | 7/2002 | De Buyl et al. |
| 6,506,585 | B2 | 1/2003 | Danielsen et al. |
| 6,777,212 | B2 | 8/2004 | Asakura et al. |
| 6,833,259 | B2 | 12/2004 | Bhosle et al. |
| 2003/0134395 | A1 | 7/2003 | Shetty |
| 2003/0233675 | A1 | 12/2003 | Cao et al. |
| 2004/0029129 | A1 | 2/2004 | Wang et al. |
| 2005/0112742 | A1 | 5/2005 | Thompson et al. |
| 2006/0211083 | A1 | 9/2006 | Katzen et al. |
| 2007/0082381 | A1 | 4/2007 | Wilting et al. |
| 2007/0134778 | A1 | 6/2007 | Benning et al. |
| 2009/0263859 | A1 | 10/2009 | Thompson et al. |

FOREIGN PATENT DOCUMENTS

| | | |
|---|---|---|
| WO | 81/00577 | 3/1981 |
| WO | 03/068926 A2 | 8/2003 |
| WO | 2005/066339 A2 | 7/2005 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Lucas et al., C4-Dicarboxylate Transporter/Malic Acid Transport Protein [*Alicyclobacillus acidocaldarius* LAA1], GenBank Direct Submission, Accession No. EED06059, Dec. 17, 2008 (Retrieved from the Internet Dec. 15, 2009: <URL:http://www.ncbl.nlm.nlh. gov/protein/218238848), p. 2.

(Continued)

*Primary Examiner*—Ganapathirama Raghu
(74) *Attorney, Agent, or Firm*—TraskBritt

(57) ABSTRACT

Isolated and/or purified polypeptides and nucleic acid sequences encoding polypeptides from *Alicyclobacillus acidocaldarius* are provided. Further provided are methods of at least partially degrading, cleaving, or removing polysaccharides, lignocellulose, cellulose, hemicellulose, lignin, starch, chitin, polyhydroxybutyrate, heteroxylans, glycosides, xylan-, glucan-, galactan- or mannan-decorating groups using isolated and/or purified polypeptides and nucleic acid sequences encoding polypeptides from *Alicyclobacillus acidocaldarius*.

10 Claims, 75 Drawing Sheets

OTHER PUBLICATIONS

PCT International Search Report and Written Opinion of the International Searching Authority for PCT/US09/34701, dated Jan. 12, 2010, 10 pages.

T. Collins et al., "Xylanases, Xylanase Families and Extremophilic Xylanses," FEMS Microbiology Review, 2005, pp. 3-23.

K. Eckert et al., "A Thermoacidophilic Endoglucanase (CelB), etc.," Eur. J. Biochem. 270, 2003, pp. 3593-3602.

Ito et al., "Purification and properties of acid stable xylanases from *Aspergillus kawachii*," Bioscience Biotechnology and Biochemistry 56 (4):547-550, Apr. 1992.

International Preliminary Report on Patentability and Written Opinion of the International Searching Authority for PCT/US06/42566 dated Apr. 23, 2009 (7 pages).

Supplemental European Search Report for EP 06 82 7231, dated Nov. 12, 2009, 6 pages.

Shallom et al., "Microbial hemicellulases," Current Opinion in Microbiology, Current Biology Ltd, GB, vol. 6, No. 3, Jun. 1, 2003, pp. 219-228.

Eckert et al., "Gene cloning, sequencing, and characterization of a family 9 endoglucanase (CelA) with an unusual pattern of activity from the theremoacidophile *Alicyclobacillus acidocaldarius* ATCC27009," Applied Microbiology and Biotechnology, vol. 60, No. 4, Dec. 2002, pp. 428-436.

Olins, P. O., and Lee, S. C., 1993, Recent advances in heterologous gene expression in *E. coli*. Curr. Op. Biotechnology 4: 520-525.

Schäffer, C. et al., 2001, Prokaryotic glycosylation. Proteomics, 1: 248-261.

Schwermann, B. et al., 1994, Purification, properties and structural aspects of a thermoacidophilic alpha-amylase from *Alicyclobacillus acidocaldarius* ATCC 27009, insight into acidostability of proteins. Eur. J. Biochem. 226: 981-991.

Tsao, GT, MR Ladisch, and HR Bungay, 1987. Biomass Refining, In Advanced Biochemical Engineering, Wiley Interscience, N.Y., 79-101.

Urdea, M. S., 1988, Nucleic Acids Research, II: 4937-4957.

Upreti et al., 2003, Bacterial glycoproteins: Functions, biosynthesis and applications. Proteomics, 3: 363-379.

Vieille and Zeikus, 2001, Micro. and Mol. Biol. Rev., vol. 65, No. 1, p. 1-43.

Eckert, Kelvin, "Dissertation, Cloning and Characterization of two glycosidases from the acidothermophile *Alicyclobacillus acidocaldarius* ATCC27009," Berlin, Dec. 18, 1971, 113 pages.

PCT International Search Report and Written Opinion of the International Searching Authority for PCT/US09/35331, dated Feb. 23, 2010, 10 pages.

PCT International Search Report and Written Opinion of the International Searching Authority for PCT/US09/35275, dated Feb. 25, 2010, 13 pages.

GenBank: E17054.1 Direct Submission *Alicyclobacillus acidocaldarius* genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2 &tool=EntrezSystem2.PEntrez.Sequence.Sequence_ResultsPanel. Sequence_RVDocSum], 3 pages.

GenBank: E17054.1 Direct Submission *Alicyclobacillus acidocaldarius* genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2 &tool=EntrezSystem2.PEntrez.Sequence.Sequence_ResultsPanel. Sequence_RVDocSum], 1 page.

Hulsmann et al., "Maltose and maltodextrin transport in the thermoacidophilic gram-positive bacterium *Alicyclobacillus acidocaldarius* is mediated by a high-affinity transport system that includes a maltose binding protein tolerant to low pH," J. Bacteriol. 2000, 182(22):6292-6301.

Jones et al., "Cloning and transcriptional analysis of the *Thermoanaerobacter ethanolicus* strain 39E maltose ABC transport system," Extremophiles 2002, 6:291-299.

Schafer et al., "X-ray Structures of the Maltose-Maltodextrin-binding Protein of the Thermoacidophilic Bacterium *Alicyclobacillus acidocaldarius* Provide Insight into Acid Stability of Proteins," J. Mol. Biol. 2004, 335:261-274.

Scheffel et al., "Functional reconstitution of a maltose ATP-binding cassette transporter from the thermoacidophilic gram-positive bacterium *Alicyclobacillus acidocaldarius*," Biochem Biophy Acta, 2004, 1656(1):57-65.

Schneider, "Import of solutes by ABC transporters—the maltose system. ABC protein: from bacteria to man," Elsevier Science, London 2003, p. 157-185. [Retrieved from the Internet on Jan. 24, 2010; <http://www2.hu-berlin.de/biologie/baktphys/paper/1_ABC/review_chap-09.pdf].

Uniprot Direct submission Q9RHZ5_ALIAC, "Putative maltose transport membrane protein malF," Nov. 13, 2007. [Retrieved from the Internet Jan. 22, 2010: <http://www.uniprot.org/uniprot/Q9RHZ5.txt?version=30?].

Lauro et al., "Isolation and characterization of a new family 42 beta-galactosidase from the thermoacidophilic bacterium *Alicyclobacillus acidocaldarius*: Identification of the active site residues," Biochimica et Biophysica Acta 1784 (2008) 292-301.

Barany, F., 1911, PNAS. USA, 88: 189-193.

Bertoldo et al., 2004, Eng. Life Sci., 4, No. 6.

BLAST Search of Seq. ID. 36, accessed Apr. 22, 2009, 54 pages.

BLAST Search of Seq. ID. 456, accessed Apr. 22, 2009, 48 pages.

BLAST Search of Seq. ID. 458, accessed Apr. 22, 2009, 59 pages.

BLAST Search of Seq. ID. 460, accessed Apr. 22, 2009, 37 pages.

BLAST Search of Seq. ID. 462, accessed Apr. 22, 2009, 35 pages.

BLAST Search of Seq. ID. 464, accessed Apr. 22, 2009, 45 pages.

Borman, S., 2006, Glycosylation Engineering. Chem. Eng. News, 84(36): 13-22.

Buckholz, R. G., 1993, Yeast systems for the expression of heterologous gene products. Curr. Op. Biotechnology 4: 538-542.

Burg, J. L. et al., 1996, Mol. and Cell. Probes, 10: 257-271.

Chu, B. C. F. et al., 1986, NAR, 14: 5591-5603.

Duck, P. et al., 1990, Biotechniques, 9: 142-147.

Edwards, C. P., and Aruffo, A., 1993, Current applications of COS cell based transient expression systems. Curr. Op. Biotechnology 4: 558-563.

Erlich, H.A., J Clin. Immunol., Nov. 1989; 9(6):437-47.

Garrote, G, H Dominguez, and JC Parajo, 2001, Manufacture of xylose-based fermentation media from corncobs by posthydrolysis of autohydrolysis liquors, Appl. Biochem. Biotechnol., 95:195-207.

Guateli, J. C. et al., 1990, PNAS. USA, 87: 1874-1878.

Hamelinck, CN, G van Hooijdonk, and APC Faaij, 2005, Ethanol from lignocellulosic biomass: techno-economic performance in short-, middle-, and long-term, Biomass Bioenergy, 28:384-410.

Huygen, K. et al., 1996, Nature Medicine, 2(8): 893-898.

Jeffries, 1996, Curr. Op. in Biotech., 7:337-342.

Kievitis, T. et al., 1991, J. Virol. Methods, 35: 273-286.

Kohler, G. et al., 1975, Nature, 256(5517): 495497.

Kwoh, D. Y. et al., 1989, PNAS. USA, 86: 1173-1177.

Lavarack et al., "The acid hydrolysis of sugarcane begasse hemicellulose to produce xylose, arabinose, glucose and other products," Biomass and Bioenergy 23 (2002) 367-380.

Liu C, and CE Wyman, 2003, The effect of flow rate of compressed hot water on xylan, lignin, and total mass removal from corn stover, Ind. Eng. Chem. Res., 42:5409-5416.

Luckow, V. A., 1993, Baculovirus systems for the expression of human gene products. Curr. Op. Biotechnology 4: 564-572.

Lynd et al., 2002, Micro. and Mol. Biol. Rev., vol. 66, No. 3, p. 506-577.

Malherbe and Cloete, 2002, Re/View in Environmental Science and Bio/Technology, 1: 105-114.

Matthews, J. A. et al., 1988, Anal. Biochem., 169: 1-25.

Merrifield, R. D., 1966, J. Am. Chem. Soc., 88(21): 5051-5052.

Miele, E. A. et al., 1983, J. Mol. Biol., 171: 281-295.

Mielenz, 2001, Curr. Op. in Micro., 4:324-329.

Neddleman and Wunsch, J. Mol. Biol. 48: 443 (1970).

Olins, P. O., and Lee, S. C., 1993, Recent advances in heterologous gene expression in *E. coli*. Curr. Op. Biotechnology 4: 520-525.

Schäffer, C. et al., 2001, Prokaryotic glycosylation. Proteomics, 1: 248-261.

Walker, G. T. et al., 1992, NAR 20: 1691-1696.

Walker, G. T. et al., 1992, PNAS. USA, 89: 392-396.

International Search Report and Written Opinion of the International Search Authority for PCT/US09/32333, mailed Jun. 19, 2009, 9 pages.

UniProtKB/TrEMBL Q9JRQ1 [online]. Oct. 1, 2000. Available on the internet at <<URL:///http://www.uniprot.org/uniprot/Q9JRQ1>>.

PCT International Search Report and Written Opinion of the International Searching Authority for PCT/US09/00442, dated May 18, 2009, 8 pages.

PCT International Search Report and Written Opinion of the International Search Authority for PCT/US09/35307, dated Jun. 10, 2010, 10 pages.

PCT International Search Report and Written Opinion of the International Search Authority for PCT/US10/25521, dated Jul. 14, 2010, 12 pages.

\* cited by examiner

FIG 1A

| | | |
|---|---|---|
| 16078568 | 1 | MAKPKIGLALGSGGAR |
| 89099582 | 1 | MFDAEVSKFLTIARHESYIKGGMLMRQPVIGLALGSGGAR |
| 124524344 | 1 | MAGRPKIGLALGSGGAR |
| 15615150 | 1 | MGKVHRPKIGLALGSGGAR |
| 121533815 | 1 | MRPKIGLALGSGGLR |
| RAAC00169 | 1 | MPRAREDWRIAMSDKARARDNVKVGVALGSGGAK |

| | | |
|---|---|---|
| 16078568 | 17 | GLAHLGVLSSLHKHQIEVDMIAGSSMGALVGSFYAAGHDV |
| 89099582 | 41 | GFAHLGVIKVLKEEGINVDVIAGSSMGALVGCFYGAGLDI |
| 124524344 | 18 | GFAHIGVLKVFEEEGIPVDMISGSSIGALVAALYGAGRTV |
| 15615150 | 20 | GYAHIGVLKVLEQEKIPIDYLAGSSMGALVASLYGAGHPT |
| 121533815 | 16 | GLAHVGVLRVLEREGIPIDCIAGCSIGALVGALYCAGLDP |
| RAAC00169 | 35 | GFAHIGVLLALAEHGVPVHAIAGSSMGALVAGVYAMGVPP |

| | | |
|---|---|---|
| 16078568 | 57 | ATMKKVAKAFKRRLYADYTVPKLGFLKGDRVRQLVHAYTF |
| 89099582 | 81 | DRLYKLAGAFKRKYYLDFTVPKMGFLAGKKVKELIRLFTH |
| 124524344 | 58 | REMELLSGAFKRKYYLDFKIGKMGLISGKRIEDLIRLLVH |
| 15615150 | 60 | EHLIRFANLFKRKYYLDFTVPKMGFIAGHRVEELIRVLAK |
| 121533815 | 56 | DTIYKLAKHTKRRHWLDFIIPKMGIIAGERVLAMLKLLTQ |
| RAAC00169 | 75 | RVMRALAVNLRRRHWLDFTVPKMGFIQGEKVRTVVATMTR |

| | | |
|---|---|---|
| 16078568 | 97 | GKPIEELQIPLGIVACDLQTGEKIVFRKGSVSDAVRASIS |
| 89099582 | 121 | GKNLEDLDIPVRVVATDLKAGEKVVFSKGPIADAVRASIS |
| 124524344 | 98 | GKKLEELNPPVAVVAANLSNGEKTVFKKGPVQEAVRASIS |
| 15615150 | 100 | KKRVEELDPPVRIVAADLLKGERVILQEGDVAEAVRASIA |
| 121533815 | 96 | QKQFADLRIPLAVVATELTTGQEIVFQEGDVAQAVRASIS |
| RAAC00169 | 115 | QGTFADTAIPLAIVATDLIKRRLVVFRSGLIADAVRASIS |

| | | |
|---|---|---|
| 16078568 | 137 | IPGIFIPQRLDGRLLVDGAVVDRIPVSVVKDMGADIIIAS |
| 89099582 | 161 | IPGIFTPEKLEDRLLVDGGVIDRVPVSVVEEMGADLIIAV |
| 124524344 | 138 | IPGIFVPKKIGGHLFVDGGVVDRVPVSVVKEMGAELLIGV |
| 15615150 | 140 | IPGIFVPKNINDRLLIDGGVIDRVPVSVVKEMGADLTIAV |
| 121533815 | 136 | VPGIFVPHRLNDMLLVDGAVINPTPIDVARRMGANIVIAV |
| RAAC00169 | 155 | IPGVFVPVVRDGAVYVDGGVLERVPVQACWDLGVDLVIAV |

| | | |
|---|---|---|
| 16078568 | 177 | DVSRVRKTETAVHIFDVIMQSMDILQNELVRHQTIAADIM |
| 89099582 | 201 | DVSRVKTSSDITSIFDVIMQSLDIMQMELVSNREIASDIM |
| 124524344 | 178 | DVSVMKKEAEIRHIYDVIMQSIDIMQMELAESRKTEAHVL |
| 15615150 | 180 | DLTIFREELEIRSVYDVILQTMDMMSKELVRVQEIDCTVM |
| 121533815 | 176 | DLAHAGTVCKITNTFDVIIQSIDIMERELFKHRQHYCDVL |
| RAAC00169 | 195 | DVGVTPRGTPPTSAMDVIMQSLELMQDEALRARDRGASLT |

| | | |
|---|---|---|
| 16078568 | 217 | IRPS....LETYSSSSFANIEEMISAGEEATNRMISKIRK |
| 89099582 | 241 | IRPH....VEMYSSRAFTNIEDIIRIGEEEARKQVPRIKE |
| 124524344 | 218 | IRPD....VSMYSSMAFTNAGQIIKIGEEAAKQSVTEIQQ |
| 15615150 | 220 | IRPMNDRYRSLSSSIDFEAVNDLILLGERAAIAKIPEIKD |
| 121533815 | 216 | IRPD....VAHITPSSFETFDECVALGEQAGEAALPKIKA |
| RAAC00169 | 235 | LVPE....VSHIGTAQLQRAAEAIDLGYQAAVAQLDRIWD |

FIG 1B

| | | |
|---|---|---|
| 16078568 | 253 | EIEN.........WEGS |
| 89099582 | 277 | AIQN.........WKGQEDDEEK |
| 124524344 | 254 | LLEK.........WKEPDK |
| 15615150 | 260 | AIAT.........WKETHYETDEKA |
| 121533815 | 252 | LLAEGGQRCITATGENPSRPSDSGG |
| RAAC00169 | 271 | AIDR..........AGAFVS |

FIG 2A

| | | |
|---|---|---|
| 15613871 | 1 | MANTHSPLSRPPVKKRWLHRVILSVCVLAFLGGLSIVGIS |
| RAAC00501 | 1 | MTNAG.........RWVLRIAVGVMVLAILAWLATMAIG |
| 125974699 | 1 | MRITVLTYSRQ..KSHIIRKIILFIVLLALIFSVVVSAVS |
| 5457696 | 1 | MIWTWTILLFLTIIFGFF |
| 14520481 | 1 | MIWTWTILLFLTIIFGFF |
| 40744233 | 1 | MATLSKHHLQP......LGPIHPPRLGSARANEVDAQPIF |

| | | |
|---|---|---|
| 15613871 | 41 | VYVGWNLSHPEREVID...ESPTDYGLLFEDVVFYSEKDE |
| RAAC00501 | 31 | YVVAEKLTHPARKPIS...TSPAAYGLKYESIRFPSRVDH |
| 125974699 | 39 | VIAGWKLIHPKRLNIL...DFSANIVPSYTDVSFKDINDE |
| 5457696 | 19 | AFVGYKMVTPPRRVGK...WTPKDLGFDYEKVEFKSR.DG |
| 14520481 | 19 | AFVGYKMVTPPRRVGK...WTPKDLGFDYEKVEFKSR.DG |
| 40744233 | 35 | IPVHDPLDHEAPAILHSPRDYDAAEARNSAVILVSGAGGG |

| | | |
|---|---|---|
| 15613871 | 78 | VELKGWWIPAQDNGEELGTDRAVVFSHGYRHSRLQGENDI |
| RAAC00501 | 68 | LMLAGWLIPAARP.....TDRIVIEAHGYRQNRVL.DHPA |
| 125974699 | 76 | FELKGWYFNVTGS......SKTVILAHGYGKNRLNFGENT |
| 5457696 | 55 | ITLRGWWIDQGKD.......ETVIVLHGYTASKWN.EVYM |
| 14520481 | 55 | ITLRGWWIDQGKD.......ETVIVLHGYTASKWN.EVYM |
| 40744233 | 75 | VSGPSGIYPSLADKLAILLGVHVVRLDYRVAARTDYCVPD |

| | | |
|---|---|---|
| 15613871 | 118 | LPFAKRLAQEGYHLLLFDYRGSGESGGTYTTIGQYETDDL |
| RAAC00501 | 102 | LPVAKALHDAGFAVLMFDFRDEGESPGSEVTVGDYELRDL |
| 125974699 | 110 | IHLIKSLLDKGYNVLAFDFRNSGESEGNKTTFGVCEKNDL |
| 5457696 | 87 | KPAIEIVANLGYNVLTFDFRAHGESEGSKTTIGDKEILDL |
| 14520481 | 87 | KPAIEIVANLGYNVLTFDFRAHGESEGSKTTIGDKEILDL |
| 40744233 | 115 | IAATMDYLQDNHGSTRFVVVGWSFGGSPCFTIAAQQPDRV |

| | | |
|---|---|---|
| 15613871 | 158 | LSAIAFVKAEKHVEEIAVIG.....WSMGAVSAILATQQS |
| RAAC00501 | 142 | LGAIDYAHKLG.YDEVGLIG.....YSMGASTALEATAAD |
| 125974699 | 150 | LGAIQYVKNKG.SEKIVLMG.....FSTGASACILAAAES |
| 5457696 | 127 | SGAIDWLLSNTNTKKIALIG.....FSMGAMVTIRALAED |
| 14520481 | 127 | SGAIDWLLSNTNTKKIALIG.....FSMGAMVTIRALAED |
| 40744233 | 155 | LGVATVASQTAQTSGVRKLSPRPLLVLHGSDTCLPQRCS |

| | | |
|---|---|---|
| 15613871 | 193 | EDVQIVIADSPF..ANLRQYLSENLSHWSDLPDVPFTWVV |
| RAAC00501 | 176 | PSVDATIADSPF..DDLETYLEQNLSVWTNLPSFPFNGEI |
| 125974699 | 184 | DDVDAVIAESPY..SDLNTYFEQNVNNLTNFPAIPFNKTI |
| 5457696 | 162 | ERVCCGIADSPP..IYIDKTGARGLKYFANLPEFLYPIIK |
| 14520481 | 162 | ERVCCGIADSPP..IYIDKTGARGLKYFANLPEFLYPIIK |
| 40744233 | 195 | ESLYQQYGDDPSGSREIKIFKGDNHGLSRNAPEAEGMLLV |

| | | |
|---|---|---|
| 15613871 | 231 | LQTIPVLIGADIDQVSPVDAVSPIGETKLFLIHGRWD... |
| RAAC00501 | 214 | LWEVKHLFGLDPNAVDPLKQLASAKPRPILLIAGTAD... |
| 125974699 | 222 | TFATFFLADIKPDEASPVKAVQAVSPRPVLLIHSKDD... |
| 5457696 | 200 | PFTKMFSGAKEVNIIDYADKVR....KPLLIIAGGND... |
| 14520481 | 200 | PFTKMFSGAKEVNIIDYADKVR....KPLLIIAGGND... |
| 40744233 | 235 | FAAKALGLEDELTAASVRIAAQDWVGSEGERMKEMAEGHD |

FIG 2B

| | | |
|---|---|---|
| 15613871 | 268 | .......EAIPHRDSEAIFEAADG...QAELWLPENEGHV |
| RAAC00501 | 251 | .......TTIPPSNSEALYDELHRRDPEDTLWLVPGAKHV |
| 125974699 | 259 | .......TKVPVENSRLIYKASNP..YTTTFWETSGADHE |
| 5457696 | 233 | .......PLVKVEEVEEFYKRNKTINPRIEVWIT.DAAHV |
| 14520481 | 233 | .......PLVKVEEVEEFYKRNKTINPRIEVWIT.DAAHV |
| 40744233 | 275 | FEGGEALNHNSITSPQALFDHVEREDRQGGSGLSGIAGSY |

| | | |
|---|---|---|
| 15613871 | 298 | KTINEQSEE...YEERILAFLEKSFTE |
| RAAC00501 | 284 | GAYDVEPKA...YLERVVDFFEAYMPVKVTSS |
| 125974699 | 290 | EIYQANPEE...YVKKVTDFLEKLSQT |
| 5457696 | 265 | RTIVKYKEE...WKRKVGEFL**RANL |
| 14520481 | 265 | RTIVKYKEE...WKRKVGEFL**RANL |
| 40744233 | 315 | ELYSLSHRQRMAHLPTARTYFADAIAPEGFYLVYMTIVRK |

| | | |
|---|---|---|
| 15613871 | | |
| RAAC00501 | | |
| 125974699 | | |
| 5457696 | | |
| 14520481 | | |
| 40744233 | 355 | QKTARMYLKLDL |

FIG 3A

| | | |
|---|---|---|
| RAAC00568 | 1 | MGMIHEQTDFTTSEAIRPDTLISPPDDWAFLGRPSRFDVD |
| 6686567 | | |
| 4586418 | 1 | MLEDTSFAIQPE.QDDKTQETHRIDIGNMHTFS |
| 89098051 | 1 | MNDTSFAIHPG.KSRKIENSDYQEAGDVLAIE |
| 114844717 | 1 | MYQ |

| | | |
|---|---|---|
| RAAC00568 | 41 | HDGWATVQYDAGVMVGVAALDDTVLRVAYCRSPGEWPTST |
| 6686567 | 1 | MVGVAALDDTVLRVAYCRSPGEWPTST |
| 4586418 | 33 | HTEHVFSFHCDTGIVKIRFYREDIVRIAFN.PFGETSLST |
| 89098051 | 32 | ECRNGLKARTETGELRIVFYANEIVRITMN.FFGEADAGT |
| 114844717 | 4 | KTSEGIVVRNEGKKLELRVLGDKIINVFVS.DKEEKRKDT |

| | | |
|---|---|---|
| RAAC00568 | 81 | PAIVEQMSQRHSWRLVQEERRVQLECVAGWQIQINRDDGT |
| 6686567 | 28 | PAIVEQMSQRHSWRLVQEERRVQLECVAGWQIQINRDDGT |
| 4586418 | 72 | SVAVVKEPEKVDASVHETEEEVTLTSAKQTVVLQKRPFRV |
| 89098051 | 71 | SPAVIGGLQEVKLEHYESGDQAEVKTSCLTVKLTKSPLRI |
| 114844717 | 43 | IAIERKEYDIPEFSVRKELESILIETDSLKVKINKNDLSV |

| | | |
|---|---|---|
| RAAC00568 | 121 | WSIRHLGFGTAVEAITWYKRK.KGGALTFASLDNAR.FYG |
| 6686567 | 68 | WSIRHLGFGTAVEAITWYKRK.KGGALTFASLDNAR.FYG |
| 4586418 | 112 | RIYDNHGRLLVAEGKKGMAFTYQGEVCCFKMMDEADHFYG |
| 89098051 | 111 | TVADAEGRVLAGENQKGMGYKHSKEVICFKNMEESDQFYG |
| 114844717 | 83 | SFLDKNENIINEDYNGGVKFS.ETDVRCYKKLREDH.FYG |

| | | |
|---|---|---|
| RAAC00568 | 159 | LGEKPGPLDKRHEAYTMWNSDVYAPHVPEMEALYLSIPFF |
| 6686567 | 106 | LGEKPGPLDKRHEAYTMWNSDVYAPHVPEMEALYLSIPFF |
| 4586418 | 152 | FGEKTGFLDKRGETMTMWNTDVYAPHNPETDPLYQSHPYF |
| 89098051 | 151 | FGEKTGFLNKRGEKLVMWNSDVYAPHNPETDPLYQSIPFF |
| 114844717 | 121 | FGEKAGYLDKKGERLEMWNTDEFMTHNQTTKLLYESYPFF |

| | | |
|---|---|---|
| RAAC00568 | 199 | LRLQDQTAVGIFVDNPGRSRFDFRSRYPDVEIS.TERGGL |
| 6686567 | 146 | LRLQDQTAVGIFVDNPGRSRFDFRSRYPDVEIS.TERGGL |
| 4586418 | 192 | MTVRNGSAHGIFFDNTYKTTFDFQTATDEYCFS.AEGGAI |
| 89098051 | 191 | LTLREGQAHGIFFDNTFRAEFDMR.GDEFYSFS.ADGGQL |
| 114844717 | 161 | IGMNDYHTYGIFLDNSFRSFFDMGQECQEYYYFGAYGGQM |

| | | |
|---|---|---|
| RAAC00568 | 238 | DVYFIFGASLKDVIRRYTKLTGRMPMPPKWALGYHQSRYS |
| 6686567 | 185 | DVYFIFGASLKDVIRRYTKLTGRMPMPPKWALGYHQSRYS |
| 4586418 | 231 | DYYVFAGPTPKDVLEQYTDLTGRMPLPPKWALGYHQSRYS |
| 89098051 | 229 | DYYLMAGPSPKDVIRQYTSLTGRMPLPAKWAIGYHQSRYS |
| 114844717 | 201 | NYYFIYGEDIKEVVENYTYLTGRINLPPLWALGNQQSRYS |

| | | |
|---|---|---|
| RAAC00568 | 278 | YETQSEVLSVAQTFVERDIPVDALYLDIHYMDGYRVFTFD |
| 6686567 | 225 | YETQSEVLSVAQTFVERDIPVDALYLDIHYMDGYRVFTFD |
| 4586418 | 271 | YETEQEVREIAQTFIEKDIPLDVIYLDIHYMNGYRVFTFD |
| 89098051 | 269 | YESQQEVMELAAAFKEKGIPLDSIHLDIHYMDEYRVFTFD |
| 114844717 | 241 | YTPQERVLEIAKTFREKDIPCDVIYLDIDYMEGYRVFTWN |

FIG 3B

| | | |
|---|---|---|
| RAAC00568 | 318 | ERRFPDPARMCDELRKLGVRVVPIVDPGVKQDPEYPVYMD |
| 6686567 | 265 | ERRFPDPARMCDELRKLGVRVVPIVDPGVKQDPEYPVYMD |
| 4586418 | 311 | RNRFPNLKQLIADLKQKGIRVVPIVDPGVKEDPEYVIYQE |
| 89098051 | 309 | RDKFPDPEKMISDLKEMGIHIVPIVDPGVKEDPEYMVYKQ |
| 114844717 | 281 | KDTFKNYKEMLKQLKEMGFKVVTIVDPGVKRDYDYHVYRE |
| | | |
| RAAC00568 | 358 | GLAHNHFCQTAEGQVYLGEVWPGLSAFPDFASEEVRAWWG |
| 6686567 | 305 | GLAHNHFCQTAEGQVYLGEVWPGLSAFPDFASEEVRAWWG |
| 4586418 | 351 | GIRHDYFCKYIEGNVYFGEVWPGKSAFPDFTNKKVRKWWG |
| 89098051 | 349 | GIQEDLFCKYLEGNVYYGDVWPGNSVFPDFTSKKVRDWWG |
| 114844717 | 321 | GIEEDYFVKDKYGITYVGKVWPGEACFPDFLQEEVRYWWG |
| | | |
| RAAC00568 | 398 | KWHRVYTQMGIEGIWNDMNEPAVFNE.TKTMDVNVVHRGD |
| 6686567 | 345 | KWHRVYTQMGIEGIWNDMNEPAVFNE.TKTMDVNVVHRGD |
| 4586418 | 391 | EKHQFYTDLGIEGIWNDMNEPSVFNE.TKTMDVKVIHDND |
| 89098051 | 389 | SLHSYYTELGIEGIWNDMNEPAVFNE.SKTMDLKVMHDND |
| 114844717 | 361 | EKHREFIKDGIDGIWNDMNEPAVFETPTKTMPEDNIHILD |
| | | |
| RAAC00568 | 437 | GRLYTHGEVHNLYGFWMAEATYRGLKAQLAGKRPFVLTRA |
| 6686567 | 384 | GRLYTHGEVHNLYGFWMAEATYRGLKAQLAGKRPFVLTRA |
| 4586418 | 430 | GDPKTHRELHNVYGFMMGEATYKGMKKLLNGKRPFLLTRA |
| 89098051 | 428 | GNPRTHKELHNLYGLLMGKSTYEGMKRNLKGKRPFLLTRA |
| 114844717 | 401 | GEKVLHKEAHNVYANYMAMATRDGLLRIRPNERPFVLTRA |
| | | |
| RAAC00568 | 477 | GYSGIQRYAAVWTGDNRSFWEHMAMAIPMVLNMGMSGIPL |
| 6686567 | 424 | GYSGIQRYAAVWTGDNRSFWEHMAMAIPMVLNMGMSGIPL |
| 4586418 | 470 | GFSGIQRYAAVWTGDNRSFWEHLQMSLPMCMNLGLSGVAF |
| 89098051 | 468 | GYSGVQRYAAVWTGDNRSFWEHLQMSLPMVMNLGVSGIPF |
| 114844717 | 441 | AFSGIQRYAAMWTGDNRSLYEHLLMMMPMLINIGLSGQPF |
| | | |
| RAAC00568 | 517 | GGPDVGGFAHHASGELLARWTQMGAFFPFFRNHSAMGTHR |
| 6686567 | 464 | GGPDVGGFAHHASGELLARWTQMGAFFPFFRNHSAMGTHR |
| 4586418 | 510 | CGPDVGGFAHNTNGELLTRWMQVGAFTPYFRNHCAIGFRR |
| 89098051 | 508 | SGPDVGGFAHDSNGELLARWTQAGAFTPFFRNHSVLGSAR |
| 114844717 | 481 | AGADVGGFEGDCHEELFIRWIEAATFTPFLRVHSAIGTKD |
| | | |
| RAAC00568 | 557 | QEPWAFGPTFEAVIRRAIRLRYRFLPYLYTLAREAHETGL |
| 6686567 | 504 | QEPWAFGPTFEAVIRRAIRLRYRFLPYLYTLAREAHETGL |
| 4586418 | 550 | QEPWAFGEKYERIIKKYIRLRYQWLPHLYTLFAEAHETGA |
| 89098051 | 548 | QEPWAFGEKYEAIIRKYIELRYTWMPHLYSLFAEAHKEGT |
| 114844717 | 521 | QEPWSFGKRCEDISRKYIKMRYEILPYLYDLFYIASQKGY |
| | | |
| RAAC00568 | 597 | PMMRPLVLEYPDDPNTHHVDDQFLVGSDLLVAPILKPGMA |
| 6686567 | 544 | PMMRPLVLEYPDDPNTHHVDDQFLVGSDLLVAPILKPGMA |
| 4586418 | 590 | PVMRPLFFEYPDDENTYNLYDEFLVGANVLIAPIMTPSTT |
| 89098051 | 588 | PVMRPLFLEFPEDEHTWNLSDQFMIGDNVIIAPIMQPGTF |
| 114844717 | 561 | PIMRPLVFEYQEDENTHKIYDEFLLGDNLLVAPIYLPSKE |

FIG 3C

| | | |
|---|---|---|
| RAAC00568 | 637 | HRMVYLPDGEWIDYETRERYQGRQYILTYAPLDRIPLYVR |
| 6686567 | 584 | HRMVYLPDGEWIDYETRERYQGRQYILTYAPLDRIPLYVR |
| 4586418 | 630 | RRVAYFPKGNWVDYWTGEVLEGGQYHLISADLETLPIFIK |
| 89098051 | 628 | HRAVYLPEGMWTDYWTGSTYEGKKHHLIKAPLETLPIFIK |
| 114844717 | 601 | KREVYLPKGIWYDYWTGKEFKGESYYLVDAPIDIIPLFVK |

| | | |
|---|---|---|
| RAAC00568 | 677 | AGSAIPVNLLERSGET...QLGWEIFVDANGRASGRCYED |
| 6686567 | 624 | AGSAIPVNLLERSGET...QLGWEIFVDANGRASGRCYED |
| 4586418 | 670 | QGSAIALGDVKRSTEMPDEHRTVHIYKANGGKATYVLYDD |
| 89098051 | 668 | KGTMAAHGEAGAAGPL.....TLHLYYEEGSECSYTLYED |
| 114844717 | 641 | EGGILLKREPQSFVEE.KEIKEIIVEIYRGEEGHYLHYED |

| | | |
|---|---|---|
| RAAC00568 | 714 | DGETFSYEDGAYCDRVLQALATSEGTLIECHLVQGSGDGG |
| 6686567 | 661 | DGETFSYEDGAYCDRVLQALATSEGTLIECHLVQGSGDGG |
| 4586418 | 710 | DGQTFSYEKGDYLRMYIEVEYG.ENSVHIVTKSEGTYQPS |
| 89098051 | 703 | DGETFAYEEGEYREICFKVKCE.EGTVYLNSAIAGTYEPV |
| 114844717 | 680 | DGKSFDYTKGVYNLFDISFCYKEGRMDIKFDKIHFGYDKG |

| | | |
|---|---|---|
| RAAC00568 | 754 | SLESVVRVFTPDDVREARAQGISFSIHV |
| 6686567 | 701 | SLESVVRVFTPDDVREARAQGISFSIHV |
| 4586418 | 749 | WKLSFAIHHATEQTKVTIDGNEQNAIFDPHQRILLIQSE |
| 89098051 | 742 | WSTVQLAVHSRENVRLKIGSSTLLPEKIEEGRHYFILS |
| 114844717 | 720 | VKKYKFIFKNFGDIKEIKINGEKVGKENCEIEL |

FIG 4A

```
16422318    1  MKISDGNWLIQPGLNLIHPVQVFDVEQHGNEMVIYAAPRD
16504867    1  MKISDGNWLIQPGLNLIHPVQVFDVEQHGNEMVVYAAPRD
16131527    1  MKISDGNWLIQPGLNLIHPLQVFEVEQQDNEMVVYAAPRD
52081844    1  MKFSDGYWLTREGYHINTPKEAYDRMIDQQSLTVYGPVKA
52787233    1  MKFSDGYWLTREGYHINTPKEAYDRMIDQQSLTVYGPVKA
RAAC00594   1  MKFTDGNWLVREGVSIHPGLAVQEWRQEGDGVLFFVACRP 16422318   41  VRERTWQLDTPLFTLRFFSPQEGVIGVRMEHFQGALDNGP
16504867   41  VRERTWQLDTPLFTLRFFSPQEGVIGVRMEHFQGALDNGP
16131527   41  VRERTWQLDTPLFTLRFFSPQEGIVGVRIEHFQGALNNGP
52081844   41  VQKRGDTLDTRMLTVRFSSPLEDMIRVQVFHFQGETPRKP
52787233   41  VQKRGDTLDTRMLTVRFSSPLEDMIRVQVFHFQGETPRKP
RAAC00594  41  VAHRGHMLDGPMLTCRISFPRPGMVRVEQHHFFGRMPRGP 16422318   81  HYPLNVLQDINVEMQNNAEFAELKSGSLSVRVTKGEIWSL
16504867   81  HYPLNVLQDINVEMQNNAEFAELKSGSLSVRVTKGELWSL
16131527   81  HYPLNILQDVKVTIENTERYAEFKSGNLSARVSKGEFWSL
52081844   81  DFQL.HTADVEPVITEHDDALTFQSGSLCVEVSK.NGWGY
52787233   81  DFQL.HTADVEPVITEHDDALTFQSGSLCVEVSK.NGWGY
RAAC00594  81  HFPL.ELKPQPFDAAETEDGVVLRAGEMEVRVRL.SPWSI 16422318  121  DFLRNGVRITGSQLKNNGYVQDTNSGRNYMFERLDLGVGD
16504867  121  DFLRNGVRITGSQLKNNGYVQDTNSGRNYMFERLDLGVGE
16131527  121  DFLRNGERITGSQVKNNGYVQDTNNQRNYMFERLDLGVGE
52081844  119  QFSRDGQSLTASESNSLAYITS.DDGRTFMREQLNIGVGE
52787233  119  QFSRDGQSLTASESNSLAYITS.DDGRTFMREQLNIGVGE
RAAC00594 119  AFYENGRFLTESGPRSTAYVV..DHGRPHMRGQLHLSVGE 16422318  161  TVYGLGERFTALVRNGQTVETWNRDGGTSTEQSYKNIPFY
16504867  161  TVYGLGERFTALVRNGQTVETWNRDGGTSTEQSYKNIPFY
16131527  161  TVYGLGERFTALVRNGQTVETWNRDGGTSTEQAYKNIPFY
52081844  158  LLYGLGERFTAFVKNGQTVDIWNQDGGTSTEQAYKNVPFY
52787233  158  LLYGLGERFTAFVKNGQTVDIWNQDGGTSTEQAYKNVPFY
RAAC00594 157  NVYGLGERFTAFVKNGQSLDIWNRDGGTGSDQAYKNVPFY 16422318  201  ITNRGYGVLVNHPQCVSFEIGSEKVSKVQFSVESEYLEYF
16504867  201  ITNRGYGVLVNHPQCVSFEIGSEKVSKVQFSVESEYLEYF
16131527  201  MTNRGYGVLVNHPQCVSFEVGSEKVSKVQFSVESEYLEYF
52081844  198  LSNKGYGVFVNHPELVSYEIGSEVVSKAQFSVEGESLDYF
52787233  198  LSNKGYGVFVNHPELVSYEIGSEVVSKAQFSVEGESLDYF
RAAC00594 197  LTNRGYGVFVNHPERVWFEIGTEFVSKVQFSVEGEALDYV 16422318  241  VIDGPTPKDVLNRYTQFTGRPALPPAWSFGLWLTTSFTTN
16504867  241  VIDGPTPKDVLNRYTQFTGRPALPPAWSFGLWLTTSFTTN
16131527  241  VIDGPTPKAVLDRYTRFTGRPALPPAWSFGLWLTTSFTTN
52081844  238  VISGAEPKDVLKRYAALTGKPALPPAWSFGLWLSTSFTTD
52787233  238  VISGAEPKDVLKRYAALTGKPALPPAWSFGLWLSTSFTTD
RAAC00594 237  VIGGCHPKGVIERYTALTGRPALPPMWSFGLWLSTSFTTD
```

FIG 4B

| | | |
|---|---|---|
| 16422318 | 281 | YDEATVNSFIDGMAERNLPLHVFHFDCFWMKAFQWCDFEW |
| 16504867 | 281 | YDEATVNRFIDGMAERNLPLHVFHFDCFWMKAFQWCDFEW |
| 16131527 | 281 | YDEATVNSFIDGMAERNLPLHVFHFDCFWMKAFQWCDFEW |
| 52081844 | 278 | YSEETVTRFIDGMTERGIPLSVFHFDCFWMKEFEWCNFEW |
| 52787233 | 278 | YSEETVTRFIDGMTERGIPLSVFHFDCFWMKEFEWCNFEW |
| RAAC00594 | 277 | YDEETVSQFVDGMASRGIPLSVFHFDCFWMKPFEWCNFAW |

| | | |
|---|---|---|
| 16422318 | 321 | DPVTFPDPKGMIRRLKAKGLKVCVWINPYIGQKSPVFQEL |
| 16504867 | 321 | DPVTFPDPKGMIHRLKAKGLKVCVWINPYIGQKSPVFQEL |
| 16131527 | 321 | DPLTFPDPEGMIRRLKAKGLKICVWINPYIGQKSPVFKEL |
| 52081844 | 318 | DERYFKQPEAMLSRLKEKGLKICVWINPYIAQKSKLFQEG |
| 52787233 | 318 | DERYFKQPEAMLSRLKEKGLKICVWINPYIAQKSKLFQEG |
| RAAC00594 | 317 | DTACFPDPAGMLARLKSRGLRICVWINPYIAQKSPLFREA |

| | | |
|---|---|---|
| 16422318 | 361 | KEKGYLLKRPDGSLWQWDKWQPGLAIYDFTNPQACEWYAD |
| 16504867 | 361 | KEKGYLLKRPDGSLWQWDKWQPGLAIYDFTNPQACEWYAD |
| 16131527 | 361 | QEKGYLLKRPDGSLWQWDKWQPGLAIYDFTNPDACKWYAD |
| 52081844 | 358 | KENGYFLKNSRGDVWQWDRWQAGMAIVDFTNEKARDWYCS |
| 52787233 | 358 | KENGYFLKNSRGDVWQWDRWQAGMAIVDFTNEKARDWYCS |
| RAAC00594 | 357 | MERGYLLKRPNGDVWQWDLWQPGMGIVDFTNPDARRWYQS |

| | | |
|---|---|---|
| 16422318 | 401 | KLKGLVEMGVDCFKTDFGERIPTDVQWFDGSDPQKMHNHY |
| 16504867 | 401 | KLKGLVEMGVDCFKTDFGERIPTDVQWFDGSDPQKMHNHY |
| 16131527 | 401 | KLKGLVAMGVDCFKTDFGERIPTDVQWFDGSDPQKMHNHY |
| 52081844 | 398 | KLESLLDMGVDCFKTDFGERIPSDAVYFDGSDPERMHNYY |
| 52787233 | 398 | KLESLLDMGVDCFKTDFGERIPSDAVYFDGSDPERMHNYY |
| RAAC00594 | 397 | HLRRLLDMGVDAFKTDFGERIPTDVVYHDGSDPQKMHNFY |

| | | |
|---|---|---|
| 16422318 | 441 | AYIYNELVWNVLKETVGVEEAVLFARSASVGAQQFPVHWG |
| 16504867 | 441 | AYIYNELVWNVLKETVGVEEAVLFARSASVGAQQFPVHWG |
| 16131527 | 441 | AYIYNELVWNVLKDTVGEEEAVLFARSASVGAQKFPVHWG |
| 52081844 | 438 | SYLYNKTVFDLLRQKRGEREAVVFARSATAGGQQFPVHWG |
| 52787233 | 438 | SYLYNKTVFDLLRQKRGEREAVVFARSATAGGQQFPVHWG |
| RAAC00594 | 437 | SYLYNEAVWEVLRE.RGGGEALVFARSATAGGQRFPVHWG |

| | | |
|---|---|---|
| 16422318 | 481 | GDCYANYESMAESLRGGLSIGLSGFGFWSHDIGGFENTAP |
| 16504867 | 481 | GDCYANYESMAESLRGGLSIGLSGFGFWSHDIGGFENTAP |
| 16131527 | 481 | GDCYANYESMAESLRGGLSIGLSGFGFWSHDIGGFENTAP |
| 52081844 | 478 | GDCFASYDSMAESLRGGLSLSLSGFGFWSHDIGGFESTAT |
| 52787233 | 478 | GDCFASYDSMAESLRGGLSLSLSGFGFWSHDIGGFESTAT |
| RAAC00594 | 476 | GDCRATYESMAETLRGGLSLALSGFGFWSHDIGGFEDTAP |

| | | |
|---|---|---|
| 16422318 | 521 | AHVYKRWCAFGLLSSHSRLHGSKSYRVPWAYDDESCDVVR |
| 16504867 | 521 | AHVYKRWCAFGLLSSHSRLHGSKSYRVPWAYDDESCDVVR |
| 16131527 | 521 | AHVYKRWCAFGLLSSHSRLHGSKSYRVPWAYDDESCDVVR |
| 52081844 | 518 | ADLYKRWTAFGLLSTHSRLHGSESYRVPWLFDEEAADVMR |
| 52787233 | 518 | ADLYKRWTAFGLLSTHSRLHGSESYRVPWLFDEEAADVMR |
| RAAC00594 | 516 | AHLYKRWIAFGLFSSHSRLHGSGSYRVPWLFDEESVDVLR |

FIG 4C

| | | |
|---|---|---|
| 16422318 | 561 | FFTEQKCRMMPYLYREAARANEAGTPMMRAMMLEFPDDPA |
| 16504867 | 561 | FFTEQKCRMMPYLYREAARANEAGTPMMRAMMLEFPDDPA |
| 16131527 | 561 | FFTQLKCRMMPYLYREAARANARGTPMMRAMMMEFPDDPA |
| 52081844 | 558 | YFVKLKHRLMPYLYAAAHEAHAEGIPMMRAMLLEFPGDNT |
| 52787233 | 558 | YFVKLKHRLMPYLYAAAHEAHAEGIPMMRAMLLEFPGDNT |
| RAAC00594 | 556 | HFTRWKLRLMPYLWSCAVEAHRTGVPMLRPMMLEFPDDPT |

| | | |
|---|---|---|
| 16422318 | 601 | CDYLDRQYMLGDAVMVAPVFSEAGDVEFYLPEGRWTHLWR |
| 16504867 | 601 | CDYLDRQYMLGDAVMVAPVFSEAGDVEFYLPEGRWTHLWR |
| 16131527 | 601 | CDYLDRQYMLGDNVMVAPVFTEAGDVQFYLPEGRWTHLWH |
| 52081844 | 598 | CHWLDRQYMLGGRLLVAPVFQEDGAVRYYLPKGTWTHLLT |
| 52787233 | 598 | CHWLDRQYMLGGRLLVAPVFQEDGAVRYYLPKGTWTHLLT |
| RAAC00594 | 596 | CDTLDRQYMLGPSLLVAPVFSETGEVVYYLPEGRWTHLFT |

| | | |
|---|---|---|
| 16422318 | 641 | NDEVQGSRWHKQQHDFLSLPVYVRDNTLLALGNNSQKPDY |
| 16504867 | 641 | NDEVQGSRWHKQQHDFLSLPVYVRDNTLLALGNNSQKPDY |
| 16131527 | 641 | NDELDGSRWHKQQHGFLSLPVYVRDNTLLALGNNDQRPDY |
| 52081844 | 638 | GKETEGGEWKEERYGYMRLPLFVRENTLLPLGQESGRPDY |
| 52787233 | 638 | GKETEGGEWKEERYGYMRLPLFVRENTLLPLGQESGRPDY |
| RAAC00594 | 636 | GETRQGGRWYRERYDFMSLPVFVREGSILAMGAETDRPNQ |

| | | |
|---|---|---|
| 16422318 | 681 | AWHEGTAFQLFHLDDGCEAVCEVPATDGSTIFTLQAKRTG |
| 16504867 | 681 | AWHEGTAFQLFHLDDGCEAVCEVPATDGSTIFTLQAKRTG |
| 16131527 | 681 | VWHEGTAFHLFNLQDGHEAVCEVPAADGSVIFTLKAARTG |
| 52081844 | 678 | DYLDDVTFCLYHLKDGCTAEQTIYNEKG.EAMTLRASRHQ |
| 52787233 | 678 | DYLDDVTFCLYHLKDGCTAEQTIYNEKG.EAMTLRASRHQ |
| RAAC00594 | 676 | PYHREVAIHVYPIRPDHRSACTLFDEQGNELGTWHAFWDG |

| | | |
|---|---|---|
| 16422318 | 721 | NTITVSGEGKARNWTLCLRNITQISGTKC..GSYAGSELG |
| 16504867 | 721 | NTITVSGEGEARNWTLCLRNITQISGTKC..GSYAGSELG |
| 16131527 | 721 | NTITVTGAGEAKNWTLCLRNVVKVNGLQD..GSQAESEQG |
| 52081844 | 717 | NTIAVKTTGVQKNWKLLLRGLSVTSVING...AAEALQEG |
| 52787233 | 717 | NTIAVKTTGVQKNWKLLLRGLSVTSVING...AAEALQEG |
| RAAC00594 | 716 | DHLVLTAQGRSEAWSAVLHGIDDPAKLAAQGAECRVSPEG |

| | | |
|---|---|---|
| 16422318 | 759 | VVVTPQGNEVVITL |
| 16504867 | 759 | VVVTPQGNEVVITL |
| 16131527 | 759 | LVVKPQGNALTITL |
| 52081844 | 754 | TAVQPKEKERDVFIYF |
| 52787233 | 754 | TAVQPKEKERDVFIYF |
| RAAC00594 | 756 | VVISPHHPQEAVRVAGCREQWRAE |

FIG 5A

```
16079924    1    MKKARMIVDKEYKIGEVDKRIYGSFIEHMGRAVYEG
RAAC00602   1    MSNLKARMTIDPAYRLAETDPRIYGSFIEHLGRAVYGG
89095985    1    MTLNAHKAKMLIDKSFRISDIDPRIYGSFIEQLGRAVYGG
15614424    1    MTLTATMVVDKSFKIGEIDKRIYGSFIEHLGRAVYEG
52081375    1    MTVHKAKMTIDKEYKVAEIDKRIYGSFIEHLGRAVYEG
52786751    1    MTVHKAKMTIDKEYKVAEIDKRIYGSFIEHLGRAVYEG 16079924    37   IYEPDHPEADEDGFRKDVQSLIKELQVPIIRYPGGNFLSG
RAAC00602   39   IYDPSHPTADEDGFRQDVIDLVKELNVPIVRYPGGNFVSG
89095985    41   IYELSHSSADEDGFRQDVIELVKELRVPIIRYPGGNMVSA
15614424    38   IYEPGHPDGDEQGFRKDVIRLVQELQVPLVRYPGGNFVSG
52081375    39   IYEPDHPEADESGFRKDVIKLVRELKVPFIRYPGGNFVSG
52786751    39   IYEPDHPEADESGFRKDVIKLVRELKVPFIRYPGGNFVSG 16079924    77   YNWEDGVGPVENRPRRLDLAWQTTETNEVGTNEFLSWPKK
RAAC00602   79   YRWEDGVGPVEQRPVQLDLAWRSLEPNRVGLNEFARWAKK
89095985    81   YNWEDGIGPKELRPKRLDLAWNSLETNEVGTNEFAAWAKK
15614424    78   YNWEDGVGPVSERPKRLDLAWRTTETNEIGTNEFVDWAKK
52081375    79   YNWEDGVGPVEQRPTRLDLAWATTEPNLIGTNEFMDWAKL
52786751    79   YNWEDGVGPVEQRPTRLDLAWATTEPNLIGTNEFMDWAKL 16079924    117  VNTEVNMAVNLGTRGIDAARNLVEYCNHPKGSYWSDLRRS
RAAC00602   119  ANSQVMMAVNLGTRGIEEAKQIVEYCNHPGGSYWSDLRRK
89095985    121  VNAEVMMAVNLGTRGIDAARNLVEYCNHPGGTYWSDLRKE
15614424    118  VGAEVNMAVNLGSRGVDAARNLVEYCNHPSGSYWSDLRIS
52081375    119  VGAEVNMAVNLGTRGIDAARNLVEYCNHPSGSYYSDLRKS
52786751    119  VGAEVNMAVNLGTRGIDAARNLVEYCNHPSGSYYSDLRKS 16079924    157  HGYEQPYGIKTWCLGNEMDGPWQIGHKTADEYGRLAAETA
RAAC00602   159  HGIEQPHGIRVWCLGNEMDGPWQIGHKTADEYGRLAQEAA
89095985    161  HGYTDPHNIKVWCLGNEMDGPWQIGMKTAYEYGRLAAETA
15614424    158  HGYKDPHNIKTWCLGNEMDGPWQIGQKTAEEYGRVAAEAG
52081375    159  HGYKEPHKIKTWCLGNEMDGPWQIGHKTAAEYGRLAAEAA
52786751    159  HGYKEPHKIKTWCLGNEMDGPWQIGHKTAAEYGRLAAEAA 16079924    197  KVMKWVDPSIELVACGSSNSGMPTFIDWEAKVLEHTYEHV
RAAC00602   199  KVMKWVDPSIELVACGSSGKMATFPDWERIVLEHAYDEV
89095985    201  KAMKLVDPSIELVSCGSSGSGMPTFPEWEAETLEHTYEAA
15614424    198  KVMKLVDPSIELVACGSSNSKMATFADWEATVLDHTYDYV
52081375    199  KVMKWTDPSIELVACGSSGSGMPTFIDWETTVLDHTYEHV
52786751    199  KVMKWTDPSIELVACGSSGSGMPTFIDWETTVLDHTYEHV 16079924    237  DYISLHTYYGNRDNNLPNYLARSMDLHFIKSVAATCDYV
RAAC00602   239  DYLSLHTYYGNRDGDLANFLACSLDMDAFIRAVVATCDFV
89095985    241  DYISLHQYYGNRDNDSANYLASTLDMDSFIKTVTAACDYM
15614424    238  DYISLHTYYGNRDDDLANYLAQSMDMDEFIRSVIAIADYV
52081375    239  EYISLHSYYGNRDNDLPNYLARSLDMDHFIKTVISVCDYM
52786751    239  EYISLHSYYGNRDNDLPNYLARSLDMDHFIKTVISVCDYM
```

FIG 5B

| | | |
|---|---|---|
| 16079924 | 277 | KAKTRSKKTINLSLDEWNVWYHSNEADKKVEPWITARPIL |
| RAAC00602 | 279 | RAKKRSNKTIYLSFDEWNVWFHSNEADKQVEPWQVGPPLL |
| 89095985 | 281 | KAKKRSKKTMNLSFDEWNVWFHSNDQDKAIEPWSLSPPLL |
| 15614424 | 278 | KAKKRSKKTIHLSFDEWNVWFHSNEADRQITPWSVAPPLL |
| 52081375 | 279 | KAKKKSKKTIHLSYDEWNVWYHSNEKDKEAERWAKAPHLL |
| 52786751 | 279 | KAKKKSKKTIHLSYDEWNVWYHSNEKDKEAERWAKAPHLL |
| | | |
| 16079924 | 317 | EDIYNFEDALLVGSLLITMLQHADRVKIACLAQLVNVIAP |
| RAAC00602 | 319 | EDVYTMEDALVVGCMLITLLKHADRVRIACLAQLVNVIAP |
| 89095985 | 321 | EDIYTFEDALLVGSMLNTLLKHSDRVKIACMAQLVNVIAP |
| 15614424 | 318 | EDIYTFEDALLVGSMLITLLKHADRVKIACLAQLVNVIAP |
| 52081375 | 319 | EDIYNFEDALLVGCMLITMLKHADRVKIACLAQLVNVIAP |
| 52786751 | 319 | EDIYNFEDALLVGCMLITMLKHADRVKIACLAQLVNVIAP |
| | | |
| 16079924 | 357 | IMTEKGGEAWRQPIFYPYMHASVYGRGESLKPLISSPKYD |
| RAAC00602 | 359 | IMTENGGPSWRQTIFYPFAHASNLAHGVVLYAPVESPKYD |
| 89095985 | 361 | IMTETGGGIWKQSIFYPFYYTSVYGRGTALHSIVDSPKYD |
| 15614424 | 358 | IMTEKGGPAWKQTIFYPYMHASVYGRGVALQAQISSPKYD |
| 52081375 | 359 | IMTDKGGEAWRQTIFYPFMHASVYGRGTVLQTAVSSPKYD |
| 52786751 | 359 | IMTDKGGEAWRQTIFYPFMHASVYGRGTVLQTAVSSPKYD |
| | | |
| 16079924 | 397 | CSDFTDVPYVDAAVVYSEEEETLTIFAVNKAEDQ.METEI |
| RAAC00602 | 399 | SKDFTDVPYLEAVPVWNEAAGEMVLLAVNRAEEP.LALDV |
| 89095985 | 401 | SKDFTDVPFLDQSVVYNEESEELVIFAVNRSLDTQLLVDV |
| 15614424 | 398 | SKDFTDVPYLDAAVVHLEEAEEVTIFAVNKHQTESLNLQC |
| 52081375 | 399 | AKDFTDVPYLESVSVFNEEAEELTVFAVNRATDAGLEMEA |
| 52786751 | 399 | AKDFTDVPYLESVSVFNEEAEELTVFAVNRATDAGLEMEA |
| | | |
| 16079924 | 436 | SLRGFESYQIAEHIVLEHQDIKATNQHNRKN.VVPHSNGS |
| RAAC00602 | 438 | DLRGFPNARSEEHIVLTHPNMKAVNTKERPNEVVPQKRSI |
| 89095985 | 441 | DIRSFEGYKLAEQIVLKNENPKAVNSINDEQ.VKPEKGND |
| 15614424 | 438 | DMRSFEGYHVLEHIVLEHENMKATNQ.GREQ.VTPHHNGD |
| 52081375 | 439 | DMRSFEGYSVSEHIVLEHEDHKATNEKDRNN.VVPHSGGD |
| 52786751 | 439 | DMRSFEGYSVSEHIVLEHEDHKATNEKDRNN.VVPHSGGD |
| | | |
| 16079924 | 475 | SSVSENGLTAHFTPLSWNVIRLKKQS |
| RAAC00602 | 478 | GAVDAGRLAVELPALSWNVIRIRV |
| 89095985 | 480 | SYIENGTLTAVLPKMSWNMFRLKKLEV |
| 15614424 | 476 | SAIDQGRLTANLAKLSWNVIRLGKK |
| 52081375 | 478 | AKVCDGRLTAHLPKLSWNVIRMKKQ |
| 52786751 | 478 | AKVCDGRLTAHLPKLSWNVIRMKKQ |

FIG 6A

| | | |
|---|---|---|
| 15893601 | 1 | MHRKFLTALIALG. |
| 15893600 | 1 | MYSLFLWASVKIFTMESRGRYVVHKRILSTVVAFG. |
| 15896196 | 1 | MKKLFTNLLLLCSIVFLGALLNGHNVQASDSFTYPSAYGW |
| 116513351 | 1 | MKKKNLLMTTLATLSASG. |
| RAAC00798 | 1 | MPGAG. |

| | | |
|---|---|---|
| 15893601 | 14 | ......................................... |
| 15893600 | 36 | ......................................... |
| 15896196 | 41 | WSVDNGYDVNNVNSRMVSGDFNGDGKADVATFYDYGNGAS |
| 116513351 | 19 | ......................................... |
| RAAC00798 | 6 | ......................................... |

| | | |
|---|---|---|
| 15893601 | 14 | ...ITVSCSGNIVFASP..........LQDQYNQSQQQY |
| 15893600 | 36 | ...IVASMGSTSVFAAP..........LQD....AQSKY |
| 15896196 | 81 | RIHVFTSNGSSFDYASAYGWWNTPSGYDPKRITAVVAGDF |
| 116513351 | 19 | ...ALLTTGASALADSY...............TVVKNDTL |
| RAAC00798 | 6 | .......IGRDRRMGSG.................INCDGCF |

| | | |
|---|---|---|
| 15893601 | 40 | QNALKSVQDIENKIEALDNQIGELNNS.....INDTDKRI |
| 15893600 | 58 | DASHKNVQNLEEDIQKMDNQIETIMSQ.....RDSVDKKI |
| 15896196 | 121 | NGDHKDDIAVIYNYGNSETRIHVFISTGSSFSYTDCNGWW |
| 116513351 | 41 | WGLSKKYGVSVSDLKKANGVSGHLIYVG........QKLQ |
| RAAC00798 | 23 | FSGFIYIKESPRPPRNRN..................... |

| | | |
|---|---|---|
| 15893601 | 75 | NESKQNMAITQGKID.....QAKQNITNQQEIYG..ERLR |
| 15893600 | 93 | TQSQQNINQAQNDIA.....VSKENIREEKDKFA..DRVR |
| 15896196 | 161 | NATGYDAGRITGAVAGDFNGDGKSDIATMYDYGGGETRIH |
| 116513351 | 73 | IPTKSTKATKTAKTS.....TSTSTVDTTSTTHTVVKGDT |
| RAAC00798 | 41 | LSKTFDFERMESMRR.....PSAWMFTTLTLSFAALGHAT |

| | | |
|---|---|---|
| 15893601 | 108 | AMYVNG...TTAQYIGV.................ILESQS |
| 15893600 | 126 | ALYISG...STQSYVDI.................LLKSKS |
| 15896196 | 201 | VFTSTG...SSFTYTGANGWWNSTGYDSNRVKGRVVAGDF |
| 116513351 | 108 | LWSLAK...KYGVSVSA.................LMKANN |
| RAAC00798 | 76 | VLAATEQQPATYTVR......................... |

| | | |
|---|---|---|
| 15893601 | 128 | FSDLISRLDAVKDVINYDKGIINNFKT.............. |
| 15893600 | 146 | FSDMISRIDAIKQISDYDQKLVSNLKD.............. |
| 15896196 | 238 | NGDGKTDIAAMYDYGGSESRIHVFLSTGDSFKYTGANGWW |
| 116513351 | 128 | LSSSTILIGQSLNLRAGMTTYGVNGVT.............. |
| RAAC00798 | 91 | QGDTLYRIAEADHLPLTALELANPQLS.............. |

| | | |
|---|---|---|
| 15893601 | 155 | QKQEVENQQKILADQNSKLVALQNENHKKLDDLNNKKNTQ |
| 15893600 | 173 | SQGRIEAKKDKIVSEKQQLEALNKENDTKLKQLNDEKSKQ |
| 15896196 | 278 | STTGYDANKVTGRLVAGDFNGDGKADIAAMYDYGNAETRI |
| 116513351 | 155 | TGSSSTAASANTASSTSTTASSQAPKDKKTATKAKSTTTN |
| RAAC00798 | 118 | .....NPNEIAAGQKVALPTAYTVQPGDTVYLIAKAHHLT |

FIG 6B

| | | |
|---|---|---|
| 15893601 | 195 | NSLIVAAKDEEAKHTNEMQQIQKAMDDEKKK..IEALN.V |
| 15893600 | 213 | NVLIAQAKADESKNAAEVKAEKDAEKAAAQARLVAAANTA |
| 15896196 | 318 | HVLTSNGDSFTYTGANGWWNTTGYDANRVTGRVVAGDFNG |
| 116513351 | 195 | TSSNSNTSTSANTQSQSTASNSSASTTTNTNTVASNANTT |
| RAAC00798 | 153 | ISAILQANPGIHPLDLIVGQTLYLPIPASNSTASAPPNTS |
| | | |
| 15893601 | 232 | STNIQLKPVSKTTS...QNTTIQSSSTN.....GLAVVKY |
| 15893600 | 253 | ASSAPAKAVAKAQAPIPRGVSHSSFAGS.....GNDVVSF |
| 15896196 | 358 | DHKADIAAFYDYGSSASRIHVFTSNADSPESSKGAELVAY |
| 116513351 | 235 | SSTNTAASSSQAVSQAPTASTATTTASAS....ASAITSY |
| RAAC00798 | 193 | GTAASAGQPTSTQTQVSRAQLR............QEILTY |
| | | |
| 15893601 | 264 | AETFLNTPYVWGGNKPG.GFDCSGLVQYVYAHFGINLPRT |
| 15893600 | 288 | AESFSGLPYIWGAEDPSRGFDCSGLVQYVYGHFGVSLGRT |
| 15896196 | 398 | AESFLGVPYVWGGADPS.GFDCSGLVQYCYEHFGVDLPRT |
| 116513351 | 271 | ALTFLGVPYVWGGTTPS.GFDCSGLVQYVYSHFGINLGRT |
| RAAC00798 | 221 | AKSFLGTPYCWGGDSPKTGFDCSGFVEYVFGHFGIQLPRE |
| | | |
| 15893601 | 303 | TYEQVNQGNPVTGNNLQPGDLLFFEPGSN.......GPEH |
| 15893600 | 328 | TYEQVNQGTTVT..ALQPGDLLFFGPAS........APYH |
| 15896196 | 437 | TYDQVNCGTTVT.DDLQPGDLLFFGSAT........SPTH |
| 116513351 | 310 | TYTQQYAGTKISVASAQAGDLYFWGSYG........SAYH |
| RAAC00798 | 261 | SHDQATVGTPVSPSNLQPGDLLFFTDTDSYASLYPNHVTH |
| | | |
| 15893601 | 336 | VGIYVGDGNFIEAP..HTGANVRFSP........LRSYCA |
| 15893600 | 358 | VAIYAGNNEMVEAP..RTGENVRKTA........VRGYSI |
| 15896196 | 468 | VAIYAGNSKMVEAP..HTGANVRLVD........IRSYFI |
| 116513351 | 342 | VAIALGGGQYVMAP..APGQNVMTGS........VSSYTP |
| RAAC00798 | 301 | VGIYTGNGAMIESSSAHNGEGVVIVQNVFQNPYYVSHFYG |
| | | |
| 15893601 | 366 | ARRIVN |
| 15893600 | 388 | AKRVR |
| 15896196 | 498 | AKRIFN |
| 116513351 | 372 | SFAVRVLG |
| RAAC00798 | 341 | ARDVIGP |

FIG 7A

| | | |
|---|---|---|
| 52081816 | 1 | MKDCLMINPQDNVGIALRELQTGETV |
| 52787203 | 1 | MKDCLMINPQDNVGIALRELQTGETV |
| 15893984 | 1 | MKNVIKINEKDNVVVALNDLNKGDVI |
| 121533397 | 1 | MALLKLHERDNVAVALRDIRQGETL |
| 15613053 | 1 | MNEKFAYIHEKDNVIIALSPLEQGEVL |
| RAAC01076 | 1 | MHEVNRRQRRRFRVAPKVLHLSPVDDVVVALEPLDVGEVV |

| | | |
|---|---|---|
| 52081816 | 27 | TVGERTIVIKEPILKGHKFALKDIAENENVIKYGFPIGHA |
| 52787203 | 27 | TVGERTIVIKEPILKGHKFALKDIAENENVIKYGFPIGHA |
| 15893984 | 27 | EIDGKVITAEEPVKKGHKIAITDIQKNSNIYKYGFPIGHA |
| 121533397 | 26 | AADNATVTAREDIPKGHKIALCDLQPGEHVIKYGFPIGHA |
| 15613053 | 28 | NVNGLPITLSESIPRGHKVAIVTIEQGEDVIKYGFPIGKA |
| RAAC01076 | 41 | ETPFGQVSARAPIALGHKLAVKPVKCGEAVHKYGFPIGVA |

| | | |
|---|---|---|
| 52081816 | 67 | TEMIQTGEWVHTKNVKTNLGGVEEYSYKPKFTENRYQKEP |
| 52787203 | 67 | TEMIQTGEWVHTKNVKTNLGGVEEYSYKPKFTENRYQKEP |
| 15893984 | 67 | LEEIKKGQWVHTHNIKTNLDGIKDYEYNKQTFENPFKNEN |
| 121533397 | 66 | TSSVAAGQWLHSHNVRTNLGEILAYEYKPEPPAVSPVPCR |
| 15613053 | 68 | TTTIQPGAWVHSQNMKTKLEGVQEYDYTPSTPSFRKQVEK |
| RAAC01076 | 81 | TQDIEPGEWVHTHNLRTALSERGSYVYRPHGSPALVLDDG |

| | | |
|---|---|---|
| 52081816 | 107 | L.TFKGFKRKDGKTGIRNELWIVPTVGCVNGIAELIIKEF |
| 52787203 | 107 | L.TFKGFKRKDGKTGIRNELWIVPTVGCVNGIAELIIKEF |
| 15893984 | 107 | L.TFKGYRREDGTVGIRNELWIVPTVGCVNGTADLIAERF |
| 121533397 | 106 | H.TFRGYRRPDGRVGVRNEIWIIPTVSCVNRTAQLLAERG |
| 15613053 | 108 | VRTFQGYVRDNGNVGIRNEIWIINTVGCINKTAERLAAIS |
| RAAC01076 | 121 | L.TFMGYVRSDGQVGVRNEIWILNTVGCVNKVAERLAAMA |

| | | |
|---|---|---|
| 52081816 | 146 | KAEVGSIAPFESVHVLKHQYGCSQLGDDHINTRTILANAV |
| 52787203 | 146 | KAEVGSIAPFESVHVLKHQYGCSQLGDDHINTRTILANAV |
| 15893984 | 146 | KSET....EFKDVHVFKHNFGCSQLGDDHNNTRTILGNIV |
| 121533397 | 145 | SALARNMANIDGVFAFTHPYGCSQLGDDHRATQTILADLV |
| 15613053 | 148 | NETCG..AGVDGVYHPHLFGCSQLGDDLLYTQKILRNLV |
| RAAC01076 | 160 | DAKWRG.GGIDGVYHFAHPYGCSQLGDDLVYTQSLLAGLV |

| | | |
|---|---|---|
| 52081816 | 186 | NHPNAGGVLVLGLGCENNSIHEFREALGDYDHSRVKFLLS |
| 52787203 | 186 | NHPNAGGVLVLGLGCENNSIHEFREALGDYDHSRVKFLLS |
| 15893984 | 182 | KHPNAGGVLVLGLGCENNTMESFKESLHSYNKERVRFLIA |
| 121533397 | 185 | NHPNAGAVLVLGLGCENNNVPEFQKVVGSYNADRVKFLVA |
| 15613053 | 186 | LHPNAAGVLVLGLGCENNHIAAFKQVLGDYDDRRVKFLAV |
| RAAC01076 | 199 | RHPNAAGVLVIGLGCENNRIEAFRERLDQASLERVAFLEL |

| | | |
|---|---|---|
| 52081816 | 226 | QEVSNEVTEGVKLLKEIYKHAKGDHREDVPLSELKIGLKC |
| 52787203 | 226 | QEVSNEVTEGVKLLKEIYKHAKGDHREDVPLSELKIGLKC |
| 15893984 | 222 | QDVEDEISSGCELLKELYEKIQKDEREEVSISELKIGLKC |
| 121533397 | 225 | QEVEDEIAAGLELLSDLIAYAGQFLREDCPASELVVGLKC |
| 15613053 | 226 | QEADNEMEQGLAIIEELISYAKTAKREPIPLSKLKVGLKC |
| RAAC01076 | 239 | QRTTDEFADGMRLLEDLVERARAFVRQPVPVARLKLGLKC |

FIG 7B

| | | |
|---|---|---|
| 52081816 | 266 | GGSDGFSGITANPLLGRLSDFLIAQGGTAVLTEVPEMFGA |
| 52787203 | 266 | GGSDGFSGITANPLLGRLSDFLIAQGGTAVLTEVPEMFGA |
| 15893984 | 262 | GASDGFSGITANPLLGKLSDFLIAQGGTTILTEVPEMFGA |
| 121533397 | 265 | GGSDAFSGITANPLVGAFSDLLIACGGSTVLTEVPEMFGA |
| 15613053 | 266 | GGSDGFSGITANPLVGAFSDKVVAHGGTTVMTEVPEMFGA |
| RAAC01076 | 279 | GGSDGLSGVTANPLVGQVADRVVARGGTALLTEVPEMFGA |
| | | |
| 52081816 | 306 | ETLLMERAENEEVFHKIVRLINDFKQYFIDHRQPVYENPS |
| 52787203 | 306 | ETLLMERAENEEVFHKIVRLINDFKQYFIDHRQPVYENPS |
| 15893984 | 302 | ETILMNRAKDEKVFAKTVNLINDFKKYFMSYNQPVYENPS |
| 121533397 | 305 | ETILMNRAQDKAVFDKTVRLINDFKNYFMAYNQPIYENPS |
| 15613053 | 306 | ETILMNRAKDQATFEKMVRLINDFKEYFLRHNQPVYENPS |
| RAAC01076 | 319 | ETVLMDRADSPETFAKIVDLIQSWKDYYTRHGQPVYENPS |
| | | |
| 52081816 | 346 | PGNKAGGITTLEDKSLGCTQKAG.TSKVADVLEYGDVLKK |
| 52787203 | 346 | PGNKAGGITTLEDKSLGCTQKAG.TSKVADVLEYGDVLKK |
| 15893984 | 342 | PGNKAGGITTLEDKSLGCTQKSG.SSEVVGVLKYGETLEN |
| 121533397 | 345 | PGNKKGGITTLEEKSLGCTQKGG.RATVVDVLGYGETVTR |
| 15613053 | 346 | PGNKEGGITTLEEKSLGCVQKGG.FAEVVDVLPYGERLEK |
| RAAC01076 | 359 | PGNKAGGITTLEEKSLGAVQKGGRLSRVVDVLGYGDPAVK |
| | | |
| 52081816 | 385 | KGLNLLSAPGNDLVASSALAAAGCQIVLFTTGRGTPFGTF |
| 52787203 | 385 | KGLNLLSAPGNDLVASSALAAAGCQIVLFTTGRGTPFGTF |
| 15893984 | 381 | KGLNLLSAPGNDLVASTALASAGCHMVLFTTGRGTPFGTF |
| 121533397 | 384 | KGLNLLNGPGNDAVAATALAAAGCHLVLFTTGRGTPLGTA |
| 15613053 | 385 | PGLNLLQGPGNDLVSVTALAAAGAHFVLFTTGRGTPFGGP |
| RAAC01076 | 399 | PGLNLISAPGNDMVSVSALAASGAQLILFTTGRGTPFGGP |
| | | |
| 52081816 | 425 | VPTMKISTNTAIYEAKRHWIDFNAGKVLEDRSEDDVLKEL |
| 52787203 | 425 | VPTMKISTNTAIYEAKRHWIDFNAGKVLEDRSEDDVLKEL |
| 15893984 | 421 | VPTVKISTNSDIYNKKKNWIDFNAGALLENQSMDQVLKEF |
| 121533397 | 424 | VPTVKIATNSELFRRKTTWMDFNAGELLEGKSLEALADEF |
| 15613053 | 425 | VPTVKISTNTSLYERKKHWIDFNAGRLVEGATLDEVAEEL |
| RAAC01076 | 439 | VPTLKIASNHQLASSKPGWIDFDAGRIALGESMNDLAEEL |
| | | |
| 52081816 | 465 | TAYLIEVASGRQ.LNNEINDFRELAIFKTGVTL |
| 52787203 | 465 | TAYLIEVASGRQ.LNNEINDFRELAIFKTGVTL |
| 15893984 | 461 | INYLLGVANGNM.ANNEKNNIREISIFKNGVTL |
| 121533397 | 464 | FAYVLAVASGRP.TKAEEMGFREIAIFKNGVTL |
| 15613053 | 465 | LNYGVKLASGEVRAKNEEYGFKEISIFKDGVIL |
| RAAC01076 | 479 | LHKVIRVASGEELARNEVNGYREIAIFKDGVTL |

FIG 8A

```
114843317    1              MDYKDLLKKLSESYGVSGHERGIYDLLKKEF
76795342     1              MDYKNLLKKLCESHGVSGHERGIYDLVKEEF
76796625     1              MDYKDLLKKLSENHGVSGHERGIYDLLKKEF
20515428     1              MDYKELLKKLSESHGVSGHERGIYQLLKKEF
125973125    1              MDYINILKDLSTYPGVSGQEDKLSGYIAKLF
RAAC01219    1  MRYEEVSPLSKYVSVFKQLLEAHGGPGFEEDVRNLILPHL 114843317    32  EPISDEVKEDNFGNLIFKKKGTKG..KYKVMLAAHLDEIG
76795342     32  AQISDEVTEDKFGNLFFLKKGTKG..KYKVMLAAHLDEIG
76796625     32  EPISDEVKEDNFGNLIFKKKGTKG..KYKVMLAAHLDEIG
20515428     32  EEISDEVLEDNFGNLIFKKKGLKG..KYKVMLAAHLDEIG
125973125    32  EKYCDSVEIDEFYNVIGIKKGIGGSGGRRIMVTAHLDEIG
RAAC01219    41  SEYATEMWTDALGNLIGLVPGVGEGRRPRVLVSAHIDEIA 114843317    70  LMVKDIDEKGFIKFTTVGGVDQRTLPSQEVIVHGKK.DLL
76795342     70  LIVKDIDDKGFIKFTTVGGIDQRTLPSQEVIVHGKK.DIL
76796625     70  LMVKDIDEKGFIKFTPVGGVDQRTLPSQEVIVHGKK.ELL
20515428     70  LMVKDIDEKGFIKFTPVGGVDQRTLPSQEVIVHGKK.ELL
125973125    72  LMVKSIDEKGFITVSNIGGVDSKVLLAQEVVIHGKK.EIY
RAAC01219    81  LVVTRIESGGFLRLAQAGGFDPRTLVGQEVVVHAQSGRVW 114843317   109  GVIGSKPPHLLSSEDMEKAIKIDDMYVDVGLPKKEVEELV
76795342    109  GVIGSKPPHLLSLGDMEKAIKIEDMYIDVGMSKKEVEELV
76796625    109  GVIGSKPPHLLSSEDMKKAIKIDDMYVDVGLPKEEVEKLV
20515428    109  GVIGSKPPHLLSSEDMEKAIKIDDMYVDVGLPKEEVEKLV
125973125   111  GIIGAKPPHLLTPEEIKKAVKMEDLVIDTGLSAEEVRKYV
RAAC01219   121  GVIGAKPPHLTPPSERSKAAKLEDLYVDLALPEEEVRARV 114843317   149  KIGDIITIKRDFRELLNDYVSGKALDDRAGIVVMAVCLDE
76795342    149  KIGDVITIKREFRELLNDYVSGKALDDRAGIAVMAVCLEE
76796625    149  SIGDIITVKREFKELLNENVSGKALDDRAGVVVMAVCLEE
20515428    149  SIGDIITVKREFRELLNDNVSGKALDDRAGVVVMAVCLDE
125973125   151  SVGDIVTFKVEPLVLQNNRFSSKSLDNRAGVVALLDIMEN
RAAC01219   161  RVGDRVTLRRSPVDLLNGRIAGKSVDNRASAAVLLEALAL 114843317   189  LKKLYHYHDVYAVVTLQEEVGVRGATTSAYNVEPDIAIAI
76795342    189  LNKLYHYHDVYAVATLQEEVGVRGAITSAYNVEPDIAIAI
76796625    189  LKKVYHYHDVYAVVTLQEEVGVRGATTSSYNIEPDIAIAI
20515428    189  LRKMYHYHDVYAVATLQEEVGVRGAITSSYNIEPDIAIAI
125973125   191  LTLLNHKDDVWFVATVQEEVGLRGANIAAYNINPDLAIVI
RAAC01219   201  LKGMVHSADLYAVFTVQEEVGLRGARTAGFGLAPDIAIAV 114843317   229  DVTHGKARGVSLE..IELGKGPAIGKGPNIHPAVYKGLVE
76795342    229  DVTHGKARGLSIE..IELGKGPAIGKGPNMHPAVYKGLVE
76796625    229  DVTHAKARGVSRD..IEIGKGPAIGKGPNIHPAVYKGLVD
20515428    229  DVTHAKARGVSRD..IEIGKGPAIGKGPNIHPAVYKGLVD
125973125   231  DVCHGQIPGTPKESVFPVGKGPAVAVGPNLHRKYTKKMIE
RAAC01219   241  DVTFGAFPGQAPDESFPLEGGVAISFGPNLHRRVFRRLVD
```

FIG 8B

| | | |
|---|---|---|
| 114843317 | 267 | AAKNYNINYQVEPLPGPSGTDAWAIQVSREGVPTGLVSIP |
| 76795342 | 267 | AAKSYNINYQVEPLPGPSGTDAWAIQISKDGVPTGLVSIP |
| 76796625 | 267 | IAKKYNINYQIEPLPGHSGTDAWAIQVSKKGVPTGLVSIP |
| 20515428 | 267 | IAKKYNINYQIEPLPGHSGTDAWAIQVSKKGVPTGLVSIP |
| 125973125 | 271 | LAKEENIPYQIDVEPGDTGTEAWAVQVSREGIPTLLVSIP |
| RAAC01219 | 281 | CADRHRIPYQIELSQGPVGADANAFQIAGPGLAAALIGPP |

| | | |
|---|---|---|
| 114843317 | 307 | LRYMHTSVETANMKDVISSGKLLAYYIANLP.EELEGHLC |
| 76795342 | 307 | LRYMHTSVETANMKDIINSGKLLAYYIANLP.EELEGHLC |
| 76796625 | 307 | LKYMHTSVETANMKDIIESGRLLAHYIANLP.EELEGHLC |
| 20515428 | 307 | LKYMHTSVETANMKDIIESGRLLAHYIANLP.EELEGHLC |
| 125973125 | 311 | LKYMHTVIETLSIDDIKNTGRLIARFISMTG.NEMEEGLC |
| RAAC01219 | 321 | IRYMHTSVETVAYDDIWQCARLLAHYLAEVDAAQVEELTC |

| | | |
|---|---|---|
| 114843317 | 346 | Y |
| 76795342 | 346 | Y |
| 76796625 | 346 | Y |
| 20515428 | 346 | Y |
| 125973125 | | |
| RAAC01219 | 361 | Y |

FIG 9A

| | | |
|---|---|---|
| 125973126 | 1 | MLIKELTELNGVSGNED |
| 15893508 | 1 | MLLDKLCNAAGPSSFEG |
| 20515429 | 1 | MLLKELTELLGASGDEK |
| 76796624 | 1 | MLLKELTELLGASGDEK |
| 114843316 | 1 | MLLKELTEIMGASGDEK |
| RAAC01220 | 1 | MAVRATPRPLLGGGRRRAGGGVDMLLKELTEAFGPTGFED |

| | | |
|---|---|---|
| 125973126 | 18 | EVRKFIKEEAQKYADSITEDSMGNLICYKKGGSSKYRVML |
| 15893508 | 18 | DVRAIIKKEIKAFVDEIKVDRMGNIIAHKKG..SGKKIML |
| 20515429 | 18 | EVREKIKEIVKPYVDELYVDRIGNLIACKKGKKEKPKVML |
| 76796624 | 18 | EVREKIKEIVKPYVDELYVDRIGNLIACKKGKKEKPKVML |
| 114843316 | 18 | EIREKIKSIVEPYVDNVYVDKIGNLIACKKGKKDKPKIML |
| RAAC01220 | 41 | EVRGIVRRELDAMGLSVRTDVLGNVIASTGEHHPGPRVML |

| | | |
|---|---|---|
| 125973126 | 58 | SAHMDEVGFMVTGY.....DDGLIKFASIGGIDERILPGK |
| 15893508 | 56 | DAHMDEVGFIITSIN....EDGTIKFASIGGINGKIIPSK |
| 20515429 | 58 | AAHMDEVALMVKSVN....EDGTLSFSPVGGVDNRILVAK |
| 76796624 | 58 | AAHMDEVALMVKSVN....EDGTLSFSPVGGVDNRILVAK |
| 114843316 | 58 | AAHMDEVGLMVKSVN....EDGTLSFFPVGGVDNRILVAK |
| RAAC01220 | 81 | DAHMDEVGLMVTHIGEGREEGGLLRFRPLGGVDPRVLVSK |

| | | |
|---|---|---|
| 125973126 | 93 | RVLVGEKRIPGVIGSKPIHLQEKAERGNNIKLKNMYIDIG |
| 15893508 | 92 | VVYIGENKIPGVIGIKPIHLQSAEERKGSASYDNCFIDIG |
| 20515429 | 94 | AVKVGEKKINGVIGAKPIHLQKKGEQEKPLDFDELYIDIG |
| 76796624 | 94 | AVKVGEKKINGVIGAKPIHLQKKGEQEKPLDFDELYIDIG |
| 114843316 | 94 | TVKVGEKGINGVIGAKPIHLQKRDEQQKPLDFDSLYIDIG |
| RAAC01220 | 121 | PVLIGERRIPGVIGAKPVHLQQPSEREKPIPMEKLYIDIG |

| | | |
|---|---|---|
| 125973126 | 133 | AEKKEEAEKLAPLGEYIAFYSMYTEFGDGCIKAKALDDRV |
| 15893508 | 132 | SKSKEETKKYVSLGDYAVFSTEYGEFGEGFIKAKALDDRV |
| 20515429 | 134 | AASKEEALKHISPGDYVYFESNFEILGDGYVKAKALDDRI |
| 76796624 | 134 | AASKEEALKHVSPGDYVYFESNFELLGDGYVKAKALDDRI |
| 114843316 | 134 | ATSKEEALKHVSPGDYVYFDSNFEILGNGYVKAKALDDRI |
| RAAC01220 | 161 | ARDADDARRHVKPGDPVVFATAYQELPHRMAKAKSFDDRV |

| | | |
|---|---|---|
| 125973126 | 173 | GCAILLEILKERY.GFDLYVCFTVQEEIGLRGAGVAAFRV |
| 15893508 | 172 | GCAVLIELLKENY.ECDLYAVFNVQEEVGERGAYVSAFQV |
| 20515429 | 174 | GCNVLIEILKNTY.EYPVCAAFTVQEEVGLRGAGVAAYNV |
| 76796624 | 174 | GCNVLIEILKNTY.EYPVCAAFTVQEEVGLRGAGVAAYNV |
| 114843316 | 174 | GCNVLIENLKNEY.EYTVCAAFTVEEEVGLRGAGVAAYNV |
| RAAC01220 | 201 | GCYILLEALRRWKGALPVFGAFTVQEEIGLRGAHAAAYQI |

| | | |
|---|---|---|
| 125973126 | 212 | NPDIAIVVEGTTCSDVPGAREHEYSTVMGNGAALTIMDRT |
| 15893508 | 211 | RPDIGIALEGTVCADMPNVPEYLRATELGKGPAISIMDKS |
| 20515429 | 213 | EPDFALVVEGTVAADVVDSEPHLVSTELGKGPAISLMDRT |
| 76796624 | 213 | DPDFAIVVEGTVAADVVDSEPHLVSTELGKGPAISLMDRT |
| 114843316 | 213 | EPDFAIIVEGTVAADVTDSVPHLVSTELGKGPAISLMDRT |
| RAAC01220 | 241 | EPDIAIALEGTVAHDVVGTPSHGQSTVVGKGPAITVQDGQ |

FIG 9B

| | | |
|---|---|---|
| 125973126 | 252 | SYSNKKLVDFMYKTAKDKNIPVQYKQTATGGNDAGKIQLT |
| 15893508  | 251 | SIYNEEITLELIKIAKENNLAHQMRKSTSGGNDAGAIAST |
| 20515429  | 253 | TLYDRKIIDKIVRIAEENNVPYQFRRIASGGNDAGKIHLT |
| 76796624  | 253 | TLYDRKIIDKIVKIAEKNKIPYQFRRIASGGNDAGKIHLT |
| 114843316 | 253 | TLYDKKLIDKIAKIADENKVPYQFRRIASGGNDAGKIHLT |
| RAAC01220 | 281 | TVANRRFAEFLWETAKARNIPVQWRRVKGGTNDFGAIHRV |

| | | |
|---|---|---|
| 125973126 | 292 | REGVVVASVSVPCRYIHSPVSVMNRRDYESCLNLVKAVLE |
| 15893508  | 291 | GEGAKVAAVSVPCRYIHSSVSVASLKDIENTIELLKKYLL |
| 20515429  | 293 | KGGIKTVAISVPCRYIHSFNSVAKLSDFENTVKLVDLVIK |
| 76796624  | 293 | KGGIKTVAISVPCRYIHSFNSVAKLSDFENTVKLVDLVIK |
| 114843316 | 293 | KGGIKTIAVSVPCRYIHSFNSVAFLEDFNNTVKLVDLIIK |
| RAAC01220 | 321 | GKGVLGGAISVPVRYIHAPTQVVSLDDVSHAIDLVVAVLD |

| | | |
|---|---|---|
| 125973126 | 332 | EFDNNESLIESFKLHNVK |
| 15893508  | 331 | SFKGGK |
| 20515429  | 333 | NIEEVLK |
| 76796624  | 333 | NIEEVLK |
| 114843316 | 333 | NIEKEALI |
| RAAC01220 | 361 | EIAKGGFRP |

FIG 10

```
20515430    1   MSVNVELIKKLTQAFGPSGSEEKVFEIIREEVKGFCDEIT
76796623    1   MSVNVELIKKLTQAFGPSGSEEKVFEIIREEVKGFCDEIT
125973127   1       MFDLLKKFTGIVGVSGNEEEIREAIIEEIKECVDEIK
125973126   1   -----MLIKELTELNGVSGNEDEVRKFIKEEAQKYADSIT
RAAC01221   1       MRDWVMRLIDFVAPSGSEEAVVQSLLDHVREAADEIW 20515430    41  HDAMGNMICVKKGKGKK..IMVAAHADEIGIMVTHIEEEG
76796623    41  HDAMGNMICVKKGKGKK..IMVAAHADEIGIMVTHIEEEG
125973127   38  VDTLGNLIAVKKGKGKK..IMVAAHMDEIGVMVTYIDDKG
125973126   36  EDSMGNLICYKKGGSSKYRVMLSAHMDEVGFMVTGYDD.G
RAAC01221   38  VDALGNGIARKRGEGPH..LMLAAHVDEPGVMVIDIDDRG 20515430    79  FLRFTTIGGVYVEHLVGRRVKFKN....GTVG..VIG.VE
76796623    79  FLRFTTIGGVYVEHLVGRRVVFKN....GTVG..VIG.VE
125973127   76  FLRFSAVGGVSRYDCIGQRVKFKN....GVVG..AVYYEE
125973126   75  LIKFASIGGIDERILPGKRVLVGEKRIPGVIGSKPIHLQE
RAAC01221   76  YLRVVSVGEVHARECVGQEVRFTN....GAVG....LVHA 20515430    112 HLEDKKDFKLEKLYIDIGAKDKKEAEELVKIGESGSFVGE
76796623    112 HLEDKKDFKLEKLYIDIGAKDKKEAEELVRIGDSGAFVGE
125973127   110 KLEDMKNLQLSKMYIDIGARSREEALKMVNIGDVACFVGD
125973126   115 KAERGNNIKLKNMYIDIGAEKKEEAEKLAPLGEYIAFYSM
RAAC01221   108 DPAKQGDLDFDALVVDVGARSREDAERMAPIGTAGAVHVP 20515430    152 FVEAGD.RLISKAFDDRIGCYVAIEALKNVK.TENELYFV
76796623    152 FVEAGD.RLVSKAFDDRIGCYVAIEALKNVK.TENELYFV
125973127   150 AVLQGD.TVISKALDNRSGCAVVVKAIKELKKTDNEIYFV
125973126   155 YTEFGDGCIKAKALDDRVGCAILLEILKERY..GFDLYVC
RAAC01221   148 AATWGESVVTGRALDNRLGCAVAAEVFRNLAARGLNVSVA 20515430    190 FTVQEEVGLRGATTAAYSINPDFAIAVDVTATGDTP..KA
76796623    190 FTVQEEVGLRGATTAAYSINPDFAIAVDVTATGDTP..KA
125973127   189 FTVQEEVGLRGAKTAAFSIKPDIAIAVDVTMTGDTP..ES
125973126   193 FTVQEEIGLRGAGVAAFRVNPDIAIVVEGTTCSDVPGARE
RAAC01221   188 FTAQNAVGARAAQAAAFQLEPRYALVIDGATADDVFN...

20515430    228 KKMAVALGKGAAIKVMDRSIIVSPSVRDMMIEVAKENSIP
76796623    228 KKMAVALGKGAAIKVMDRSIIVSPSVRDMMIEVAKENNIP
125973127   227 HPMEVKCGGGPAIKVKDRSVICHPEVRKLLEESAKRNNIP
125973126   233 HEYSTVMGNGAALTIMDRTSYSNKKLVDFMYKTAKDKNIP
RAAC01221   225 HQTVLSLGKGPVLKVMDRGTVVPLEGKRAVEKAADRLNLL 20515430    268 YQLEILEFGGTDAGAIHLSRGGVPSGVISIPTRYVHSVSE
76796623    268 YQLEILEFGGTDAGAIHLSRGGVPSGVISIPTRYVHSVSE
125973127   267 YQLEILEAGGSDPGSIHLTAGGIPSGAISIPVRYVHSPVE
125973126   273 VQYKQTATGGNDAGKIQLTREGVVVASVSVPCRYIHSPVS
RAAC01221   265 LQYEVSREAWSDTGAIQLARAGCVAVALGYPVRRAGAFAM 20515430    308 MVDKKDVEASINLLIKILEK
76796623    308 MVDKNDVEASINLLIKILEK
125973127   307 TASMSDINNAVKLLVEAIC
125973126   313 VMNRRDYESCLNLVKAVLEEFDNNESLIESFKLHNVK
RAAC01221   305 TADISDAERLVDLAVATVETLLG
```

FIG 11A

```
89098529
116620373
52081815
52787202
116623151
RAAC01275      1  MTCVHRWKRGLSAGASLALVAAAATGWTVHARFAHADNVV
```

```
89098529       1                           MAVYHIS
116620373      1            MKSTCRVALVGLLAACAWSAEFDVK
52081815       1          MSLQKIKEEIVKKLKVPVFPNRSFDVT
52787202       1          MSLQKIKEEIVKKLKVPVFPNRSFDVT
116623151      1             MRVLLLLIAALALRAAEFRVT
RAAC01275     41  DLVAQTGDLDASLAQVLHGAPFAMPIPSLPDIVPRVYDIT
```

```
89098529       8  EYLKGNAG..LATEGIQKAIDEAYQNGGGKVVIPAGEFLT
116620373     26  TFGAAGDGKKKDTAAIARAIDAAAKAGGGTVVVSPGRYLT
52081815      28  SFGADENGKNDSTEAIQKAIDQAHQAGGGRVTVPEGVFLS
52787202      28  SFGADENGKNDSTEAIQKAIDQAHQAGGGRVTVPEGVFLS
116623151     22  DYGAKADGKTVNTVALQKAIDAAAKAGKGVVVFAPGVYLS
RAAC01275     81  EYGAKPGIGQVNTQAIQAAIDAASQHGGGIVDIPPGYWVT
```

```
89098529      46  GPLFLKDNIELHLENGAHLKFSDKQEDYP.VVTSRWEGVK
116620373     66  GALTLKSNVTLDVEAGATLLGSPDPEDYP.LRENVWG..E
52081815      68  GALRLKSNVDLHIAKGAVIKFSQNPEDYLPVVLTRFEGVE
52787202      68  GALRLKSNVDLHIAKGAVIKFSQNPEDYLPVVLTRFEGVE
116623151     62  GALFLKSNMELRLDEGVEIRGVQDLAAYP.LMQTRVAGIE
RAAC01275    121  GPIVLKSHVDLNVESGAQLQFSGDHDLYP.....LVPSGN
```

```
89098529      85  RKVYASCLFAEGARNIAVTGFGTIDGNG............
116620373    103  KKEYSSLIYADGAVHITIRGRGTIDGQG............
52081815     108  LYNYSPLIYAYEADNIAITGKGTLDGQGD...........
52787202     108  LYNYSPLIYAYEADNIAITGKGTLDGQGD...........
116623151    101  MKWPAALLNVYEQSNVRLSGKGTVDGDG............
RAAC01275    156  SYIVQSPISATNAVDVAITGHGVIDGAGNTWRPVEKSKLS
```

```
89098529     113  ..................MEWWD..VFRNRR.........
116620373    131  ..................QAWWKRMGWPDRRKIAPEQRTA
52081815     137  ..................DEHWWPWKRGTNGQPSQEKDRNA
52787202     137  ..................DEHWWPWKRGTNGQPSQEKDRNA
116623151    129  ..................KIWWDLYWKMRREEYEPKGLRW
RAAC01275    196  ADQWNALVASGGVVSPDGSTWWPTAQGANAQAYIKAHPNM
```

```
89098529     124  ......EELKYP.........RPKLISFDHCEHITLRDV
116620373    153  AERAELAKLEYG.........RPHMIKLVRSKHVVIEGL
52081815     160  LFEMAERGIPVTERQFGKGHYLRPNFIQPYRCKHILIQGV
52787202     160  LFEMAERGIPVTERQFGKGHYLRPNFIQPYRCKHILIQGV
116623151    151  AVDYDCR..............RPRLIQIYKSQGVDLVSL
RAAC01275    236  TYQDDLQVKDYL.........RPYMVYFQGCQRVWLQGV
```

FIG 11B

```
89098529    148  RLINSPSWTVNPICCRDITVDNVSILN..PADSPNTDGID
116620373   183  HLINSASWTVNPLLCEFVRIDGITIEN..PVPSPNTDGIN
52081815    200  TVLNSPMWQVHPVLCENVTVDGIKVIG....HGPNTDGVN
52787202    200  TVLNSPMWQVHPVLCENVTVDGIKVIG....HGPNTDGVN
116623151   176  TLKRPGFWTVHICYSERVTVDGLTIRNNTDGKGPSTDGID
RAAC01275   266  TFENSPFATVKVNTSKDVVIDDVNIRN..PWYGQNTDGID 89098529    186  PESCRNVRISNCHIDVGDDCIAIKSGTEDTEERVAC..EN
116620373   221  PESCRNVQILNSRIDVGDDCVTLKSGKDEAGRRVGRPDEN
52081815    236  PESCKNVVIKGCHFDNGDDCIAVKSGRNADGRRINIPSEN
52787202    236  PESCKNVVIKGCHFDNGDDCIAVKSGRNADGRRINIPSEN
116623151   216  IDSSSDVLVAHCDIDCNDDAICLKAGRDADGLRVNLPTER
RAAC01275   304  VSADENVVLYRDVIDTGDDGIALESSGNDAAG..VFNEQD 89098529    224  ITITNCTMVHGHGAVVFGSEMSGDIRNVTIS..NCVFQDT
116620373   261  ITITNCVMLKGHGAVTIGSEMSGGVRNVVVS..NCVFQGT
52081815    276  IVIEHNEMKDGHGGVTIGSEISGGVKNVIAEGNLMDSPNL
52787202    276  IVIEHNEMKDGHGGVTIGSEISGGVKNVIAEGNLMDSPNL
116623151   256  VRITDNVVRGGAAGVTIGSETSGGIRHIEVD.HLTVMSAV
RAAC01275   342  VVVADCIVHNGHSGFAVGSYTDGGIRDVWVT..GDVYDGT 89098529    262  DRGIRFKSRRGRGGVVEDVRVDN.IVMEGVICPFIINLYY
116620373   299  DVGIRVKSQRGRGGIVEGFVVSN.VVMQDVASAFTLTSFY
52081815    316  DRALRIKTNSVRGGVLENIYFHKNTVKSLKREVIAIDMEY
52787202    316  DRALRIKTNSVRGGVLENIYFHKNTVKSLKREVIAIDMEY
116623151   295  PAGILFKSASTRGGTIEDIAIRN.VITVGVATPVSITLNW
RAAC01275   380  ESGLRFKSGVGKGGLVEDIDMDHIVMRDISGAAITFDDGY 89098529    301  FCGPR..........GKDQYVWDKNPYPVTAETPMFRRLH
116620373   338  AGTDK..........PGD.......LFPVGEGTPRLRDFR
52081815    356  EEGD.........................AGDFKPVVRTVD
52787202    356  EEGD.........................AGDFKPVVRTVD
116623151   334  NPAYSYAKLPEGVKDMPDYWRVLTEVVPPGKGIPHFRDVR
RAAC01275   420  VDNGADTS..............SLQAPGPNSYVPQFENMT 89098529    331  FANITARNVHASAGYIYGLAEQYATDITFSQIDISLAKNA
116620373   361  FSNITAR.GSKTAGQITGLKEMPIENITFTGVRI......
52081815    372  VKQLKSM.GGQYGIRVLAYDHSPVTGLKVADSEIDG....
52787202    372  VKQLKSM.GGQYGIRVLAYDHSPVTGLKVADSEIDG....
116623151   374  ISRVKST.GAQRAFAVSSYAESPLVDFQFKDIDIE.....
RAAC01275   446  ISNVSCEYAGQS.IYMNGLPNAPISNIMLDDVNIT.....

89098529    371  VPGKPAMMAGIEDMANRGFYVGFAKDVLFSRVTIENHEGP
116620373   394  .............QAETGMKITNAKDVTFQDVIIEAAKGD
52081815    407  .............VDVPMELKHVKDPVFSNLYINGKRYD
52787202    407  .............VDVPMELKHVKDPVFSNLYINGKRYD
116623151   408  .............AKTAGSIANTQGWKFENMTIKTADGT
RAAC01275   480  .............ANKPPQIQNTSNLVENQVQIQSGVTM
```

FIG 11C

```
89098529    411  AFHIEHSEDVEVISCKSRNTKEGEELVREVAAK
116620373   421  AVSVVDSVGIELGRLKGRAAT.....VRERP
52081815    433  SHKA
52787202    433  SHKA
116623151   434  TVK
RAAC01275   506  LGEIPH
```

FIG 12A

| | | |
|---|---|---|
| 15614786 | 1 | MPIFYTEQTKEFHLQTKGSSYIFTVLDNQQL |
| 90961985 | 1 | MPITYNEQSREFHLYNNKISYLIKILANEQL |
| 148544139 | 1 | ------MITFDEQQRVFHLKNKEISYLFSVEEGNIL |
| 76796346 | 1 | MPIHFNDKTRTFHLTAKDTSYIIHVLKNDAV |
| 114844315 | 1 | MSIHFNDKTKTFYLTAKDTSYVIYVLKNGAV |
| RAAC01615 | 1 | MAIGKGRPSMPIIFHSDERLFHLMTPRSSYVFRVGHDGLL |

| | | |
|---|---|---|
| 15614786 | 32 | GHLYYGKKIEHRDSFTHLLRFQRRATSSCVFEGNLEFSLD |
| 90961985 | 32 | GQLYFGKRIPNRGNHDYLVENTYRPVTSYVFDDDYSFSLG |
| 148544139 | 31 | SHLYFGPAIRNYHGERRYPRVDRGFSGNLPGSMDRTYSKD |
| 76796346 | 32 | LHAYFGKKIKNANIYHVLKLSHVS.IDTDNINFGNYLMLD |
| 114844315 | 32 | LHAYFGKIIKTPNIYHLLKLPHIS.IDNDIINFGNQLMLD |
| RAAC01615 | 41 | EHVYWGARLEDASDLVRLARACQR.LDARPEHMR.AIDIG |

| | | |
|---|---|---|
| 15614786 | 72 | LIKQEFPSYGTTDYREPAFQILQENGSRITNFEYKNHVIS |
| 90961985 | 72 | NVKQEYPAYGTTDQRRPALDIKQPNGSRITDFKYVSHKIY |
| 148544139 | 71 | DLLQEYSGNNTGDYRVPAIIIKTENGSRLTDFRYKSYKIL |
| 76796346 | 71 | FLPQEYPAYGNTDFRSPAYQIQLENGSTVSDLRYLSHKIY |
| 114844315 | 71 | FLPQEYPAYGNTDFRSPAYQIQLENGSTVSDLRYLSHKIY |
| RAAC01615 | 79 | SLRLEYPSFGTGDHRDPAYEVLQPSGSHASQLVYESHQIR |

| | | |
|---|---|---|
| 15614786 | 112 | SGKKPLKGLPATYVESEEEAATLEVFLYDSLIDVELVLTY |
| 90961985 | 112 | AGKRKLTGLPATYVEDSEATTLEINLYDELIQVTLCLQY |
| 148544139 | 111 | PGKPKLAGLPASYVKSDKEAETLEVILVDETIGAQLILSY |
| 76796346 | 111 | KGKPKLEGLPATYVENEDEADTLEIELYDKVANLKVTLIY |
| 114844315 | 111 | KGKPKLEGLPATYVENEDEADTLELELYDKVANLKVTLIY |
| RAAC01615 | 119 | PGKPPLPGLPAFYVESDFEADTLEISLVDPAISLRVILSY |

| | | |
|---|---|---|
| 15614786 | 152 | TVFAETNVITRHARFINHHSSPVQLMRALSMSVDLPDADF |
| 90961985 | 152 | TIFENSAAIARSVKFSNNSDQKYQLKTALSLNLDLPDANY |
| 148544139 | 151 | TIYNERPVITRNARLVNTSNQELRIEKIASMQLDLTKHDY |
| 76796346 | 151 | TAFRDYDVITRSVRFENMGKEDIKLLRALSMNVDFNDDKF |
| 114844315 | 151 | TAFRDYDVITRSVRFENMGKEDIKLLRALSMNVDFNDSNF |
| RAAC01615 | 159 | TAYRDFDLVCRHARLENAGTEPLVLRRALSASVDLDLREA |

| | | |
|---|---|---|
| 15614786 | 192 | QMLQLSGSWSRERYVKERALVPGIHQISSTRGASSSQQNP |
| 90961985 | 192 | EWLQFSGAWGRERHLHKTPLRPGIQAINSARGASSHMQNP |
| 148544139 | 191 | DVISVPGQYALERQPERQELRRGITEFSSRRNSSSHHMNP |
| 76796346 | 191 | DMLQLSGAWARERHVIRRPLTPGVQSIESRRGASSHQQNP |
| 114844315 | 191 | DMLQLSGAWARERHVIRRPLVPGAQSIESRRGASSHQQNP |
| RAAC01615 | 199 | DFVQLSGAWIRERFIQRTPLSPGRHEIMSRSGASGHKHNP |

| | | |
|---|---|---|
| 15614786 | 232 | FIALKRPQTTEFHGEVYGFSLVYSGNFLAQVEVDQYDV.S |
| 90961985 | 232 | FVILKRPFTTEEQGEALGVSFVYSGNFLAQAEVDEYSV.T |
| 148544139 | 231 | FVALVDKNTDEFQGNALGVLLVYSGNHQFTLEKDQIDQ.I |
| 76796346 | 231 | FIALLRKDADEWHGDVYGFSLVYSGNFLAQVEVDQYKM.A |
| 114844315 | 231 | FIALLRNDADEWHGDVYGFSLVYSGNFLAQVEVDQYNM.A |
| RAAC01615 | 239 | FFALAAPHTTEEGGEVRAFALVYSGNFLGACEMEPMRQNV |

FIG 12B

```
15614786    271  RVQMGIHPFDFQWLLEAGESFQTPEVVMVYTDQGLNHLSQ
90961985    271  RLQIGIDPFQFSWCLKPNETFQTPEAILAYTSEGLNQLSQ
148544139   270  RLITGINDYDFEWVLEPGKDFQTPEAIMGFSQQGLNGMSQ
76796346    270  RVSMGINPFDFSWLLKPGETFQTPEVVMVYSDSGLNKMSN
114844315   270  RVSMGINPFDFSWLLKPGETFQTPEVVMVYSDGGLNKMSN
RAAC01615   279  RAQIGIHPSDFSWRLEPGERFVTPEAALVYSDEGWGGMSR
```

```
15614786    311  LYHSLYRSRLVRGNWRDRPRPILLNSWEATYFDFTEDSLV
90961985    311  TFQKLYTTRLARGYWRDKERPILINNWEATYFDFTEEKLL
148544139   310  VFHKLLRDRVARGKYQYADRPIVINNWEATFFDFDDKKLD
76796346    310  TYHKLYRNRLMRSKFKDKERPILINNWEATYFDFTEEKLK
114844315   310  TYHKLYRNRLMRSKFKDRETPILINNWEATYFDFTEEKLK
RAAC01615   319  TFHRAIRKRLCRGTYRDRVRPVLINNWEATYFHFDEEDLV
```

```
15614786    351  EFAKEGKKLGVELFVLDDGWFGTRNDDTTSLGDWFVNSEK
90961985    351  SIAKKAKELGIELFVLDDGWFGERTKETAGLGDWYVNRNR
148544139   350  QIIDEAKPLGIEMFVLDDGWFGHRNDDNSSLGDWFVNQDK
76796346    350  ELAKEAKDLGIELFVLDDGWFGKRNSDNSSLGDWFVNKEK
114844315   350  ELAKEAKDLGIELFVLDDGWFGKRNSDNSSLGDWFVNKEK
RAAC01615   359  EIAEQARDLGAEMFVLDDGWFGQRDDDHTSLGDWWPHPRK
```

```
15614786    391  LPNGIEGLAEKIEALGLAFGLWFEPEMVNKESELFKKHPD
90961985    391  LKNGISGLSRKIHDLGMMFGLWFEPEMVNKDSDLYRKHPD
148544139   390  LTGGLKRVADRTHEHGMKFGLWFEPEMISVDSKLYKEHPD
76796346    390  IPSGLDGLAKGINSLGLKFGLWMEPEMVSPDSDLYREHPN
114844315   390  IPSGLDGLAKGINSLGLKFGLWMEPEMVSPDSDLYREHPD
RAAC01615   399  LPNGLRHLADRIHALGLRFGIWMEPEMVSPKSELYREHPD
```

```
15614786    431  WIIHVEGRSQSHGRNQYVLDFSRAEVVDAIYEMMAELLRK
90961985    431  YIIETPKRHASHGRKQYVLDFSRKEVVDNIYEQLVKILDE
148544139   430  YALHEPNRGMTLSRNQLVLDFSRKEVVDNIYNQMCLILDK
76796346    430  WCIHVPNRPRSESRNQLVLDLSRKDVQDYIIKVVSDILES
114844315   430  WCIHVPNRSRSESRNQLVLDLSRKDVQDYIIKVVSDILES
RAAC01615   439  WCLHVADRPRSERRHQLMLDLTREDVRAFVVNAVSRVIEE
```

```
15614786    471  APISYIKWDMNRHLTEIGSPAWPKERQQEIAHRYILGVYD
90961985    471  GEIDYIKWDMNRNITECYSIAYPPEQQGEIMHRYILGVYD
148544139   470  VLLDYIKWDFNRNLTEVFSSAADADHQGEISHRYVLGLYD
76796346    470  ANISYVKWDMNRNMTEIGSALLPPERQRETAHRYILGLYR
114844315   470  ANISYVKWDMNRNMTEIGSALLPPERQRETAHRYILGLYR
RAAC01615   479  GAVDYIKWDMNRPMTEVGSAALPPERQREVAHRYVLGLYE
```

```
15614786    511  LYERLVSEFPDVLFESCASGGCRFDPGMLYYAPQTWTSDD
90961985    511  LYERLIERYPKILFESCASGGGRFDAGMLYYAPQAWTSDD
148544139   510  LMERLVTRYPNILFEGCSGGGGRFDAGILYYMPQSWPSDD
76796346    510  ILEEITTRFPDVLFESCAGGGGRFDPGMLYYMPQTWTSDN
114844315   510  ILEEITTRFPDVLFESCAGGGGRFDPGMLYYMPQTWTSDD
RAAC01615   519  ILETLTSRFPNVLFENCASGGGRFELGMLHYMPQTWTSDN
```

FIG 12C

```
15614786    551  TDAIERLKIQYGTSMVYPLSSIGAHVSAVPNHQVRRVTSL
90961985    551 -SDAIERLKIQYGTSFGYPQSMMGAHVSASPNEQLGRNTPL
148544139   550  TDAVERLKIQYGTSLTYPISSMTAHVSVSPNQQTGRSTSF
76796346    550  TDAVERLKIQYGTSIVYPLISMGSHVSAVPNHQVHRITPL
114844315   550  TDAIERLKIQYGTSIVYPLISMGSHISAVPNHQVHRITPL
RAAC01615   559  TDAVSRLKIQHGTSLVYPPVAMGAHVSAVPNHQMGRVTPF 15614786    591  ETRGNVAFFGAFGYELDVTQLTDEEKENMKKQIAFYKEHR
90961985    591  KIRGDVAFFGAFGYELDLDKLSSTELASIKKQIELMKKYR
148544139   590  KMRGDVAMSGVFGYELDLADLTEEDRQMVKEQIKFYKAHR
76796346    590  KTRLDVAISGNFGFELDLTKLSEEEKDLAKKYVKKYKEIR
114844315   590  KIRAHVAMSANFGFELDLTKLSSEEKDEIKKYVEKYKEIR
RAAC01615   599  ALRAGVAMCGNFGFELDPRRLSDAERREARQAVERYKALR 15614786    631  ELIMFGTFYRLRSPFVGDGNVTSWIVVSEDQSEALVGYYQ
90961985    631  SIFQYGTFYRLKSPFEG..NIVSWMVVSEDKSQAIVGYYK
148544139   630  HLIQYGAFIRLESPFDS..NTVAWEFVSPDKSEALLFMFK
76796346    630  KLIQFGDFYRLLSPFEG..NETAWMFINEEKTEFVAFYFK
114844315   630  KLVQFGDFYRLLSPFEG..NETAWLIVSEDKREFLLYYFR
RAAC01615   639  HLVQFGDFYRLLSPFDG..PEAAWMFAVEDGSEALVAYFC 15614786    671  TLAKVNAGFRQLKLTGLQECGLYQIDGMIGTYGGDELMHS
90961985    669  ILNDVNCEYRRLCLPGLDADTLYNVQEELGSYLGN.FTGD
148544139   668  QLHTNRFEINNTKMAGLDPTIDYHDEMTDKTYGGD.....
76796346    668  VLATPNDTIKRIYLKALNPDYKYALQDTGEVYGGD.....
114844315   668  VLGGANEPIKRLRLKGINPDFNYVLEDDGSEYSGD.....
RAAC01615   677  TYPDPLDPPARVVLRGLRPEARYRCEALGESFRGD.....

15614786    711  GLQLPNEFSGASALREDEQSGDFQSYVFKLKRIESDRH
90961985    708  ELANIGLVTTDASAGQNQETTDFYSKLFILERCGELSD
148544139   703  ELMNVGLFR......DPTHTGDFISEVHYFKGE
76796346    703  ELMYAGIAI.......PQLEGDFQSVMMHFKKEA
114844315   703  ELMYAGKVI.......PELKGDFQSIMMHFKEESIKDG
RAAC01615   712  ALMRHGLVI.......PRQVGDGQAVLIHLKQIGEGDRP
```

FIG 13A

```
76795700
114844102    1   MWYIVALVLLLIATSIVHISKNQRLSREDSIR..DFDD
20517160     1   MWYAVFVLILLLAG...IYLKSKKIEVDDSMR..EFDD
125973736    1   MQMQLYILYLLGLFGILLCLFLLAIFSNCNERQRQLKVQD
118725340    1       MNNILILLIITLIAIVAALIGIVLK.NRPSYEVQIED
RAAC01621
```

```
76795700
114844102   37   IILNSEEMEKHAAEIAQNHNIMKRTKLSYLLIPRMNKNYN
20517160    34   IILSSEEMEKHAEELAQNHVIANRNRASFLLIPRMNKNYE
125973736   41   ASLTFDELEAYAKEIAIEHSVSGKKSMFSWPIPRMNDNYR
118725340   37   VFLNSDDLMRHAEQLAKTQTTDKRKLGIRRVRERIERNFH
RAAC01621    1      MAFDTELERRAHALALTQDISSTRGGGSDLWPILRRKAA
```

```
76795700
114844102   77   YIKNVYRNLNSILKEEDVYISQEEEWLLDNFYIIEEQVKE
20517160    74   YIKSVYRSLNNLLKEKDTYISQEEEWLLDNFYIIEEQVKE
125973736   81   YIMSVYKEMN.EDVQKGISTTPAAEWLLDNFYIIEEQVKS
118725340   77   RVLEMYQKFN.LDISASFPVPPAAEWLLDNFYIIEEQKSM
RAAC01621   40   RVRNLATRLE...REPAACSEPAHEWLIDHAAYLELQAML
```

```
76795700
114844102  117   IRKSLSKSYYSGLPGLKNGLFKGYPRIYAIAFELVLHTDG
20517160   114   IRKSLSKKYYAGLPVLKNGAFRGYPRVYALAFELVLHTDG
125973736  120   LRRDLTKEVYAKLPVLDSGHLKGYARIYSIALELLSHTDG
118725340  116   LMKELS.EVKQALPVISEGTYAGYPRVFAIAADLVSHCDG
RAAC01621   77   AERLWPNAVVRKLPRMAE...TGEPRVVTLAAAYLDATRG
```

```
76795700
114844102  157   KIDEKAIINFIKAYQTKALLSSSELWALSLMIRIALVEKI
20517160   154   KIEEKGIINFIKAYQKKALLTTSELWALSLMIRIALIEKI
125973736  160   RIDEKVLVNYIKAYQSNNVLTGRELWAFPIMLKLVLIEKT
118725340  155   NVNEKIIRDFIAAYQKHTFLSIQELWMLSTMLKAALLEKL
RAAC01621  114   HVEAETLIRFVEAYQDVQVLTTHECHQLANGLRVAILTRL
```

```
76795700
114844102  197   KKICEKIVETRHQREKAEKILTLLLEKEMKYEEVKKLIRN
20517160   194   KKVCEEIVESRLQREKAEKMLSALMEKEMSYEEVKKLIKS
125973736  200   RYICEKIAKAQEQRRKVEEILKAFDENIENTTQLITAIDN
118725340  195   WAVCDRMFTNRQDWYRAEGIVNGIRHNNENCDDFRRHID.
RAAC01621  154   AEASDEIQHRYETCRAVGRLLDEIERG..DGPVAVRRAID
```

```
76795700
114844102  237   NINVADRFPLQFIEHLVSRLRKEGSNSVNVIQSIEKILME
20517160   234   NIKVVDRFPLQFVEYLVSRIKREGSNSSDILKTLEKILME
125973736  240   ELKGKYEVNSAFIEYLAYKFRKMGRAYTHVLRYIDERLGE
118725340  234   ...QLEEITPAFAEHLIKKLRKDGAKTLWMIECLDSILVQ
RAAC01621  192   RFSKGRGLGAVEVVHLVHHLSEWEPDSQELREWLAAHVAN
```

FIG 13B

```
76795700
114844102   277  YDTSINDVAEKAHQIQAKRQISIGNAITSLKTVSSLDWAQ
20517160    274  YDSSINDIAEKAHYFQAKRQVSIGNAIVSLKTVSSLDWAE
125973736   280  SGTTVDDITQKEHNEQTASKASIGNCIMSLKFISTVNWVD
118725340   271  KSTSTDSLISEDHFNQATLQVSTGNVINSFRALSGFDNTV
RAAC01621   232  SSESIERLTTYEAEWHAEIQVLIGNLVQSLHALERMSWQP
```

```
76795700
114844102   317  IFESLSSVEQVLRQDPDGTYPKMDFESRDYYRHEIEKIAK
20517160    314  IFETLSPVEQVLKQDPDGTYPKMDFESKDYYRHEIEKLAR
125973736   320  IFEQLSKVEQILREDPSGFYSLMDFDSRNYYRNRVEKLAL
118725340   311  LFEQLSEVERLLKLDPCGIYPQMDFDSRNYYRDIVMNLGS
RAAC01621   272  IASRISRVESCLRQEPTGDYLRLDPTSQNVLTQQVSWLSE
```

```
76795700
114844102   357  YYNTSETYVAKKAIECAKEVTEQEGKLG......YINHVG
20517160    354  YYNVSETYVAKKAVECAREVADQGENLG......YINHVG
125973736   360  KYKVSESHVAKKAVELARNAVENGNLTDK.....RLTHVG
118725340   351  KYDTTEINIARLCLDLAREKYDENPSIT......AETHVG
RAAC01621   312  AFRLPEAMIAETAVSLAREAWEKAGSPTASSDLPREAFVA
```

```
76795700
114844102   391  FYLVGKGRSILENKLSNKSKRTISWRKIAKKSPETLYVGL
20517160    388  FYLIGKGRSILESKLNNKKRRFFDFYRIRQKNPATVYFGL
125973736   395  YYLVGKGICELEKEIGYEKSFNQRMFERIKEHPACLYFGF
118725340   385  YYLAGKGRSAFSNKIG.......KYKEHSFKNCEKWYITA
RAAC01621   352  YYLCDPDGMHALHRSLKERAKPRSVPQIALRRRPLRSYLL
```

```
76795700
114844102   431  ILIFLLVEEFFALKYIANFSNKWGLLFISGVILL..IPFS
20517160    428  IILFFALGEIISLGYLRHFTGSFWNLFASSLVLA..IPLS
125973736   435  IGFITVLLLLCVTKYSLFRAEKYGIALSIIAVLATIIPAT
118725340   418  IVLFSVVIALIPTVNSFSRENGRLAFIVLLTGILSIIPAS
RAAC01621   392  GVAFLFAAILWAVLGGFTGGFRAPLGATLALAVLLALPVS
```

```
76795700
114844102   469  EMSVQLVNWILVHIFKPVVLPKIELKEGIPEDAKTMVVIS
20517160    466  EISIQMTNWVLMHIFKPVMLPKIELKDGIPDDAKTFVVIS
125973736   475  DIAVNFVNWVLCKMIKPSLLPKLDFENGIPEEYATMVVIP
118725340   458  EIVVSVLNSCISRIVKPARLPKLELNDGIPEDWATMVIIP
RAAC01621   432  EWVISLVHEGIRRAVRPVPLLRLDFSEGIPEDARTLIVLP
```

```
76795700
114844102   509  SLLPDEKRTKELIENLEVYYHANREKNLYFGLLGDFKDAP
20517160    506  SLLPDEKKAKELVENLEVYYHANRERNLYFGILGDFKDAP
125973736   515  ALLPDENRARELIDNLEVYYLANREKNLYFSIAGDFKDAP
118725340   498  TLIPNVKRTVELIDNLEVFYLANKGSNIYFSLAGDFKDSD
RAAC01621   472  VIWASEADVDEAFDKIELHHLTNRGAHLYFAVLSDLRDAD
```

FIG 13C

```
76795700
114844102   549  FEVMSEDEKIVKCALEQIEKLNEKYSKNGE.......KIF
20517160    546  LEVMPEDEKIVKATLEEIEKLNEKYAENGE.......KVF
125973736   555  NKEMAGDKKIIETALGRIAELNEKYGRKNEGGEKDSRDIF
118725340   538  DETLSDDNEIVEAAIKRVQDLNRKYCKDAK.......PIF
RAAC01621   512  APHLPEDEPLLARARARLEALRHKYG..........AARF 76795700
114844102   582  YYFHRKRKYNQMQKSWMGWERKRGALVEFNELLRGKEDTS
20517160    579  YYFHRKRIYNEMQKSWMGWERKRGALMEFVDLLRGEKDTT
125973736   595  YYFHRHRQFNEKQNKWMGWERKRGALLEFNEVLLGSRTTS
118725340   571  YFFCRKRRYNEKQKKWLGWERKRGAILEFNRLLRRDRNTD
RAAC01621   542  FWFHRDRVLNRADGVYMGWERKRGKLVEFVELLRGKRDTT 76795700
114844102   622  FYVVSGDVAKLN.IKYVITLDADTNLPIDTAKKLVGTMLH
20517160    619  FYIVSDDVSKLG.IKYVITLDADTNLPIDTAKKLVGAMLH
125973736   635  YSIMSHDVSQLPKIKYVITLDADTILPLGAARKLIGTMAH
118725340   611  YVFNSATIDSLPNIKYVITLDADTQLPLDTAKQMVGAMAH
RAAC01621   582  FRVKDGDLAVLPTIRYVFTADLDTELPIGTVQRLVGTMHL 76795700
114844102   661  PLNKAVIDRDYGVVVEGYGLLQPRIGIDIESANATLFSKI
20517160    658  PLNRAIIDRDEGIVVEGYGLLQPRIGVDIESANASLFSKI
125973736   675  PLHRPVIDEQKGIVTEGYGLLQPRIGFDIESVNKSLFSRI
118725340   651  PLNKAYFDKEKGVVTKGYGIMQPRVDVNIESAVKSLFTRV
RAAC01621   622  PYNRPRLNARGTRVDQGYGVLQPAVAVSPRSTQASRFARL 76795700
114844102   701  YAGEGGIDPYTTAVSDVYQDLFGEGIYTGKGIYDVDVFRE
20517160    698  YGGEGGIDPYTTATSDIYQDLFGEGIYTGKGIFDVDVFRE
125973736   715  FAGEEGIDPYASAISDVYQDLFGEGIFTGKGIYDLEVFQK
118725340   691  FAGQGGIDPYTTTVSDVYQDAFGEGIFTGKGIYDVDIFTT
RAAC01621   662  WSGETGVDPYAFAISNPYQDWFGRGLFVGKGLIHVDAFHT 76795700
114844102   741  LLRDTIPDNSILSHDLLEGSFVRTGLVSDIELIDGYPAKY
20517160    738  LLKDTIPDNSILSHDLLEGSFVRTGLVTDIELIDGFPAKY
125973736   755  LLKDAIPDNTVLSHDLLEGSYVRAGLVTDIEFIDGYPSKL
118725340   731  ALDKTIPENSVLSHDLLEGSFLRTALVTDIELIDGYPAKY
RAAC01621   702  VLCDRIPDNRVLSHDILEGGFLRAGLVADVEVVESQPATL 76795700
114844102   781  NSYIMRLHRWVRGDWQLLPYLKSIKNRKGEMVKNPLSLI
20517160    778  NSYMMRLHRWVRGDWQLLPYLRSKIRNRRGELIRNPLSLI
125973736   795  NSYAMRLHRWVRGDWQLLPWLRGKTKDRKGNVIKNPLSLI
118725340   771  NSFMMRLHRWTRGDWQLLPWILG..........KNPLSML
RAAC01621   742  RAYMRRAHRWVRGDWQLTYWLRRVCRDRRGETQPVDLCGF
```

FIG 13D

```
76795700
114844102   821  TKWKIIDNLRRSVVSVALMLMLFLGFS.LLPGSSFLWLGV
20517160    818  TKWKIMDNLRRSLISISLIVMLFLGFS.ALPASALFWVAV
125973736   835  SRWKILDNLRRSIVAPSITLLIALGFS.ILPGSSLFWLGA
118725340   801  SRWKMIDNLRRSLVQPVLALIALLAVW.LFRNSYREWLIL
RAAC01621   782  TRWNIVDHVRHSLVNPALVLLMGSGMSGLLPGPAYAYGAV 76795700
114844102   860  AILTVFFPILPALVDTIFKGQFRHYWEKRHKAVITSIEAA
20517160    857  AALTVFFPVMPALFDLIFRGQLRQYLEKRHRAVITGVEVA
125973736   874  SLLTIYFPLITGTIDYIASKPLGAITSKRYKPAICGLKAS
118725340   840  ALISLCSPVLNYFVQLLIAGNYKIYIAKRRTTIITGFKAI
RAAC01621   822  LLITVFLPFLRQLESIRPG..........EWDWRSAATA 76795700
114844102   900  FYQSLLNFAFLPYQAYMMADAIVRTLTRLYITRKNLLEWV
20517160    897  FYQALLNFIFLPYNAYIMADAIIRTISRMYITKRNLLEWV
125973736   914  FLQMTLQFVFLPYNAWLMVHAAVLSLVRVLFTKRNMLEWV
118725340   880  LLQLGLLLTFLPYQAELMVNAVSKSIFRVYITKKNLLEWV
RAAC01621   851  LGQSLVMLVTLPFMAVVEADASLRALYRMLVSRRRLLEWI 76795700
114844102   940  TAADMEKRLRNDFASFFKRMWIVLVEGLALVALVMYFKPQ
20517160    937  TAADMEKRLKNDFISFVKRMWVVLLKGVVLILLTAYFKPG
125973736   954  TALDAERGLKNSLKGYVIKMKAAAFQALVVVVLAFAFKTG
118725340   920  TAADMEMSLKNGVGSYYRRMWFCPVYGAVILLLSILYRQS
RAAC01621   891  PSSHADRSDGSPAPLLYEPAGYAVALACSVPGLFGTWEQA 76795700
114844102   980  D.LIGAIVLFFLWAISPYIAFYISQPIISKEKTVSQEEM.
20517160    977  A.LIFAVGVFFLWAFSPYVAFYISQPVLLKIKFILDEDI.
125973736   994  FSAAVSVLPFAVWVSSPFIAYWISKETVYKTETLSDEEN.
118725340   960  F.VPVASLLFVLWVLSPWIAYYISVPTEKNRVVLDSAGV.
RAAC01621   931  L...SSTLALAVWLPAHAVARFLAKPAGEARVAAPDPALS 76795700
114844102  1018  EELRLIARKTWRFFEDFVTESQNYLPPDNFQEDPPNGIAE
20517160   1015  EEVRLIARKTWKFFEDTVTEAQNYLPPDNFQEDPPNGIAE
125973736  1033  LELRRIARKTWRYYEEFVNRRNNYLAPDNFQEDPPNGIAY
118725340   998  EEVRLLARRTWCYFDEFAGPEENYLPADNYQEEPYKGAAH
RAAC01621   968  AHLREVATAMWRFYERYVGEEDHHLPPDNVQFEPVERIAH 76795700
114844102  1058  RTSPTNIGLYLVSVVGARDLGYITTTEMVERIKKTLTTIG
20517160   1055  RTSPTNIGLYLVSTVGARDLGYITTSEMVDRIENTINTIK
125973736  1073  RTSPTNIGLGMLAALTARDLGYIGTLELCDIISRTMSTVE
118725340  1038  RTSPTNIGLLLVSNLAARDMGYINTLDFLARIENTISTVE
RAAC01621  1008  RTSPTNIGLYLLCVAAAADLEIIPKEGAIARLERTLATLT
```

FIG 13E

```
76795700
114844102   1098  KMEKWNGHLYNWYNTRTLEPLRPYYVSTVDSGNLVGYLIT
20517160    1095  KMEKWNGHLFNWYDTRTLKPLRPYYVSTVDSGNLVGYLIT
125973736   1113  KMEKWNGHLYNWYDTRTLETLRPRYISTVDSGNFVCYLIT
118725340   1078  KMDKWNGHLYNWYNTVTLEVLRPKFISTVDSGNFIGYLMV
RAAC01621   1048  SLDRWHGHLFNWYDTRTLRPLAPRYVSTVDSGNLVCAMLA
```

```
76795700
114844102   1138  VKEAIGEFLNKPLIDIELAKGLKDTIKMLN.........I
20517160    1135  VKEALEEFLDKPVIDLEFLRGLKDTVRMLK.........I
125973736   1153  LKEGLAEYLNRPLEDRAFIDGIRDTASLIADENENPYKDI
118725340   1118  LHEGLSGLMESPIYDFSTIEGLFDLLEICN..........
RAAC01621   1088  LGQALREWAASDADIAPRAR....................
```

```
76795700
114844102   1169  EGITEDIFRNILNKKTLMPSDWEVFLSKISEKLSSTEDEV
20517160    1166  ERIDKSLFEEFLKKGDIDPLAWKKILDDLEEVEE......
125973736   1193  SCLKECIVISEGRSYVDIPQMMKALTKLSEDGNKMKDSKD
118725340   1148  .......SEIEGSKAYFDTELLKKLTDS............
RAAC01621   1108  ........................................
```

```
76795700
114844102   1209  GNIERLKNIIGALKREMKEFLAWTEFDERQKEQE......
20517160    1200  ...ERLRDIVKKFKNEIREFMPWLEFEDAEG.........
125973736   1233  VWKAKVDSMIEMLKIELYTYMPWCDMIDELTEAFEKSEAD
118725340   1169  ......DNIEESFKNLLPAVLKLVDELDKSK.........
RAAC01621   1108  ........................................
```

```
76795700
114844102   1243  ...IFKRYKEVFEEHSSPKELEKVYKNYLLEIEEV...FE
20517160    1228  ......GYGEIFNECNSFEELKKVYEKYLEETFRA...KK
125973736   1273  IKEAFHGIIRKLNSDYSLKAMPVVYRETIKQIEKLRKKLK
118725340   1194  ...........RTGYWFKKLDSNINTFNSEYTKYRGILF
RAAC01621   1108  ........................................
```

```
76795700       1        MLKRK..................NLQSLIMI
114844102   1277  KATEEEKALLKSQKDKVARALEKIKNLEAEIENIKSIIEN
20517160    1259  EGLPEFKIKQIQR......AVEKIEELKERILKLKQEIED
125973736   1313  DGQQKNIEGLDRLKEALEGATESADKLVKRYVDLINRICR
118725340   1222  APLKNVPQELKRIQ.................QLQTKVQQ
RAAC01621   1108  ...............................RLADAMEG
```

```
76795700      14  CWLR.................................K
114844102   1317  LVEKTEFRHLYDEKRQLFSIGYNVEEEKLTKSYYDLLASE
20517160    1293  IIEKTEFKHLYDEKRQLFSIGYNVEEEKLTKSYYDLLASE
125973736   1353  IADETEFVHLYDKKKQLFSIGYNIEENSLTNSYYDLLASE
118725340   1244  LIDAMEFKYLFDPARNLFTIGFDVEDGHASKSYYDLFASE
RAAC01621   1116  FAREIDFRPLYRPDLRLFSLGFHADRNELENIVYDLLASE
```

FIG 13F

```
76795700      19 QGKQVLLLLQKEKLIKKHWFKLGRMLAIENRYKGLVSWSG
114844102   1357 ARQASFIAIAKREIDKKHWFKLGRMLAIENRYKGLVSWSG
20517160    1333 ARQASFIAIAKREVDKKHWFKLGRMLTRANRSKGLVSWSG
125973736   1393 ARQTSYIAIARGEVDQQHWFKLGRTLTQIDRYKGMVSWSG
118725340   1284 ARQTSLVAIARGEAGRQHWFKLGRKLVRVNGMKGLASWTG
RAAC01621   1156 ARQASFIAIASGQVPASHWFALSRTMTRAGRYQPLLSWSG
```

```
76795700      59 TMFEYFMPLLIMKNYQNTLLDETYAFAVRVQKNYAKELGI
114844102   1397 TMFEYFMPLLIMKNYQNTLLDETYAFAVRVQKNYAKELGI
20517160    1373 TMFEYFMPLLIMKNYENTLLDETYSFAAKVQKEYGVKLGI
125973736   1433 TMFEYFMPLLIMKSHKNTLLDETYSFVVRSQKKYGKQRNL
118725340   1324 TMFEYLMPRLLIKSYSNTLIDKTYEFVVKTQIKYGLANKA
RAAC01621   1196 TMFEYLMPALLMRHLPHTLWEETYRGVVWRQIAYARERGV
```

```
76795700      99 PWGISESGFYAFDINLNYQYKAFGVPSLGLKRGLSHDKVV
114844102   1437 PWGISESGFYAFDINLNYQYKAFGVPSLGLKRGLSHDKVV
20517160    1413 PWGISESGFYAFDMSLNYQYKAFGVPILGLKRGLSHDKVV
125973736   1473 PWGISESGFYSFDINLDYQYKAFGVPWLGLKRGLVEDMVV
118725340   1364 PWGISESCYYAFDIGLNYQYRAFGVPHLGLKRGLANDFVA
RAAC01621   1236 PFGISESGFYAFDRDLNYQYRAFGVPGLGLDRGLEQHLVV
```

```
76795700     139 APYGSLLAIGVDVEGVLQNIRFLKKEGVEGKYGFYEAIDY
114844102   1477 APYGSLLAIGVDVEGVLQNIRFLKKEGVEGKYGFYEAIDY
20517160    1453 APYGSILAISVDPEGVMKNIEFLKKEGAEGEYGLYEAIDY
125973736   1513 SPYATMLVLPLVPRDAMDNLKRLIAEGAYGHYGMYEAIDY
118725340   1404 APYATVMALDIAPQECLENIHRFKEIGAFGNFGLYEAVDF
RAAC01621   1276 APYATMLALPFAPEQVAEALRQLRELGALGPYGYYEAVDF
```

```
76795700     179 TPERFPFGKKSAIVKSFMAHHQGMAFVALDNFINNNIMQK
114844102   1517 TPERFPFGKKSAIVKSFMAHHQGMVFVALDNFINNNVMQK
20517160    1493 TPERVPFGKKNAIVKSFMAHHQGMIFVAIDNFIHENIMQK
125973736   1553 TPERIPLGEKKGIVKSYMAHHQGMSILALNNYFNDNIMQK
118725340   1444 TNSRISKDQSYAVVKCYMVHHQGMSMLALVNFFKNNIMQE
RAAC01621   1316 TASRLPPGDRYKVVQSFMAHHQGMAFIAIANYLNRNLWVE
```

```
76795700     219 RFHKDPSIKAIQILLQEKMPMYLDITREEREEARKIQKVR
114844102   1557 RFHKDPRIKAAQILLQEKMPMYLDITREEREEARKIQKVR
20517160    1533 RFHRDPRVKATQILLQEKAPIYLDMTREEREEPRKIQKIR
125973736   1593 RFHADPVVDAAKLLLMEKVPSNIVFTKENKEKILPFKDVV
118725340   1484 RFHGNPLIKAVDSLLQEKFPAAAMITKEYREQPVGGMRKN
RAAC01621   1356 RFHRLPLVRAAEYMLYERMPKRPALLLKP......VHAAH
```

```
76795700     259 KEDGDFVRVLGESKTWLPEVHILSSGRYFVMLTEKGTGYS
114844102   1597 KEDGDFVRILGESKTWLPEVHILSSGRYFVMLTEKGTGYS
20517160    1573 KEDLDFVRVLGESRSWIPEVHIVSSGKYFVMLTEKGTGYS
125973736   1633 YDEKDFLRECGMPDPVLPKAHILSNGNYSVMVTDRGTGYS
118725340   1524 VNHKDTVIREYNKLSPYPGIHLLSNGNYYLMITDKGSGYA
RAAC01621   1390 APNFDRPVYARRSGDDVAWNAVSNGSLTSFADARGEGGI
```

FIG 13G

```
76795700    299  KNNKGIFLTRWRKDLAQD.FGTFIFVQNINSNTVWSATYA
114844102  1637  KNSRGIFLTRWRKDLAQD.FGTFIFVQNINSNTVWSVTYA
20517160   1613  KNIKGIFLNRWRKDIAQD.YGTFIFIRNVDSNEVWSATFA
125973736  1673  R.WKNLDVTRWREDVTLDNYGMFFYIRDVQNDEVWTSTFA
118725340  1564  K.YHSMAVYRWINDYMQS.SGAFIYIRNLNSNEFWSTTYN
RAAC01621  1430  A.WRGIAVTRYRPDRHLPYRGPVMYVRDVDRGGVFRTTLH 76795700    338  PFYEKGQNYRVVFSADKAEYFKRVGNIDTHLEIVVSPEDD
114844102  1676  PFYEKGQNYRVVFSADKAEYFKRVGNIDTHLEIVISPEDD
20517160   1652  PFYQKGQHYRVVFSADKAEYFKRVGGIDSYLEITVSPEDD
125973736  1712  PGRKKPDEYKVEFTSGKAKYYRKDGDIDTLTEIVVCAGEN
118725340  1602  PTNTKPEAYKVIFAPHKAEFVRREGNIETNTEVIISSEDN
RAAC01621  1469  GG...GGHVEAEFRPDKSSWKRVVDGIESEWSVLVAPDRD 76795700    378  VEIRRLTLKNHSKHPRILEITSFGEISLIDLPTDVAHPAF
114844102  1716  VEIRRLTLKNHSKHPRILEVTSFGEISLIDLPTDVAHPAF
20517160   1692  VEIRRLTLKNHSKYPQILEITSFSEISLMDLPSDVAHPAF
125973736  1752  AEIRSITLANHGQESCVMEITSYFEPVLSHHGADIAHPAF
118725340  1642  TEVRRVSIHNHSSSKRIIELTSYMEVVLTQHEADSAHPAF
RAAC01621  1506  VEIRTLVLQNLGEDVRRLEVTYFAELALAKPAADIAHPSF 76795700    418  NKLFVKTEFLKEEDAILVCRKPREQGKNKLWAVHKVAVLS
114844102  1756  NKLFVKTEFLKEEDAILVCRKPREQGKNKLWAVHKVAVLS
20517160   1732  NKLFVKTEFLKDEDAIIVCRRPRDPEKSRLWALHKVVVLS
125973736  1792  GNLFIRTEFLAEHNCLIAGRRPRSEKEKPVWIMN.TVVLE
118725340  1682  SKLFVKTEYVDEYNGLLAMRRKRDDIKQTSWGYH.IASTN
RAAC01621  1546  QRLFVETGWDDARQVLWAQRRPESDDQPDVYAAFHLVAD.

76795700    458  GEIVGDTQFETDRAKFIGRGRSLKNPIALEADQPLSNTEG
114844102  1796  GEIVGDTQFETDRAKFIGRGRSLKNPIALEADQPLSNTEG
20517160   1772  GEAMGDTQFETDRLKFIGRGRSVRKPLALEPDQPLSNTEG
125973736  1831  GEGVGSLQYETDRMQFIGRGRNVSEPVALEPHRPLTNSVG
118725340  1721  GKAYGHVEYETDRSLFIGRNRNLAYPRAMEPDRPLSNSVG
RAAC01621  1585  EEAPAPVEWDSHRARFVGRGGSLAAPRGLWRRLRGE....

76795700    498  AVLDPIVSLRKRVKVMPGEVAKVVYISAITETKEKAIKIA
114844102  1836  AVLDPIVSLRKRVKVMPGEVAKVVYISAITETKEEAIKIA
20517160   1812  AVLDPIVSLRKRIRIMPGGVAKIAYISAITETKEEAVKIV
125973736  1871  AVLDPVMSFRQIVRVEPGKSVKISFVTAVANSREDVVEMA
118725340  1761  SVIDPVFSLRIRVTVEPGESTIVNFCMGACDNRKTAVEML
RAAC01621  1621  GVADPAAILRTAVTLAPGEKRALYVITALGEARDEVVETA 76795700    538  AKYKEENVVERDFEMSWTRSRVELDYLNLKPRELGLLQRM
114844102  1876  AKYKEENVVERDFEMSWTRSRVELDYLNLKPRELGLLQRM
20517160   1852  SKYKEENAIERAFEMSWTRSRVELEYINLKPRELGLFQRM
125973736  1911  TKFKSPQVIKDELGMAVTKSRVEARYLNLDTEEIELYQDM
118725340  1801  AKYSDPAAADRVIDMAWTRSIVEEGFINVDADEEKAYIKL
RAAC01621  1661  FEMRQPSARSRAAQLAWMRAQIDLRQLHLSPDDVEDAMEL
```

FIG 13H

```
76795700    578  LAHILFVSPQRRYREEMILKNVKGQSGLWAYGISDLPIV
114844102  1916  LAHILFVSPQRRYREEMILKNVKGQSGLWAYGISDLPIV
20517160   1892  LPYLIFASPQRKMREEMILKNTKGQSGLWAHGISDLPIV
125973736  1951  ISHILFISPLQRQKQKWVMNNKKGQPGLWPYGISGDIPIV
118725340  1841  LPRLIFG.IDRREQAEYILSNSLSQSDLWPFGISGDLPIV
RAAC01621  1701  LSRFLSRHAFSPERRAAILQNELGQSGLWAHGISGDRPIV
```

```
76795700    618  LVEIEKMEEIEMVKWFLKAYEYWKMKGINIDLVILNKDKS
114844102  1956  LVEIEKMEEIEMVKWFLKAYEYWKMKGINIDLVILNKDKS
20517160   1932  LLEVEKMEEIELVKWFLKAYEYWRMKGINIDLVIVNKDKS
125973736  1991  LVMLDKTDDIDIVREVLKAHEYWRLKKLAVDLVILNEEEN
118725340  1880  LVTVKSRDSFEEIDWALKLHDFYRIKGVVFDLVILLTDEE
RAAC01621  1741  AVRLASAAEVPFVAKLARLTQYLAHMGFASDLVVIDETIS
```

```
76795700    658  GYLQPLHDKIKELINTTFSYDIFGKYGGVYLLQQNNLKEE
114844102  1996  GYLQPLHDKIKELINTTFSYDIFGKYGGVYLLQQNNLKEE
20517160   1972  GYLQPLNDKIKEVINTTFAYDVFGKYGGVYLLQQENNLKED
125973736  2031  SYTNPVNSLLMDIIAESHAHDLINKPGGVFILKKSNMPPE
118725340  1920  SYIQPIFEMIRDMAVSGRSYELLDKRGGIFIRNSRQMKVE
RAAC01621  1781  SYRDEMRDRIRAEMARRGVHDAAT....LAVVKADQLSSA
```

```
76795700    698  DVYLLNTVVALKFEGGN.........ESIYDQIMIKETKN
114844102  2036  DVYLLNTVVALKFEGGN.........ESIYDQIMIKETKN
20517160   2012  DFYLLNAVAALKFDGKN.........ESIYDQIMVKVHKK
125973736  2071  DIDLICSVSRIILKGDA.........GDLKDQVKYARSIA
118725340  1960  QKNLLFASAKIILDADEGIPSLMEIIEGIEKSMDVEIHTP
RAAC01621  1817  ERALMESVAVATLRAGG.........PSVGAQLTGGRVRR
```

```
76795700    729  APKLK.....NWVKKVQNFEEIKLEELPLDYYNGFGGFSY
114844102  2067  APKLK.....NWVKKVQNFEEIKLEELPLDYYNGFGGFSY
20517160   2043  ALKPR.....SFQEKVSSCRDDGLEEIELQYYNGFGGFTP
125973736  2102  LAEFK.....QFEKKPASYDSKLAKDLELNFYNGLGGFGK
118725340  2000  LEPSEESSAPSLVSESEYSGKDVVTAAELLFFNGFGGFTK
RAAC01621  1848  EESAR..LASDRLEPEPKRAPRDAGQVEGEFANGYGAFVD
```

```
76795700    764  DGKEYIIKWE.GKSTPAPWINVISNPSFGFQVSETGAGYT
114844102  2102  DGKEYIIKWE.GKSTPAPWINVISNPSFGFQVSETGAGYT
20517160   2078  DGKEYVIKWE.GKSSPAPWINIISNPNFGFQVSEVGAGYT
125973736  2137  DGKEYVIFLENGQNTPLPWINVISNQRFGFIVTESGSGYT
118725340  2040  DGREYVIQLSDGMSTPAPWVNVIANERFGFICTESGGGYI
RAAC01621  1886  DGRAYRMRVTRAKRPPRPWSNVLANPNFGALVTELGTGYT
```

```
76795700    803  WAENSREYKLTPWYNDPVLDPHGEVIYLTDEETGDRWSIT
114844102  2141  WAENSREYKLTPWYNDPVLDPHGEVIYLTDEETGDRWSIT
20517160   2117  WAENSREYKLTPWYNDPVLDPHGEVIYLIDEITGEKWTIT
125973736  2177  WFENSRENKLTPWSNDPVSDTPGEILYVMDEHAGDVWSVT
118725340  2080  WHLNSSQNKLTSWINDPITDTPSEIIYICNTQNGKVWSCT
RAAC01621  1926  WWRNSREFKLTPWHNDAAFDPPGEAVYIADLDRGIIASAT
```

FIG 13I

```
76795700    843   PLPAGKAKVHYIKHGFGYTSFETICCGLSQHLKMFVAKED
114844102   2181  PLPAGKAKVHYIKHGFGYTSFETICCGLSQHLKMFVAKED
20517160    2157  PHPAGNSGIYYIRHGFGYSTFESASCELKSRLTMFVPKED
125973736   2217  PLPVREKEPYMIRHGFGYTVFSHASHGIEQEMVQFVPVDD
118725340   2120  PLPVREAEPYTIRHGFGYTCFGHKSNGINQTLTQFAATEA
RAAC01621   1966  PSPAGDERTYDVTHRPGVTTFESDVEGVRVTLHVFVDSAE 76795700    883   SIKINLVTIKNLGNENRKLTVSYYIRPVLGVTDEITFPYL
114844102   2221  SIKINLVTIKNLGNENRKLTVSYYIRPVLGVTDEITSPYL
20517160    2197  SVKINLIKLKNTSKNSRKIQIVYYIRPVLGVTDEATSQYI
125973736   2257  SVKISILKLKNQSQENRGLSLTYYIRPVLGVSDQFTAMHI
118725340   2160  AVKFSILKLENITTSEMLLETAYYFRPLLGTEFPQTSPYI
RAAC01621   2006  PAKWMRVRLRNQSGEERRIRVAPYAEWVLGVDPFSNTPLV 76795700    923   FTKYDEKIGALMIKNVYNEDFANRLAFLSAS..EKINSFT
114844102   2261  FTKYDEKIGALMIKNVYNEDFTNRLAFLSAS..EKINSFT
20517160    2237  ASEFDKEERILYIRNVYNEDFVNRIAFLATS..EGINSYE
125973736   2297  NTKADN..GMIVIKNNYNDEFPGRVAFIDSS..LKVNSLT
118725340   2200  VTEFDETSNAIIIDNVYSADFRGLRAFLACS..ESGVSYT
RAAC01621   2046  VVRKMGEADAIAAENRYQEAFRGALGFLAVGGAGRTTGWL 76795700    961   GDRAEFIGVASSLTLPQALEYETLSNSTGISLDPCAAIQF
114844102   2299  CDRSEFIGVASSLTSPQALEYETLSNSTGISLDPCAAIQF
20517160    2275  SERGEFIGVGFDLSSPQALSYETLSNSEGLAVDPCSAIEF
125973736   2333  CDRKEFFGAG.DIANPEGIKRTSLSGTTGAGFDPCAAISV
118725340   2238  GSRLKFFGPGMEISNPAGMR.EELDSITGAGIDACAALKA
RAAC01621   2086  GDKTRFLGDG.SYARPDALLEDAWRGGDGPTPTPCAVLAR 76795700    1001  HVEVKAKEEKQFTILLGHGKNEEEVKRLILKYTNVENCQN
114844102   2339  HVEVKAYEEKQFAILLGHGKNEEEVARLISKYTNVENCKN
20517160    2315  SVEIGPGEEKEISILLGHAKEKKEAKDLVLKYLKVENCKK
125973736   2372  SVNLKPDEEKEIIFLLGAGRDEEEARQLSAKYKKLEEAKK
118725340   2277  SIRLRPGETKEILFIVGQEKSEK.VTEVISAFRNIENAKN
RAAC01621   2125  DLDLGPHEEAEVVILLGAAPDEHEAARLAR.LADPAAADR 76795700    1041  ELQRVQEFWQELLRRIQIKTPDKSMDLLVNGWLPYQTIAC
114844102   2379  ELQRVKEFWQYLLGRIQVKTPDRSMDLLVNGWLPYQTIAC
20517160    2355  ELEKVKGFWGEILGKLTVNTPDKSLDLLVNGWLPYQTIAC
125973736   2412  ALGEVKKFWELKLGALQFETPNTAMDILLNGWLLYQVVSC
118725340   2316  EMEKVKDSWNRRLGQIQVKTPDDSINLMLNGWLQYQVLSC
RAAC01621   2164  ALREVTRFWDDLLGRVQIRTPDRAFDILMNGWLVYQALAC 76795700    1081  RLWARSAFYQSGGAYGFRDQLQDAMNMVYLEPEFTKNQIV
114844102   2419  RLWARSAFYQSGGAYGFRDQLQDAMNMVYLEPEFTKNQIV
20517160    2395  RLWARSAFYQSGGAYGFRDQLQDAMNMVLLNPEFTKRQII
125973736   2452  RLWTRSGFYQSGGAYGFRDQLQDSISLTHIWPEATRNQIL
118725340   2356  RIWARTGFYQAGGAFGFRDQLQDVMAVVYSLPELTKNQIL
RAAC01621   2204  RLWARTAFYQAGGAFGFRDQLQDALALIHARPDILRDQIL
```

FIG 13J

```
76795700    1121 NACQHQFVEGDVQHWWHPVLNKGIRTKFADDLLWLPYVTA
114844102   2459 NACQHQFVEGDVQHWWHPVLNKGIRTKFADDLLWLPYVTA
20517160    2435 NACEHQFIEGDVQHWWHPVLNKGIRTKFSDDLLWLPYVVA
125973736   2492 LHSRHQFIEGDVQHWWHEEKYKGTRTKFSDDLLWMPYATI
118725340   2396 LHCRHQFVEGDVQHWWHNQKMNGIRTRYSDDLLWLPYVTC
RAAC01621   2244 RAARHQYVEGDVQHWWHEELGKGIRTRFSDDLLWLPYAVS 76795700    1161 DYIEKTGDWPILDIEVNYLEDLRLKEEEEERYSTPRISET
114844102   2499 DYIEKTGDWPILDIEVNYLEDLRLKEEEEERYSTPRISET
20517160    2475 DYLEKTEDWAILEEKAGYLEDLPLKEEEEERYSVPSISSH
125973736   2532 EYIRITGDYDILYEETPFLEDEPLKEFEDEAYRVPRISHT
118725340   2436 DYINATGDFEILNLEERYITSPTLNENEHERYEVPSDSGL
RAAC01621   2284 RYLEATGDAALLDERAPYLVSAPLGDGELERYEDSVWSQE 76795700    1201 KGTVYEHCIRAIDYSLKFGEHGLPLMGAGDWNDGMNKVGN
114844102   2539 KGTVYEHCIRAIDYSLKFGEHGLPLMGAGDWNDGMNKVGN
20517160    2515 KGTVYEHCVKAIDYALKFGEHGLPLIGTGDWNDGMNKVGH
125973736   2572 VSTLYDHCIRAINRSLKFGEHGIPLIGSGDWNDGMNTVGN
118725340   2476 KGTVYDHCIRAIDKGLKFGIHGIPLMGGGDWNDGMNLVGV
RAAC01621   2324 EGTLAEHVARAVERALHFGDHGLPLIGIGDWNDGLSRVGA 76795700    1241 KGKGESVWLGWFLYTILQKFSPICQTKKDEEHAKKYQEIA
114844102   2579 KGKGESVWLGWFLYTILQKFSPICQTKKDEEHAKKYQEIA
20517160    2555 RGKGESVWLGWFLYTVLKKFASISEKMGDIERKEKYIKEA
125973736   2612 KGKGESVWLGWFLYSILKNFAPLCERMGDNELAKRYLDTA
118725340   2516 QGKGESIWLGWFMYCVLLRMIPICNKMGDVERAENYKTKA
RAAC01621   2364 KGRGESVWLAWFLADVVRRVAEIDHPEFAQHRAR.WLAMR 76795700    1281 NKLIKAIEENAWDGSWYRRAYFDDGTPLGSVDNSECKIDS
114844102   2619 NKLIKAIEENAWDGSWYRRAYFDDGTPLGSVDNSECKIDS
20517160    2595 ERLLKSIEENAWDGSWYKRAYFDDGTPLGSINNLECKIDS
125973736   2652 DRIVENIEKNAWDGKWYRRAYFDNGVPLGSIQNSECQIDS
118725340   2556 DAIIEAIEREAWDGSWYRRAYFDDGTPLGSMENDECKIDS
RAAC01621   2403 ERVLAAANESAWDGQWYRRAITDDGLWLGSAASPACRVDA 76795700    1321 ISQSWSVISKAGKEVRVKEAMKAVVNYLVNEEEGIIKLLT
114844102   2659 ISQSWSVISKAGKEVRVKEAMKAVVNYLVNEEEGIIKLLT
20517160    2635 ISQSWALISKGGRIERAKEAMKAVVNYLVNEEEGIIKLLT
125973736   2692 LAQSWAVISEGGDKERIAEAMSALENYLVKRDEGLIKLLT
118725340   2596 LSQSWAAITGAAKNSRVEEAMSAVEKYLVDRRNGLIKLLT
RAAC01621   2443 IAQSWAVISGGAPPDRAVRAMESFDRELVDRRLGVAHLLQ 76795700    1361 PPFDNGDLNPGYIKGYVPGVRENGGQYTHAAAWVILAFAE
114844102   2699 PPFDNGDLNPGYIKGYVPGVRENGGQYTHAAAWVILAFAE
20517160    2675 PPFDSGDLNPGYIKGYVPGVRENGGQYTHAAAWVILAFTE
125973736   2732 PPFDEGDLEPGYIKSYVPGVRENGGQYTHAAAWVVMAFAK
118725340   2636 PPFYDSELNPGYIKGYLPGVRENGGQYTHAATWVVYAFCK
RAAC01621   2483 PAFRDLRPSPGYIQGYPPGIRENGGQYTHGVIWSVIAWTR
```

FIG 13K

```
76795700   1401 LGEGDRAWQLYNMINPINHTRTPIECMKYKVEPYVMAADV
114844102  2739 LGEGDRAWQLYNMVNPINHTRTPIECMKYKVEPYVMAADV
20517160   2715 LGDGDTAWKLYNMINPINHTRTPIECMKYKVEPYVMAADV
125973736  2772 MGDGEKAMELFDLLNPINHSRTHIEYSRYKVEPYVMAADV
118725340  2676 LGDGERAWELFSMINPVNHARTKSESMTYKVEPYVMAADV
RAAC01621  2523 LGRADEAYELFSMLNPIHHADTPREVERYGNEPYVMSADV
```

```
76795700   1441 YAVEPHVGRGGWTWYTGAAGWMYRIAIENLLGLKKYGEKL
114844102  2779 YAVEPHVGRGGWTWYTGAAGWMYRIAIENLLGLKKYGEKL
20517160   2755 YAVDPHAGRGGWTWYTGAAGWMYRVAVEHILGLKKYGDKF
125973736  2812 YSVPPHTGRGGWTWYTGSAGWIYRVGFEYILGFKKRGETL
118725340  2716 YAVYPNEGRGGWTWYTGAAGWMYRIGIDHLLGIKKQGNSI
RAAC01621  2563 YTAEPNVGQGGWSWYTGAASWMYQAGLEAILGIRRHGTRL
```

```
76795700   1481 IIDPCIPKNWDKYVIEYNYKNTKYLIEVRNPEGVNKGVKE
114844102  2819 IIDPCIPKNWDKYVIEYNYKNTKYLIEVRNPEGVNKGVKE
20517160   2795 TVDPCVPRNWESFVIEYAHGHSKYVIKVINPDRVNKGVRE
125973736  2852 EIDPCIPGKWTDFTIKYRYYDTDYIIEVKNPEGVNTGVKK
118725340  2756 LLNPCIPQNMNEYSVRYVYGSSVYNITVKNPGHKNTTVER
RAAC01621  2603 LVEPCVPAHWPGFEVAYRYGSTLYRIRVERAPQG.AEARD
```

```
76795700   1521 VYIDGELVTDKTIDLTKEGNGHQVLVIMG
114844102  2859 VYIDGELVTDKTIDLTKEGNGHQVLVIMG
20517160   2835 IYLDGEPV.DKFVPLKDENKVFRVLVVMG
125973736  2892 VIVDGKVCDDGKVQLVNDKDTHKVEVYMGKK
118725340  2796 ITIDGKTTETNRIELIDDGRTHEVEAVM
RAAC01621  2642 SALTVEGVAPAEIDLVDDGQEHHVVVWLAAEGAEVLSDVQ
```

```
76795700
114844102
20517160
125973736
118725340
RAAC01621  2682 TVAARPREGARRYRMSSGARAFPASAAYRKRDPQP
```

FIG 14A

```
15616253
89099466    1                           MHFNRNVSERQEDL.
RAAC01755   1   MRWAAKRPRCSSICCRRARCHQARCCRRNSSCARRPEHFN
13470878    1                           MLSEFRLTVGGRS.
17227827    1       MTPDTLTNPDKIFLDGKTFIPADQLPIPEWPCVVSERPQ
72163378    1                           MKVWNISTGTSGEGS.
```

```
15616253    1       MDYRVIKENDVFLLTDEKGNIPENHS..YGAGLYT
89099466    15  .....MDYRVIKENDLFLLTDSKGNIPENHS..YGLGLYT
RAAC01755   41  WGRGIMHGWVIKENDLFWYGDAEGLSAHGVENVSGHGLYT
13470878    14  ................TSLLGASLSQDN...........
17227827    40  PTLTVKDDDLFLVTDTIGNISGCSLSEGNPS....MGLFC
72163378    16  ......GAVTIVEGTSFAISAGDGSMLPDHP....HGVFY
```

```
15616253    34  KDTRFLSKLDLRINGEEPILLNSEAQNAYMASILLTNPHM
89099466    48  KDTRFLSRLDIRINGEEPILLSSDADENYMAKILLTNPHM
RAAC01755   81  RDTRVLSALVWRIEPDVWVALDALAESGSESVYRYTNRPP
13470878    26  ..................VLFTTNLTN...LPIESAAGRQ
17227827    76  CDTRFLNRLELQIDGRSPVLLSSTAEKGFALSVLCTNPRI
72163378    46  DDIRIVSKWEFSVDNQALEPLTVIVHDQPYQAVFLARARR
```

```
15616253    74  EKDGDLILWRESVELERKRFIANDVVYEKIRAKNYFPKPV
89099466    88  EKDGELILWRESVEIERVRFIYEEVLYETVKLKNYFPKEI
RAAC01755   121 RADHEPP..RESLLVERRQRVDGHCFQESGIVRNFGDRAV
13470878    45  IPQ.....GAMHIERVR..LLWEERLYERITLSNYSREHS
17227827    116 DER.....MKADSVSIRRELVLNGALFEEIEVANYSTTTV
72163378    86  GGR......TSNTIFVERERRVGTGMREDITLRNMGREPA
```

```
15616253    114 TFTVNLHFDCDFQDMFVVRGFQHGDVG........KRTGQ
89099466    128 EFNFSLRADADFADMFIVRGFQNGDIG........KRTGQ
RAAC01755   159 RLAVIYEVAADFADMFEVRGFQVEAPA........RAIRS
13470878    78  TILLSLRFAADFRDMFEVRGSTRLKRG........TADTA
17227827    151 AFELSISFDADFVDLFEVRGYNRDKRGKLLRLVEPIAEDG
72163378    120 ACTVTLVVDADFADLFEVKKGEPQNDG.........HYVF
```

```
15616253    146 SVTDN.............EMRFHYEGADEIQRTTLISWD
89099466    160 TCGRQ.............NLSFHYEGADGLERRTRISWD
RAAC01755   191 RVSGN.............VCGFSYSSSDGRTWETRVQLA
13470878    110 EIAGN.............AVVLRYEGLDKVVRTSAISFS
17227827    191 LVDGDGAAVHTQHFAHKEQSLTLAYQGLDGSVMESRIQFQ
72163378    151 RSEGT..............RIIVERWWRGMQRGVIIQAD
```

```
15616253    172 QTA..........QTVSDAGYLDFTCTLGHEESQEIVLT
89099466    186 KEG..........AEVESSGEVSFRFKLQHLEEEAVTFV
RAAC01755   217 AHPSHAGEMTPVRWTESAGVGRAELLITVDAGGAAEWTLT
13470878    136 QT...........PDQLTSERADFVIAVTKRSSQTLYVE
17227827    231 HRQ..........PDDFKGYTAIWRLELPSHSTQKLGYR
72163378    176 DAT...........SVAHDRITFRAVVPERGQWSTTVL
```

FIG 14B

```
15616253   201  IAPILNG................EEP.TILPFDVALEQVK
89099466   215  IEPQTGQ................EATKEIQPAEKAKELLR
RAAC01755  257  VRPEVRGGTEFPAAGETGIGLSVSENVSSHPRGNAAEGLR
13470878   164  VGNATDDR...............PESRR.....FRAAAAR
17227827   260  VNMFTNNN...............SSSRVSAAVTLVQAKAS
72163378   203  VRPVVDGE................DLRPRFPKEQPVDESE 15616253   224  ..........ESYRAWNEGVTKVKTDHPRLQRLLDQGIT
89099466   239  ..........DSYQKWNDETTKVETDYEPLQRLVDRGID
RAAC01755  297  SRPARNAEDDASSARGWLNGAPTVS.GHEAFGRWYEQGMR
13470878   184  .........ARFGMRAKRRHGATLHSSGRVFNDWMERARA
17227827   285  .........EMMEEQNWVQKITNIRADKSIFNLVIERAEQ
72163378   227  .........PARRLREWQSNTPVVSTDNDALLAVLRRSQQ 15616253   253  DL...RVLLTDLGYGSFPVAGLPWFAVPFGRDSLIAALQM
89099466   268  DL...RVLLTDLGHGEFPVAGLPWFGVPFGRDSLIAALQM
RAAC01755  336  DI...RMLQSDFGFGPPFLVAGVPWYAVPFGRDSLIAARQI
13470878   215  DV...ALLTTELATGPYPYAGIPWFSTAFGRDGVISALQM
17227827   316  DM...YLLRQSFDKYKTVSAGVPWFSALFGRDSLITASQT
72163378   258  DVGALRIFDSRHPQRSIVAAGAPWFMALFGRDSLLTAYMA 15616253   290  LPFQPEVAKGTIRTMAAYQGTKRDPWRDEEPGKIMHELRS
89099466   305  LAFCPEVAKGTLRTMASRQGDKLDPWRDEQPGKIMHELRF
RAAC01755  373  LSAAPEVARGTLATLAHFQGERVDTERDEQPGKILHELRD
13470878   252  LWLNPGLARGVLAFLAQHQATETSPFSDSEPGKIMHETRK
17227827   353  LMLNPEIAKETLMLLAAYQGKHEDEWREEAPGKILHELRL
72163378   298  LPLDPSLALGTLQTLADRQGVEENILTEEEPGRILHESRL 15616253   330  GELANTKQVPFSPYYGTIDATPLYLMLIVEYVKWTGDTTL
89099466   345  GELANTGQIPFTPYYGTIDATPLFLMLLTEYVKWTGDITI
RAAC01755  413  GELARSGKVPFRPYYGSIDATPLFLILLADYWRFTGDTPF
13470878   292  GEMVALSELPFGRYYGGVDTTPLYIHLACAYADRTGDTAF
17227827   393  GEMARCQEIPHTPYYGTVDATPLWLMLYSEYYSWTHDRET
72163378   338  GKESGLWLGDGTVYYGTADATPLFVILLGELSRWGADPAE 15616253   370  LEELDSSIEAALRWIDKFGDRDGDGFVEYYQEAAKGIANQ
89099466   385  ADELGENIEAALNWIDEHGDRDGDLFVEYHQESSKGIANQ
RAAC01755  453  LTRMLPHAERALAWMADYGDRDGDGFIEYWREAEGGIANQ
13470878   332  IDTLWPSLCAAAEWIETASRSTG..FLTYQRAAESGLANQ
17227827   433  LEQLWPHALAAMDWIDRNMQPSG..YLTYHRKSKRGLDNQ
72163378   378  IEKLLPHADRALEWIERYGDRDGDGFVEYRRRTDQGLVNQ 15616253   410  GWKDSGDSIVHRNGDYAKTPIALAEVQGYVYQAKTGLAEL
89099466   425  GWKDSGDSIVHRNGEYAKTPIALSEVQGYVYQAKRGIASI
RAAC01755  493  GWKDSGDSMVHADGSLAQGPIALAEVQAYAYMAYVAWREI
13470878   370  GWKDSFDSVFHADGRIPKGPIALVEVQGYVFAAFQGLAKL
17227827   471  GWKDSGDCIVDRKGDLANGSIALSEVQAYVYAAKTRLAEI
72163378   418  GWKDSWDGINFADGRIAEAPIALCEVQGYVYAAYLARAYL
```

FIG 14C

```
15616253    450  YEGLNRIDLARKLSEEAQQLSERFEQAFWMEDVGFYAIAL
89099466    465  YEQLGKEAEAVKLRNQAEKLKEKFNEAFWMEDQQFYAIAL
RAAC01755   533  YRELGEPEEAERLARLADGLRSRFLQHFWLEERNEIAMAL
13470878    410  ARLRGEAERAESWEIRADAIRQKVERHFWMEDLGYYALAL
17227827    511  ARMKKRLDLFERWQEEARSLKERFNQDFWIEDQDFCALAL
72163378    458  AHQTGDDQRARYWTERAADLKKAFNERFWQPELGYYAVAL
```

```
15616253    490  DQEKKQVGTITSNPGHLLFSNMLSKERAKQVSDQLVSNKL
89099466    505  DEKKQQVGTITSNPGHTLFSGIVEGERADAVSDMLVSPKM
RAAC01755   573  DGNKRPLCVASSNMGQVLWSDILPSEVAERVAKRLLQPDL
13470878    450  DGDGLPCKVRTSNAGHLLYVGLPGPDRARMVADQLLSASF
17227827    551  DGAGKQVDSITSNPGHCLLLGIFTPERAYSVAERLRAPDM
72163378    498  DHEKKPVDACTSNMGHCLWSGIVDEDKAPYVADRLLSPTM
```

```
15616253    530  FSGYGIRTMAEGEAGYNPMSYHDGSVWPHDNSIILLGMGR
89099466    545  YSGFGVRTMGEGEAGYNPMSYHDGSIWPHDNSMILLGMSK
RAAC01755   613  FSGFGIRTLSAKELRYNPMSYHNGSVWPHDTSLVFAGLVR
13470878    490  HSGWGLRTLADDAIFFNPMSYHNGSIWPHDTAICAAGLAR
17227827    591  FNGWGIRTLSSLSPAYNPMGYHIGSVWPHDNSLIAMGLRS
72163378    538  FSGWGIRTLATDMGAYDPVSYHNGSVWPHDNAIIASGLMR
```

```
15616253    570  LGHHEQANRVINGLIDSASSFEYDRLPELFCGYEKGE..R
89099466    585  LGKTAHASQVMEGLIKASASFEYDRLPELFCGYDASRG.K
RAAC01755   653  HGAWEEAEQIFEGLMRAQAQFPHHRLPELFCGFSREESPR
13470878    530  YGSRDSVVRLMSGTFESAVHFN.MRLPELFCGFTRAAGEA
17227827    631  LGLIDQALEIFQGLLDMTSQQPYQRPPELFCGYERNGDRS
72163378    578  YGFTEHAQRVATALFEAAEHFG.YRLPELFCGFDRTDYPK
```

```
15616253    608  AVKYPVACSPQAWAAGTPLVFIQTILGLEPNVPKGKIFFS
89099466    624  AVKYPVACSPQAWAAGTPLVFIQALLGLFPDSLKEEVRMS
RAAC01755   693  PVPYPVSCSPQAWAAAVPAIVLENLLGLRPDAPRGELTIF
13470878    569  PIAYPVACLPQAWSAGSAFMLMQSCLGLQIDGWTGEIHVT
17227827    671  PVQYPVACTPQAWATGSIFQLIQMIVNLVPDAPNNCLRII
72163378    617  PVPYPTSCSPQAWAAATPIHLLRTLLRFDPWVPRGELRLA
```

```
15616253    648  .PSLPDGMKELTVENMKVGKGTISLTLKKKGQQTQLDVMS
89099466    664  .PSLLEGMNKLTVRNIKIGKGLLSLQAARTESGVKLEITE
RAAC01755   733  .PRLPASMQELKVHGLRLGRGKLSVEIARRDGCVLVDVVE
13470878    609  RPRLPIGIDNLVIRHLSVGQAVDLTFQRVGDRVGAFLAE
17227827    711  DPALPESISRLSHNLQVGTTVLDLEFERSGGTTACRVAR
72163378    657  .PSLPPGYTRLRIERLPIAGSQLTVDVTGDEVSVEGLPEG
```

```
15616253    687  NTTGLDVQCAS....VISQG
89099466    703  NTTGYQINIH
RAAC01755   772  NTTGLRVDVMDGAKEVMSAS
13470878    649  PHEGLVPLVVRS
17227827    751  .KRGNLRVVIEA
72163378    696  LRLVSEPRELDSLSLVE
```

FIG 15A

```
52081384     1  MAKLDETLMMLKELTDAKGIPANEKEPRQVMKSYIEPFAD
89098880     1  MAKLDETLTMLKELTDAKGIPGNEREVREVMKKYITEFAD
124521982    1  MAKLDETLSMLKDLTDAKGIAGNEAEVRAVVKKYIEPYAD
121533826    1      MDKTLAWLKEISEAPGVSGFEQPIRTLLTQKLSSIA.
RAAC01887    1      MHPHVEVLRDLCDAHGISGYESGVRKLFEERLRPLSE
15615819     1      MNQETQSLFKTLTELQGAPGFEHHIRRFVRGELEKYTN 52081384    41  EVTTDRLGSLIAKKTGQADGPKIMIAGHLDEVGFMVTRID
89098880    41  EVTTDGLGSLVAKKTGKEGGPKIMVAGHLDEVGFMITSID
124521982   41  ELDTDGLGSLIAKKTGQADGPKIMIAGHMDEVGFMVTQID
121533826   37  EVSSDNLGSVIFKKRGGSDTPKIMIAAHMDEIGFMVKYIT
RAAC01887   38  ELLRDRTGGVVGRKTGDPNGPKVLIAGHLDEIGFMVTHIT
15615819    39  EIVQDRLGSIFGVKRGNEQGPKVMVAGHMDEVGFMVTSIN 52081384    81  DRGYLRFQTVGGWWSQVMLAQRVTVVTKKGDITGIIGSKP
89098880    81  DKGFLRFQTVGGWWSQVMLAQRVTIVTSKGDVTGIIGSKP
124521982   81  ESGFLRFQTIGGWWSQVMLAQRVTVVTDKGDVTGVIGSKP
121533826   77  KEGFLKFTTLGGWWEQVMLGQRVTVHTTKGAIPGVIGSKP
RAAC01887   78  SEGFLKFQPIGGWWSQVVLAQRVIVQTRKGPLLGVTGSKP
15615819    79  EKGLIRFQTLGGWWSQVLLAQRVQIMTDEGPVIGVIGSTP 52081384   121  PHVLSQEARKKSVDIKDMFIDIGASSREEAME.WGVLPGD
89098880   121  PHILPPEARKKPVDIKDMFIDIGASSREEAME.WGVKPGD
124521982  121  PHILSPDARKKSYEIKDMFIDIGATSREEALE.WGVKPGD
121533826  117  PHILSPEERKKVVQKKDMYIDIGAEDEKEAKERFGVRPGN
RAAC01887  118  PHILPADERKKVVELKDVFVDIGATSKEHAEE.MGVRPGD
15615819   119  PHLLEEAQRKKPMDVKNMYIDIGADDKEDAQK.IGIKPGQ 52081384   160  QVVPYFEFTVMNNEKMLLAKAWDNRIGCAIAIDVLKNLKG
89098880   160  MAVPYFEFTVMNNEKMLLAKAWDNRIGCAIAIDVLKQLKD
124521982  160  MVVPYFEFTVMKNEKMLLAKAWDNRIGCAVVIDVLKNLHK
121533826  157  PVTPFSPFTTLANERLLMGKAWDNRIGCAIMAEVMEKLQH
RAAC01887  157  AIVPYSPFTQLGNPKMYVSKALDNRLGCATALCVLKELQG
15615819   158  QIVPICPFTPLANEKKIMAKAWDNRYGVGLAIELLKELQG 52081384   200  ADHPNVVYGVGTVQEEVGLRGAKTAAHTIKPDIAFGVDVG
89098880   200  AEHPNVVYGVGTVQEEVGLRGAKTAANLIEPDIGFGVDVG
124521982  200  ENHPNIVYGVTNVQEEVGLRGAKTAASKVKPDIAFALDVG
121533826  197  EMHANTVYGVGTVQEEVGLRGAKTSAGVIHPDIAFAVDTC
RAAC01887  197  QAHPNIVFAGATAQEEVGLRGAKTLVHLVDPDIAISIDVG
15615819   198  ETTPNILYSGATVQEEVGLRGAATSAQMIEPDIFYALDAS 52081384   240  IAGDTPGIT..EKESASKMGKGPQIILYDASMVSHKGLRD
89098880   240  IAGDTPGIS..EKEALSKMGKGPQIILYDASLVSHKGLRD
124521982  240  IAGDTPGIS..EKEALSKMGKGPQIVIYDASMVAHKGLRD
121533826  237  VAGDTPGVT..SDQASSKLGKGVAISIYDSSLIPHTGLRD
RAAC01887  237  VAGDTPGIESGERQHLGDAGKGPLLMIYDHSMIPNNRFRD
15615819   238  PANDATAGK....DAFGQLGKGALVRIYDRTMVTHRGIRD
```

FIG 15B

```
52081384    278  FVTNVADEAGIPYQFDALSGGGTDSGSIHLTANGVPALSI
89098880    278  LVTDTADEMNIPYQFDSIAGGGADSGAIHLSHNGVPSLAI
124521982   278  TVVKVAEELNIPYQFESIPGGGTDAGSIHLTGSGIPSLAI
121533826   275  FVVEVAEQNHIPYQLEFTEGGGTDAGRIHLHAQGVPSLVL
RAAC01887   277  FVLDIAATENIPVQLSSLAGGGTDAGSFHLHGIGVPSVNI
15615819    274  FVLDTAETENIPYQF.FISQGGTDAGRVHLSGNGVPSAVI 52081384    318  TIATRYIHTHAAMLHRDDYEHAVKLITEVIKRLDKETVQN
89098880    318  TIATRYIHSHAAMLHRDDYENAVKLIVEVIKRLDKETVDR
124521982   318  TIATRYIHSHAGILHRDDYENTVKLITEVIKRLDRKTVNH
121533826   315  SIPTRYIHSHNSIVHRDDYDAAVRLLVAVIKQLDQNKYQE
RAAC01887   317  GFATRYIHSHNGVVHEDDYLQAIRLVTMVKALDKDMVTE
15615819    313  GICSRYIHTAASIIHVDDYAAAKALLVKLVKTTDKAAVET 52081384    358  ITFD
89098880    358  ITFD
124521982   358  IIFD
121533826   355  LVK
RAAC01887   357  IQAW
15615819    353  ILANG
```

FIG 16A

| | | |
|---|---|---|
| 13470513 | 1 | MMTIHPLSPEDAPALAA |
| 21221842 | | |
| 13471782 | 1 | MASIESEANRN..HYAA |
| RAAC01897 | 1 | MPSLQALSVRS..MLQQ |
| 16329563 | 1 | MVYAPRPLPSRSLPVPASVSPALKKAIAQSLQGAMEAIKN |
| 15600577 | 1 | MAAKYPLSPAMWRFVEH |

| | | |
|---|---|---|
| 13470513 | 18 | MRQAASAHKGEKLGPEARPMFDAMFAATPAAADVQVEAAT |
| 21221842 | 1 | MVSRRTV |
| 13471782 | 16 | IG..ANAGKLSPQAFVEFNDSSWTALTG.EPGGVDYIEVD |
| RAAC01897 | 16 | MR...ASQNLAEQSLEVQRAGLDQMGRTIPKPENVKVERTS |
| 16329563 | 41 | IPPLEDKPAWQTLIAAYDQASQVLWQKLRQQFPVTLTKKS |
| 15600577 | 18 | SRAFASDSPRLDAQRAAYAR.MCQAFAPPRPAGLRVLDSC |

| | | |
|---|---|---|
| 13470513 | 58 | AGGIAGFWLRP......VSARSGAHILYLHGGGYVLGSAG |
| 21221842 | 8 | LGGRPALELAP......DTASGPGRLLYLHGGGYLAGSPD |
| 13471782 | 53 | AGGVPGLWVVP......KGADERRVLFYAHGGGFLGGSIY |
| RAAC01897 | 54 | FGGVPGEWIAM......ADEPTARVILYLHGGAYYMGSCE |
| 16329563 | 81 | IAGVNVYRVTPPII...SPENSQRIWVHLGGGYALAGGE |
| 15600577 | 57 | LPAAPPVRVRRYRPDRPAPPGGWPALLYLHGGGWMLGGLD |

| | | |
|---|---|---|
| 13470513 | 92 | ALTNFAGQIASRVGADTFVPDYRLAPEHPFPAAIDDAVAA |
| 21221842 | 42 | THAGLAGELARRAGLRAVSVDYRLAPEHPFPAAVDDGLAA |
| 13471782 | 87 | THRKLVGHLAKAVGCRALLYGYPLASQAKYPAQLEAAMAA |
| RAAC01897 | 88 | SHRSLAWRLAQASGSRVALIEYRLAPEHKFPATVEDAVKA |
| 16329563 | 118 | LGTGEAVLAAHYGQVGVISIDYRQPPNYPFPAALEDALVM |
| 15600577 | 97 | SHDFICADLAARLGLLVLAVDYRLAPEHPFPAALQDCLRA |

| | | |
|---|---|---|
| 13470513 | 132 | YRGL....VADGAER..IVVVGDSAGGGLTLSLLSALAAD |
| 21221842 | 82 | YREL....LSTGTDPQDLVLAGDSAGGGLG...IATLLAA |
| 13471782 | 127 | WDWL....IDQDFDTRRIALAADSCGAVLT...YGVLQRL |
| RAAC01897 | 128 | YESL....LAQGIAPDRIAIAGDSAGGGLT...MATLISL |
| 16329563 | 158 | WQEL....VKT.HDVNRLALFGTSAGGGLL...LALVCQL |
| 15600577 | 137 | WQALSLGELDEALDGRRLLVAGDSAGGNLA...AALCLAL |

| | | |
|---|---|---|
| 13470513 | 166 | KTNGMVQPVGAAVMSPWTDLALTGDSLGTRAEAD..PIFT |
| 21221842 | 115 | REAGLPQPAAVALFSPWVDLTLTGGSIRSKEGAD..PIFT |
| 13471782 | 160 | RAQERPLPAATLIISGWFDMALTAASYETNREKD..PFFA |
| RAAC01897 | 161 | RDAGKPLPACAALLSPWTDLAGTGPSMESRAAHD..PWLD |
| 16329563 | 190 | RQLNLPLPAAIAPLSPWVDLTKTGDTHFTNEYVDRTAISY |
| 15600577 | 174 | RDGGAPSPAAQILLYPLLSAAPS....PSRIDCADAPLLG |

| | | |
|---|---|---|
| 13470513 | 204 | GGVLQGFADMYLQGQDAK.NPKASPLYA.RLNGLPPIRID |
| 21221842 | 153 | EADVRAYADLYVGAGDRA.APLASPVFA.DLAGLPPLLVQ |
| 13471782 | 198 | KGGVDWLVTSFIGDYDRL.DPEVSPLYA.DLSGFPPVFLQ |
| RAAC01897 | 199 | PEGIRKAPLLYCSAEQLT.HPLVSPLYA.DLAGLPPILIH |
| 16329563 | 230 | DGLIEGLARLYAGELPLT.HPLISPIYN.DLAGLPPTLLI |
| 15600577 | 210 | LGDVQACLDAYLPLAALHRQPLALPLEAADFTGLPPAFVA |

FIG 16B

```
13470513    242  VGDDELLLADSVRYADRARAAGVEVTLSVWQGMPH..VFQ
21221842    191  AGANEVLLDDAVRLAGRAGADDVEVTLEVGPGLPH..VYQ
13471782    236  AGADETLVDESRMFAERARQAGVETRLDIFDDMLH..SFQ
RAAC01897   237  VGHDECLLDDSVRLHEKLRQAGVDARLHVWEDMWH..VFH
16329563    268  SGTRDLLLSDTARLQRKLRQNKVPVDLQLFEGLSH..AEY
15600577    250  VAEFDPLRDDGERYGAALRAAGGEAGFYPGSGLVHGCLRG 13470513    280  SSLGHFLAAERSVDAIVD.FLRQRLVGTSPSNSTASEA
21221842    229  LHYGRLEEADAALDRAAR.FLTAHLGAGHPDAGRLAPVR
13471782    274  MMAGRAPEADDAIGRLAA.WVRPRLGLPDAGDNAVSDKVA
RAAC01897   275  SFP..IPEADEALKEIGD.FMKEKIPD
16329563    306  LYEFDTPESAEVFRELSQ.FFNRHLQK
15600577    290  HGIDEVEALHEALRRAVQGFLAEDSGERQAGEESTAEHQP 13470513
21221842
13471782    313  GRAA
RAAC01897
16329563
15600577    330  GE
```

FIG 17A

| | | |
|---|---|---|
| 39654242 | 1 | MNSSLPSLRDVFANDFRIGAAVNPVTIEMQKQ |
| 61287936 | 1 | MPTEIPSLHAAYANTFKIGAAVHTRMLQSEGE |
| 3201483 | 1 | MSTEIPSLSASYANSFKIGAAVHTRMLQTEGE |
| 134266943 | 1 | MSVSQSLPSLREVFANDFRIGAAVNPVTIESQKQ |
| RAAC01917 | 1 | MTDQAPSLKEAYASRFRVGAAVNAATVHTHAH |
| 114054545 | 1 | MVGGGGMKMNSSLPSLRDVFANDFRIGAAVNPVTIEMQKQ |

| | | |
|---|---|---|
| 39654242 | 33 | LLIDHVNSITAENHMKFEHLQPEEGKFTFQEADRIVDFAC |
| 61287936 | 33 | FIAKHFNSITAENQMKFEEIHPEEDRYSFEAADQIVDFAV |
| 3201483 | 33 | FIAKHYNSVTAENQMKFEEVHPREHEYTFEAADEIVDFAV |
| 134266943 | 35 | LLISHVNSLTAENHMKFEHLQPEEGRFTFDIADRIVDFAR |
| RAAC01917 | 33 | LLARHFSSVTPENEMKWERIHPAEDTYSFSAADQIVLFAR |
| 114054545 | 41 | LLIDHVNSITAENHMKFEHLQPEEGKFTFQEADRIVDFAC |

| | | |
|---|---|---|
| 39654242 | 73 | SHRMAVRGHTLVWHNQTPDWVFQDGQGHFVSRDVLLERMK |
| 61287936 | 73 | AQGIGVRGHTLVWHNQTSKWVFEDTSGAPASRELLLSRLK |
| 3201483 | 73 | ARGIGVRGHTLVWHNQTPAWMFEDASGGTASREMMLSRLK |
| 134266943 | 75 | SHHMAVRGHTLVWHNQTPDWVFQDGQGHFISRDVLLERMK |
| RAAC01917 | 73 | DHGMFVRGHTLVWHNQTPSWVFLDSLGQPAPAKLVEARLE |
| 114054545 | 81 | SHRMAVRGHTLVWHNQTPDWVFQDGQGHFVSRDVLLERMK |

| | | |
|---|---|---|
| 39654242 | 113 | CHISTVVRRYKGKIYCWDVINEAVADEGDELLRPSKWRQI |
| 61287936 | 113 | QHIDTVVGRYKGQIYAWDVVNEAVEDKTDLFMRDTKWLEL |
| 3201483 | 113 | QHIDTVVGRYKDQIYAWDVVNEAIEDKTDLIMRDTKWLRL |
| 134266943 | 115 | SHISAVVRRYKGKVYCWDVVNEAVADEGSEWLRSSKWRQI |
| RAAC01917 | 113 | QHIAEVVGHYRGAALCWDVVNEAVIDQGDGWLRPSPWRQA |
| 114054545 | 121 | CHISTVVRRYKGKIYCWDVINEAVADEGNELLRPSKWRQI |

| | | |
|---|---|---|
| 39654242 | 153 | IGDDFMEQAFLYAYEADPDALLFYNDYNECFPEKREKIFA |
| 61287936 | 153 | VGEDYLLQAFSMAHEADPNALLFYNDYNETDPVKREKIYN |
| 3201483 | 153 | LGEDYLVQAFNMAHEADPNALLFYNDYNETDPVKREKIYN |
| 134266943 | 155 | IGDDFIEQAFLCAHEADPDALLFYNDYNECFPKKREKIYT |
| RAAC01917 | 153 | LGDDYIEMAFRLAHQADPGALLFYNDYNETKPDKRDRILR |
| 114054545 | 161 | IGDDFMEQAFLYAYEADPDALLFYNDYNECFPEKREKIFA |

| | | |
|---|---|---|
| 39654242 | 193 | LVKSLRDKGIPIHGIGMQAHWSLTRPSLDEIRAAIERYAS |
| 61287936 | 193 | LVRSLLDKGAPVHGIGLQGHWNIHGPSIEEIRMAIERYAS |
| 3201483 | 193 | LVRSLLDQGAPVHGIGMQGHWNIHGPSMDEIRQAIERYAS |
| 134266943 | 195 | LVKSLRDKGIPIHGIGMQAHWSLTRPSLDEIRAAIERYAS |
| RAAC01917 | 193 | LLEHLLDRGVPVHGVGLQMHVSLDDPPIEEMEEAIERYRA |
| 114054545 | 201 | LVKSLRDKGIPIHGIGMQAHWSLTRPSLDEIRAAIERYAS |

| | | |
|---|---|---|
| 39654242 | 233 | LGVVLHITELDVSMFEFHDRRTDLAAPT....SEMIERQA |
| 61287936 | 233 | LDVQLHVTELDMSVFRHEDRRTDLTAPT....SEMAELQE |
| 3201483 | 233 | LDVQLHVTELDLSVFRHEDQRTDLTEPT....AEMAELQQ |
| 134266943 | 235 | LDVVLHITELDVSMFEFHDHRKDLAAPT....NEMIERQA |
| RAAC01917 | 233 | LGLRLHVTELDVSVYPWVHEPDRPQAPARPYDDELAERLA |
| 114054545 | 241 | LGVVLHITELDVSMFEFHDRRTDLAAPT....SEMIERQA |

FIG 17B

```
39654242    269  ERYGQIFALFKEYRDVIQSVTFWGIADDHTWLDNFPVHGR
61287936    269  LRYEEIFNLFREYKSSITSVTFWGVADNYTWLDHFPVRGR
3201483     269  KRYEDIFGLFREYRSNITSVTFWGVADNYTWLDNFPVRGR
134266943   271  ERYEQIFTLFKEYRDVIESVTFWGMADDYTWLDHFPVQGR
RAAC01917   273  ARYEALFALYLRHQDAIDNVTLWGVADDSTWRDDFPVKGR
114054545   277  ERYGQIFALFKEYRDVIQSVTFWGIADDHTWLDNFPVHGR 39654242    309  KNWPLLFDEQHKPKPAFWRAVSV
61287936    309  KNWPFVFDQQLQPKVSFWRIINSMS
3201483     309  KNWPFVFDTELQPKDSFWRIIGQD
134266943   311  KNWPFLFDEQHEPKSAFWRVASI
RAAC01917   313  KDWPLLFDVHHRPKEAFWRVVRLAQN
114054545   317  KNWPLLFDEQHKPKPAFWRAVSV
```

FIG 18A

| | | |
|---|---|---|
| RAAC02404 | 1 | MRKLSHSGKSMAIPPRERVGMQRAVELEVDGLVLRGMEHV |
| 58338090 | 1 | MSR.ITIERDGLTLVGDR.. |
| 76796576 | 1 | MQKAVEITYNGKTLRGMMHL |
| 114845181 | 1 | MQKHVEFTYNGKTLRGMMHL |
| 15896898 | 1 | MWGKIIMQKSVEIKSKSLTLRGVLHM |
| 15806073 | 1 | MEMFAQFSVEGQRMYGMLHT |

| | | |
|---|---|---|
| RAAC02404 | 41 | P......DEAANRPVPAAILFHGFTGTHIEPHQLFVKLSR |
| 58338090 | 18 | .......EEPFGEIYDMAILMHGFTANRNTP..LLRQIAD |
| 76796576 | 21 | P......DDVKGK.VPMVIMFHGFTGNKVESHFIFVKMSR |
| 114845181 | 21 | P......DGIHGK.VPMVAIFHGFTGNKMEPHFIFVKLSR |
| 15896898 | 27 | P......LEAREK.LPIVVIYHGFCGNKMGPHFIFVKLAR |
| 15806073 | 21 | PDGSATGQQAPPQGWPSVVIVHGFTGDKVSSHRLLVLLAR |

| | | |
|---|---|---|
| RAAC02404 | 75 | ALEAEGVAAFRFDFAGSGDSDGEFQDMTASSEIRDAKAIL |
| 58338090 | 49 | NLRDENVASVRFDFNGHGESDGAFEDMTVCNEIADAQKIL |
| 76796576 | 54 | ALEKVGIGSVRFDFYGSGESDGDFSEMTFSSELEDARQIL |
| 114845181 | 54 | QLEKVGIGSVRFDFYGSGESDGDFSEMTFSGELEDARQII |
| 15896898 | 60 | ELEKLGIATIRFDFAGTGESDGEFVDMTFSNEVYDANVIL |
| 15806073 | 61 | RLTAAGIAALRFDCRGSGESQGDFSEMTVGREVQDVEAAF |

| | | |
|---|---|---|
| RAAC02404 | 115 | DWVRRDPRIDPDRVSLIGLSMGGYVASIVAGDEPDKVDRL |
| 58338090 | 89 | EYVRTDPHVR..NIFLVGHSQGGVVASMLAGLYPDIVKKV |
| 76796576 | 94 | KFVKEQPTTDPERIGLLGLSMGGAIAGIVAREYKDEIKAL |
| 114845181 | 94 | KFIKNEPMADVENIGILGLSMGGAVAGVIASELKEEIKAL |
| 15896898 | 100 | DYVKTLEFVDKDRISILGFSMGGAIASVIAGDRKDEINTL |
| 15806073 | 101 | DYVRHQPGLDPERVMLLGYSMGGLVSALAAEKVRP..HRF |

| | | |
|---|---|---|
| RAAC02404 | 155 | VLLAPAGNMADIAEK.....QAEALGAAADADVVDLGGNL |
| 58338090 | 127 | VLLAPAAQLKDDALNGD..TQGATYNPEHIPAAIPFHGKK |
| 76796576 | 134 | VLWAPAFNMPELIMHES...VKQYGAIMEQLGFVDIGGHK |
| 114845181 | 134 | ALWAPAFNMPELILEQSKSADEKMLGMLEREGIIDIGGLA |
| 15896898 | 140 | CLWAPAGNMEQIILSDT.YIGDKYDEIMEK.GIYDVEGLL |
| 15806073 | 139 | ALWSPALPELWLRHLRG.........GLLPPVISDYGGWP |

| | | |
|---|---|---|
| RAAC02404 | 190 | VGRGLYEDLKQIDAFERAKPFRGKVLIIHGMEDQAVPYEV |
| 58338090 | 165 | LGGFYLRTAQVLPIYEIAKHYTNPVSIIVGSNDQVVAPKY |
| 76796576 | 171 | LSKDFVEDISKLNIFELSKGYDKKVLIVHGTNDEAVEYKV |
| 114845181 | 174 | LSKEFIDDLIKLNIFEFSKGYDKPVLIVHGTEDAAVKYEV |
| 15896898 | 178 | LGKKFLEDIKKVNIFDRASAYNKQSLIIHGTSDEIVPLST |
| 15806073 | 170 | LGRAFLQEVVQTRPLEAAARWGGVAHVFHGDRDQTCPVEW |

| | | |
|---|---|---|
| RAAC02404 | 230 | SLKYQNEVYGERARLHLIEEADHTFNNRHWESEVIRETVR |
| 58338090 | 205 | SKKYD.EVY.ENSELHMVPDADHSFTG.QYKDSAVDLTAE |
| 76796576 | 211 | SDRILKEVYGDNATRVTIENADHTFKSLEWEKKAIEESVE |
| 114845181 | 214 | SDKILEEVYRGNAKRITIEGADHTFNKLEWEKKAIEESIN |
| 15896898 | 218 | SERYL.EMYGENTSLELVEGANHIFEKNSWENRVIDLTKK |
| 15806073 | 210 | GVRTPKPCAATPPRFPARGTRMTRSNR |

FIG 18B

```
RAAC02404    270 FLTDVDRSQ
58338090     242 FLKPLF
76796576     251 FFKKELLKG
114845181    254 FFK.ENLKG
15896898     257 YFSGKLVKF
15806073
```

FIG 19A

```
124521931    1  MKTAIVETVFGKARGYEEKGVQIWKGIPYAKPPIGPLRFR
33311865     1  MTKTIVGSVYGKLQGEQVDGVCSWKGVPYAKPPVGALRFR
134105165    1  MERTVVETRYGRLRGEMNEGVFVWKGIPYAKAPVGERRFL
56421584     1  MERTVVETRYGRLRGVVNGSVFVWKGIPYAKAPVGERRFL
138896639    1  MGTVIVETKYGRLRGGTNEGVFYWKGIPYAKAPVGERRFL
RAAC02424    1   MDVIVETRYGKVMGREEDGVRVFLGVPYAKAPQGERRFL
```

---

```
124521931   41  PPELPEPWAGVKDCTQFGPIAWQPPVELMD.FLGNPAENM
33311865    41  APERPDSWEGVRQATSFSPVAPQTQREIME.FFGNDISNM
134105165   41  PPEPPDAWDGVREATSFGPVVMQPSDPIFSGLLGRMSEAP
56421584    41  PPEPPDAWDGVREAAAFGPVVMQPSDPIFSGLLGRMSEAP
138896639   41  PPEPPDAWDGVREATSFGPVVMQPSDSMFSQLLGRMNEPM
RAAC02424   40  PPEPVEPWADVLDARAHGPICPQVANPLNP....VDGFVQ
```

---

```
124521931   80  DEDCLNLNIWTPGADGERRPVMVWIHGGAFANGAGSAPSY
33311865    80  NEDCLYLNVWSPGADDKKRPVMVWIHGGAFVSGSGSSSWY
134105165   81  SEDGLYLNIWSPAADGKKRPVLFWIHGGAFLFGSGSSPWY
56421584    81  SEDGLYLNIWSPAADGKKRPVLFWIHGGAFLFGSGSSPWY
138896639   81  SEDGLYLNIWSPAADGKKRPVLFWIHGGAFLFGSGSFPWY
RAAC02424   76  SEDCLRLNIYAP.AEGTGHPVMVWIHGGAFVFGSGQSPWY
```

---

```
124521931  120  DGSAFAKNGDVVVVTINYRLGALGFLYLGEMGG.EYEASG
33311865   120  DGASFAAQGDVVVVTINYRLGILGFLHLGEIGGEEYATSG
134105165  121  DGTAFAKHGDVVVVTINYRMNVFGFLHLGDSFGEAYAQAG
56421584   121  DGTALAKHGDVVVVTINYRMNVFGFLHLGDLFGEAYAQAG
138896639  121  DGTAFAKHGDVVVVTINYRMSVFGFLYLGDAFGETYAQAG
RAAC02424  115  DGRAFARDG.VVLVSINYRLGPLGFLHLAHLGGEAYASSG
```

---

```
124521931  159  NCGILDQIAALKWVKENIAAFGGDPDCVTIFGESAGAMSV
33311865   160  NCGILDQVAALQWVQENIASFGGDPNNVTVFGESAGAMSI
134105165  161  NLGILDQVAALRWVKENIAAFGGDPDNITIFGESAGAASV
56421584   161  NLGILDQVAALRWVKENIEAFGGDPDNITIFGESAGAASV
138896639  161  NLGILDQVAALRWVKENIEAFGGDPDNITIFGESAGAASV
RAAC02424  154  NAGILDQVAALTFVRDTIEAFGGDPNRVTVAGESAGAWSV
```

---

```
124521931  199  AALLSSPAASGLFHKAILESG.AANFTATPERAAKNARRI
33311865   200  GVLLGFPSAQGLFHNAILQSG.AAANVHSSETATKVAGHL
134105165  201  GVLLSLPEASGLFRRAMLQSGSGSLLLRSPETAMAMTERI
56421584   201  GVLLSLSEASGLFRRAILQSGSGALLLRSPKTAMAMTERI
138896639  201  GVLLSLPEASGLFRRAILQSGSGSLLLRSPETAMALTERI
RAAC02424  194  GTLLVMESARGLFQQAILQSG.IPFAYRTPEFAEWWTTQL
```

---

```
124521931  238  LETLGLEKKDVAKLAEVPAKNLAEAVNSL...PFMSLLPV
33311865   239  LAALQVEPTNLSKLEELSVEQLIQVADLV...PPMSLGPV
134105165  241  LDKAGIRPGDRERLLSIPAEELLRAALSLG..PGVMYGPV
56421584   241  LERAGIRPGDRGRLLSIPAEELLRSALSLG..PGIMYGPV
138896639  241  LERAGIRPGDRDRLLSIPAAELLQAAMSLG..PGITYGPV
RAAC02424  233  LDALGINQASWHRLFDVPAADLVAAAARIPARDGLNLRPV
```

FIG 19B

```
124521931   275  TDGIVLPEHPERALEN.AAKDIPVLIGTNKDEYRLFTVFD
33311865    276  IDGVSLPKHPQEAIADGSAKDVSILVGTNKDEYNIFSVFD
134105165   279  VDGRVLRRHPIEALRYGAASGIPILIGVTKDEYNLFTLTD
56421584    279  VDGRVLRRHPIEALCDGAASGIPILIGVTKDEYNLFTLTD
138896639   279  VDGHVLRRHPIEALHDGAASDIPILIGVTKDEYNLFSLTD
RAAC02424   273  LDGVTLTRSFWDALREGQAAHVPTLAGSNREELMLWMARD
```

```
124521931   314  PVWKRQDPKEMQDVFQKTFAKYWDALS...AKITDPSAFT
33311865    316  PEWKNADEAKVTALFEKTFGPLVQVIS...KFIPG..GLN
134105165   319  PSWTKLGEKELLDRINREVGPVPEEAIRYYKETAEPSAPT
56421584    319  PSWMKLGEHELLDRINREVGPVPEAAIRYYAETAEPSAPD
138896639   319  PSLTRLEEKELLDRMNREVGPIPEEAVRYYAETADRSAPA
RAAC02424   313  PEWRTLSDEERIARVDRMWGPLGDRAR..DYYVDGRTGDE
```

```
124521931   351  QELYDR.IMTYFVFTGPALKLADTRAQTGEKVWMYQFDWE
33311865    351  QDLFNK.LLTDTIFTNPAQKLAELQVNQGTPVWMYRFDWE
134105165   359  WQTWLR.IMTYRVFVEGMLRTADAQAAQGADVYMYRFDYE
56421584    359  WQTWLR.IMTYRVFVEGMLRTADAQAAHGADVYMYRFDYE
138896639   359  WQTWLR.IMTYLVFVDGMLRTADAQAAQGANVYMYRFDYE
RAAC02424   351  LETWLVRFASMRSFTYPTIRAAEIQSEY.APVYLYRFDYR
```

```
124521931   390  SPVYNGTLKACHALEIPFVWHTLEQPGTENLTGNAPGRHA
33311865    390  TPVFGGALKSTHALEIPFVFNTLRTPNTENFTGSSPERQQ
134105165   398  TPVFGGQLKACHALELPFVFHNLHQPGVANFVGNRPEREA
56421584    398  TPVFGGQLKACHALELPFVFHNLHQPGVANFVGNRPEREA
138896639   398  TPAFGGQLKACHTLELPFVFHNLHQPGVENFVGNRPEREA
RAAC02424   390  P....SQLGAAHALEIPFVFGTYAHPSARVLVGDRPSHAA
```

```
124521931   430  LADQMHQAWIAFAQNGDPNCSLLPE.WPPYNTRQRPAMIF
33311865    430  IADQMHQRWINFAKSGHPNSDRLLE.WPSYDMNNRSTMIF
134105165   438  IANEMHYAWLSFARTGDPNGAHLPEAWPAYTNERKAAFVF
56421584    438  IANEMHYAWLSFARTGDPNGAHLPEKWPIYTNERKPVFVF
138896639   438  IASEMHGAWLSFARTGNPNGAHLPEKWPVYTKEHKPVFVF
RAAC02424   426  VSDAMHAAWVAFVRHGSPQAPHLPE.WPTYDPKRRSTMIF
```

```
124521931   469  GQDCRVEKDPHQAERALWGGLGE
33311865    469  NNESIVVNDPNREDRLKWEQLSMVMKG
134105165   478  SAASHVEDDPFGRERAAWQGR
56421584    478  SAASHVEDDPFGCERAAWMTRA
138896639   478  SAASHVEDDPFGREREAWQGRL
RAAC02424   465  DETSRVEEDPDTAERELWSEMMSLSM
```

FIG 20A

```
29377189     1            MKTWENYKVDSINRLPGRAHFSSFPSK
116493950    1            MTTAKLWEKPELTDINRMAPRSHFQTFFP.
40745013     1  MASLSAVSGWPTYLPDWSNLNVLHRNTLPPRAHFYSYPNE
RAAC02616    1  MEVMRVEQKYVESFYPPSDY......RLPPRAFFIPHSTE
49176308     1            MNRWENIQLTHENRLAPRAYFFSYDSV
```

```
29377189    28  ETALL..NENKYTQAYKNLNGCWHFLFLEAPEYSPENFFAT
116493950   30  ......GENRQPRHYQLLNGTWQFKFLDAPEYAPEDFMAV
40745013    41  EAALT..FNRDEGLFQSLNGTWKFHYDASPFEAP...IWN
RAAC02616   35  REALARGFYRASTQVLPLEGKWKFRLFDNPRAVPTDVTWI
49176308    28  AQART.FARETSSLFLPLSGQWNFHFFDHPLQVPEAFTSE
```

```
29377189    67  DFDTSQMDQITVPGNWQVQGYGKMHYSDLWYNFPINPPYV
116493950   64  DFNDQDWDQIPVPSNWQLQGYGKMHYSDLWYNFPINPPFV
40745013    76  TANTTEWDDIIVPGVWQMQGYGRPQYTNIHYPIPVTPPNV
RAAC02616   75  DFDDSSWEEIHVPSNWQMEGYGRPHYTNVMYPFPVDPPRV
49176308    67  LMAD..WGHITVPAMWQMEGHGKLQYTDEGFPFPIDVPFV
```

```
29377189   107  PTENPTGIYKRTFAIDETFHDKKIILRFCGVDSAYHVWVN
116493950  104  PSENPTGLYRRTFTVDEVAVNEQYIIGFDGADSAFKLYLN
40745013   116  SYMNPTGSYWREFDVPADWDGQQIRLRYEGVDSAFHVWVN
RAAC02616  115  PSENPTGCYRTKFFLTHHDVG.RVHLRFEGVDGLYQVYVN
49176308   105  PSDNPTGAYQRIFTLSDGWQGKQTLIKFDGVETYFEVYVN
```

```
29377189   147  GHEVGYSKGARNEAEFDITPYAKIGETNDLTVRVYQWSDG
116493950  144  GDFIGCSKGARLPSEFDVTKALKQG.TNTIAVEVVQWSDG
40745013   156  GEEVGYSQGSRNPSEFDITGYLSSEGTNTLATRVYQWSDG
RAAC02616  154  GHDIGFGYGSRLPSEFDITDFVHA.GDNVLVVVVCQWSAQ
49176308   145  GQYVGFSKGSRLTAEFDISAMVKTG.DNLLCVRVMQWADS
```

```
29377189   187  TYLEDQDMWWLSGIFRDVELLGVPENGLEDFFIISDLDDS
116493950  183  TYLEDQDMWWLSGLFRDVSLYSRPQNGLYDVRVRTYLLKD
40745013   196  TYLEDQDQWWLSGIFRDVYLVPFPSSAITDFFIQPEVDDG
RAAC02616  193  SYLEDQDMWWLSGIFRDVYILKRPQIYLSDVRVRALLGTD
49176308   184  TYVEDQDMWWSAGIFRDVYLVGKHLTHINDFTVRTDFDEA
```

```
29377189   227  YQNGHLAITGKFWQDKGQQ....VQLELMD...QQGKTVL
116493950  223  YRAGELVVTPTLSGAVPSK....IHYELT....KDGATLI
40745013   236  FASGTLKVNVTIQGEHGN.....LSVKVLS...PGGN.VV
RAAC02616  233  GRTGCLHVEVEIGGILSRDKPVPLRFKLID...SIGDSEI
49176308   224  YCDATLSCEVVLENLAASPVVTTLEYTLFDGERVVHSSAI
```

```
29377189   260  KETVAGNQGTVEFSASLPSVTAWSAEKPYLQLFITVFSE
116493950  255  DQTLSTD...VSLDVTLNDIQAWSAEAPNLYDLTMTVLQN
40745013   267  DEWTGSSSTIYSKDIKGDDFLLWSAETPNLYTVLIEFN..
RAAC02616  270  LENTMLSDGFATYEAEIPNVRPWTAETPNLYTLLVSIDPD
49176308   264  DHLAIEKLTSASFAFTVEQPQQWSAESPYLYHLVMTLKDA
```

FIG 20B

```
29377189    300  .GEVVEVIPQKVGFRNIHVSGETFLVNGVAIKLKGMNRHD
116493950   292  .DAPLEVVRQRIGFRQIELNGKTFLVNGKAIKFKGVNMHD
40745013    305  ....GRTISQKVGFRRVEMSGSNFLVNGQPIIIYGVNRHE
RAAC02616   310  .SLYAEHVALQVGFRRIEIADGQLKINGVPIVLKGVNRHE
49176308    304  NGNVLEVVPQRVGFRDIKVRDGLFWINNRYVMLHGVNRHD
```

```
29377189    339  YNPKNGRVVSREEIEKDIRLMKQFNINAIRTSHYPASAYF
116493950   331  YSATEGRVMSEADFKKNIISMKRNNINAIRTAHYPKAPYF
40745013    341  HNYTSGRTVPYESMRADLIRMKQSNINAIRTAHYPQHPSF
RAAC02616   349  HDARLGRALTLDVMIRDVQMMKQNNINAVRTSHYPHHPVF
49176308    344  NDHRKGRAVGMDRVEKDLQLMKQHNINSVRTAHYPNDPRF
```

```
29377189    379  YDLCDEYGMYVIDETDLECHGFELTGEYDW.....ISNDP
116493950   371  YDLCDELGMYVIDETDLECHGFELTERYDW.....ITDDP
40745013    381  YDVADELGFYVITEADLECHGFRDIAGSEENAAAWTSDNP
RAAC02616   389  YDLCDRYGLYVLDEADLECHGFALTGNWDR.....LSDDP
49176308    384  YELCDIYGLFVMAETDVESHGFANVGDISR.....ITDDP
```

```
29377189    414  EWETAYVSRMVRMIQRDKNHPSILFWSLGNESAFGHNFIE
116493950   406  RWKTAYVDRMRRTLQRDKNHPAIIMWSLGNESDFGDNFRA
40745013    421  EWTHAYLDRAEQLVERYKNHPSVIMWSLGNECQYGQNQAA
RAAC02616   424  QLEQAYVDRLERMICRDRNHACVIMWSLGNESGYGRNHRA
49176308    419  QWEKVYVERIVRHIHAQKNHPSIIIWSLGNESGYGCNIRA
```

```
29377189    454  MARIAKEMDPTRLVHYEGDFE..........AEVTDVYST
116493950   446  MAAYCKAEDPTRLVHYEGDFE..........AEVSDVYST
40745013    461  MYKWIKERDPSRLVHYEQDHN..........AETADIYSQ
RAAC02616   464  MAERARAIDPTRPVHYEGETRRLLELGSDLQHAVMDVYST
49176308    459  MYHAAKALDDTRLVHYEEDRD..........AEVVDIIST
```

```
29377189    484  MYTWLEHPTRELLMNTIIENSKKPHILCEYCHAMGNGPGN
116493950   476  MYTWLEHDT.KMTMADVLQKTQKPHILCEYAHSMGNGPGN
40745013    491  MYS.....SPDTMLEHMANHTDKPLILCEFAHAMGNGPGG
RAAC02616   504  MYT.....SVDELSRLGELELPKPHILCEFAHAMGNGPGG
49176308    489  MYT.....RVPLMNEFGEYPHPKPRIICEYAHAMGNGPGG
```

```
29377189    524  LKEYQELFYAHDKLQGGFIWEWFDHGIESVTDNGEVYYRY
116493950   515  LKEYQDLFYGHQQLQGGFIWEWFDQGVAAQQGD.QTYYRY
40745013    526  LKEYIELFRSHPLSQGGLVWEFNNHGLLKKEGD.LEYYAY
RAAC02616   539  LKEYVELFYQQRRLQGGFVWEWIDHGILAYTSDGRPYFAY
49176308    524  LTEYQNVFYKHDCIQGHYVWEWCDHGIQAQDDHGNVWYKF
```

```
29377189    564  GGDFGDDPSNKDFCIDGMLMPDRTPSPSLYEYKKVIEPIT
116493950   554  GGDFGDQPNNSNFCIDGLIRPDGQPSTALTEVKKTFEPFQ
40745013    565  GGDFGDEPNDADFVMDGLTLSDHTPMPSLLEYAKIIQPVS
RAAC02616   579  GGDFGDVPNDLNFVIDGLLFPDRTPSPGLFEYKKAIEPVR
49176308    564  GGDYGDYPNNYNFCLDGLIYSDQTPGPGLKEYKQVIAPVK
```

FIG 20C

| | | |
|---|---|---|
| 29377189 | 604 | TSAIDVLSGEFSLLSRFDFENLAIFKLVYTITEDQTVIQS |
| 116493950 | 594 | MTVRDLPTQTITVTNRLDFLSSDQFNFGYELEADGKLMAT |
| 40745013 | 605 | VNLTDDSS.SMVITNHYAFVDLSGLDVSWHIVQDGETTEA |
| RAAC02616 | 619 | VLEFDRSSGIIKVQNRYDFLCLDCLVAEWSLQDEQSVLAG |
| 49176308 | 604 | IHARDLTRGELKVENKLWFTTLDDYTLHAEVRAEGETLAT |

| | | |
|---|---|---|
| 29377189 | 644 | GTVAVPAIAARAEGRLHLPYHLDFPKKAGAAYYLTLSYQL |
| 116493950 | 634 | GKIDLPTIMAGTTKTIKLDIELP.KLDPEVIYNLHVLTEL |
| 40745013 | 644 | QELDLPPVP...AGESRTVDLPLDPSSLSKETWLTIEFKL |
| RAAC02616 | 659 | GILELEPVPPRSIGQIRVPCAEILNRHRDRCLTLTVRFLL |
| 49176308 | 644 | QQIKLRDVAP....NSEAPLQITLPQLDAREAFLNITVTK |

| | | |
|---|---|---|
| 29377189 | 684 | KETTAYASAGHELATAQFELPIA.........TPGIEITP |
| 116493950 | 673 | KNQTSWADAGTVLSQTVVNLQRP.........QHHMTHQQ |
| 40745013 | 681 | KEDKAWAVRGHVVAWDQLYFPGSSASTSSSKRSTPISRQT |
| RAAC02616 | 699 | RHPTDYAPAFHEVASFCEYVERSCQNAS.....IDIYRPV |
| 49176308 | 680 | DSRTRYSEAGHPIATYQFPLKENTAQP......VPFAPNN |

| | | |
|---|---|---|
| 29377189 | 715 | VGSLMAKEIGPHLYIEGPNFSINFDKVKGALTNVTRDGKK |
| 116493950 | 704 | TTALQASENATTIMVTGGQNEYRFDKIKGTFS.LTHDGHK |
| 40745013 | 721 | SGGLEVKQNQTSLRIITGTSIFGFNLIQGNVTWEAN.GAS |
| RAAC02616 | 734 | TR.FEIVEKGSSLCIYDDSFSVEFDLLRGRISGVGYRGSQ |
| 49176308 | 714 | ARPLTLEDDRLSCTVRGYNFAITFSKMSGKPTSWQVNGES |

| | | |
|---|---|---|
| 29377189 | 755 | LLHKGPKFTFWRAPISND......MEIIDEMKKKYFLHLE |
| 116493950 | 743 | LIADGIKMNFWRAPIDND......MYLLDDYYNKYFLNLW |
| 40745013 | 760 | LFQRGPELSFIRAMTQNDEGQS....GNEAEWDDAWVGTM |
| RAAC02616 | 773 | IIMSPLSMSFWRAPTDNDDPPNREMFSVAKVWRDYGVDRL |
| 49176308 | 754 | LLTREPKINFFKPMIDNH......KQEYEGLWQPNHLQIM |

| | | |
|---|---|---|
| 29377189 | 789 | HEIVRSFEWKKVD..DFIQVIVKTINGTTNSAWHYQCTYQ |
| 116493950 | 777 | HESTREVQLHPQTNGDYVVNLTKQVG.TTNSGWYYLIQQQ |
| 40745013 | 796 | HTQVRDVTWRSSD..TEAIVHFKVRVAPQVLEWGVEADLI |
| RAAC02616 | 813 | SESVSNIEIKKHD..NVVRALVESRVAPAGLSWGMALQYE |
| 49176308 | 788 | QEHLRDFAVEQSD..GEVLIISRTVIAPPVFDFGMRCTYI |

| | | |
|---|---|---|
| 29377189 | 827 | YLIAPNG...EIFFDLKGSPAGKIENAPDMLPRLGVTLHL |
| 116493950 | 816 | YTMHQDG...SFDLDVIGKASGKRDMAPEMLPRIGVKMTL |
| 40745013 | 834 | YTISTEDSVPTLHIHATGEFVG..TNTPSVVPRIGLQTIL |
| RAAC02616 | 851 | YIFLRGG...LVMVRICGKPEG..AYPP.TLPRIGLLTTI |
| 49176308 | 826 | WRIAADG...QVNVALSGERYG...DYPHIIPCIGFTMGI |

| | | |
|---|---|---|
| 29377189 | 864 | DKSLSEVKYFGKGPRENYVDSQEAGLLGVYDATVAEMFTN |
| 116493950 | 853 | PKAYQQVSYDGLGPTENYSDSHQAAYYSHFTSSVDDLFVN |
| 40745013 | 872 | PSSFNFVRWLGRGPGENYKDSQACRIGEYSATVEELFTH |
| RAAC02616 | 885 | HLDFEYVSWFGRGPGESYRDSKESQLIGRYRRLADELYTP |
| 49176308 | 860 | NGEYDQVAYYGRGPGENYADSQQANIIDIWRSTVDAMFEN |

FIG 20D

```
29377189    904  YVVPQANGNHMATKWSAFTD..........DRGQGVVATA
116493950   893  YVKPQENGNHMDTDQIALTD..........GQDQ.LTVTM
40745013    912  YDYPQENGNREDLRWLQISDPGTGVTLDARRADASTNQTA
RAAC02616   925  YVYPQENGNRTDVYWISITN..........KYMEGLFITG
49176308    900  YPFPQNNGNRQHVRWTALTN..........RHGNGLLVVP 29377189    934  ADSYNFSVSYFEEQALDVAKHTNELQESEYVVLNIDYKQN
116493950   922  AKPLNFSVSNYADETLEAAKHTIDLKKSDALNLYLDFRQN
40745013    952  VEVFSFTASQYMPIDLNNAKHPFDLKPLDMTILWLDYDNH
RAAC02616   955  PQPLNFQVSRFSVEDLERARHPYELEESPWRYLRIDFSHH
49176308    930  QRPINFSAWHYTQENIHAAQHCNELQRSDDITLNLDHQLL 29377189    974  ALGSYSCGQWQLEKYRTTFEEFQLAFRLTPFNNKEIQAAD
116493950   962  GLGTNSCGQNQLKRHRCKFDDFELGFNFKVN
40745013    992  GLGSASVGPQPFEQYRCKTEPFDFAFELSLLS
RAAC02616   995  GLGSASCGPGPLPEHQLRTEPFEWTLCFAPLARHEIDESI
49176308    970  GLGSNSWGSEVLDSWRVWFRDFSYGFTLLPVSGGEATAQS 29377189   1014  VAHERVKRPTIS
116493950
40745013
RAAC02616  1035  LHQVVTERLKFI
49176308   1010  LASYEFGAGFFSTNLHSENKQ
```

FIG 21A

```
15642830    1                    MDYRMCWLEYRGLP.ADVAGKLK
148270004   1                    MDYRMCWLEYRGLP.ADVAKKLK
15613624    1        MNR........GETGYETWLRYEEITDSALHTQYR
118725970   1        MYKSNVNDELYGANGYNCWLGYHLLENGELRENYS
RAAC02661   1              MTNIPEGDLDYRAWLQESPLPRAVPEAARR
116621784   1 MSFKFLALLLTIPAVHAETGYDAWLRYAPLSDAAARPYLT 15642830   23 DWFSSVSILEPGS..SVLKDEIRRFSERSIGITPRFYSRP
148270004  23 DWFSSVSILEPGS..SVLKDEIRRFSERSIGITPGFYSRP
15613624   28 AYFQTIEIKGNSPIIESAKEELMQGLRSLLGVTPKCLSAT
118725970  36 QWASNIVISKEPDEIKIALSELKSGINGILGVDAVVVTRE
RAAC02661  31 ...MAVYGPADDPLLCTAAAEWGRAVRAACGESPARLARD
116621784  41 ALPAAVTVYGASPVVQSAQRELLRGVRGMLGRTLRMESKL 15642830   61 LKKE...KYIMVGRLESLP......IKLD..VNLGEEGFM
148270004  61 LKKE...KYIMVGRLESLP......IKFD..ENLGEEGFM
15613624   68 GEQA...SCL.IGTIADVAE.VSQAIK....ERLREEGYA
118725970  76 PEQS...SCIALGVLGRGQN.IDSYVKYDEVVQIGNEGFI
RAAC02661  68 PGGAPSVPCVAMGLLSAMPRGLREAAQAALAGAPSDEAYA
116621784  81 PAER....AILLGTAGDLQA...AIPQLHLPPDLPADSYL 15642830   90 LRTIEWNGSKILLVTGETKKALVYGIFDLMKRIRLGEDIE
148270004  90 LRTLEWNGSKILLVTGETKKALVYGIFDLMKIIRLGEDIE
15613624   99 IYSEKGR....LVLVGKTETGVLYGTFHLLRLLQMRDHLH
118725970 112 IKAFKTGNSEIVVVAGTTTKGLLYGVFSLLRLLQTEATIS
RAAC02661 108 ILPVDGQG...VAVVSRTPAGVLYGVFHLIRRLRLGEPLH
116621784 114 VTTVTANGAPHLVIAGANDRAVLYGVFALLRKIGTGQTLN 15642830  130 KMNVLAKPKAKFRMLNHWDNLDGTIERGYAGNSIFFKDNR
148270004 130 KMNVLEKPKAKFRMLNHCDNLDGTIERGYAGNSIFFKDNR
15613624  135 DLRIVENPRNQLRMINEWDNMDGSIERGYAGGSIFFEHNK
118725970 152 GILKIENPANQLRIINHWDNIDGSIERGYAGKSIFFTDNK
RAAC02661 145 EP.CVSSPKNAWRMLDHWDNADGTIERGYAGKSLFYRGGQ
116621784 154 DDDPVQTPYAPVRWVNEWNNLDGTIERGYGGRSIFWDNNR 15642830  170 IIIN.QRTKDYARLLASIGINGVVINNVNVKKREVYLIDS
148270004 170 IIIN.QRTKDYARLLASIGINGVVINNVNVKKREVYLIDS
15613624  175 VTNNLQRIKDYARILSSIGINAIAFNNVNVHEEETKLITR
118725970 192 VTEDLGRIKDYARLLCSVGINSIVINNVNVHKYESMLITD
RAAC02661 184 IDFDEGRVRDYARLLASVGVNAIAINNVNVHETETRFLTE
116621784 194 ARADLTRVADYGRMLASLGIQACSINNVNAN...PRVLAS 15642830  209 IYLKKLKKLADIFREYGIKIYLSINFASPVYLGGLDTADP
148270004  209 IYLKRLKKLADIFREYGIKIYLSINFASPVYLRGLDTADP
15613624  215 KFLPDVAKVANIFRQYGIKTFLSINYASPIQLGKLETADP
118725970 232 KYLNDVASLAQIFRDYGIKLYLSANFASTIEIGGLATADP
RAAC02661 224 AHLPGVARLADVFRPYGIRVFLSINFASPVDLGDLPTADP
116621784 231 DFLPEIVRIAEAFRPWGIRVALAVDFGSPKTIGGLDTFDP
```

FIG 21B

```
15642830    249  LDERVARWWREKARGIYDYIPDFGGFLVKADSEFNPGPHM
148270004   249  LDERVAHWWREKAREIYDHIPDFGGFLVKADSEFNPGPHM
15613624    255  LDEKVRAWWKETVADIYRYIPDFGGFLVKADSEHRPGPFT
118725970   272  LDPQVRKWWKEKADEIYSLIPDFGGFLIKADSEFRPGPFT
RAAC02661   264  LDPRVEDWWRATADRIYRHIPDFGGFLVKADSEFRPGPFT
116621784   271  VDPKVAAWWKSKIDELYRAVPDLAGIVLKADSEGRVGPST 15642830    289  FGRTHAEGANMLARALAPFGGVVIWRAFVYNCLQDWRDYK
148270004   289  FGRTHAEGANMLARALAPFGGVVIWRAFVYNCLQDWRDYK
15613624    295  YGRNHAEGANMLAEALAPFGGIVLWRCFVYNCLQDWRDRK
118725970   312  YGRTHADGANMLAEALEPYGGLVIWRCFVYNCMQDWRDRI
RAAC02661   304  YGRDHADGANMLARALAPHGGVVIWRAFVYNCLMDWRDRR
116621784   311  YGRTHADAANVVARGLQPHGGLLFYRGFVYDHHMDWKNPK 15642830    329  TDRAKAAYDNFKPLDGQFDDNVIIQIKYGPMDFQVREPVN
148270004   329  TDRAKAAYDNFKPLDGQFDDNVIIQIKYGPMDFQVREPVN
15613624    335  TDRARAAYDHFKPLDGLFHDNVVLQIKNGPMDFQVREPVS
118725970   352  TDRARAAYDNFMPLDGLFRENVLLQIKNGPMDFQVREPVS
RAAC02661   344  ADRARAAYDHFVPLDGRFLDNVLIQIKNGPMDFQVREPVS
116621784   351  NDRGRAAYDNFQPLDGKFDANVIVQIKHGPIDFQVREPAS 15642830    369  PLFGGMEKTNQILELQITQEYTGQQIHLCFLGTLWKEILE
148270004   369  PLFGGMERTNQILELQITQEYTGQQIHLCFLGNLWKEILE
15613624    375  PLFGAMPKTNQMLEFQITQEYTGQQKHLCYLVPQWKEILD
118725970   392  PLFGGLQKTNQLLELQITQEYTGQQKHLCYLVPMWKEILD
RAAC02661   384  PLFGGLSATNVMLEFQITQEYTGQQRHVCYLAPMWKEVLD
116621784   391  PLFAALEKTNQAIELQITQEYFGQSRHNVFLVPMWKTALD 15642830    409  FDTFAKGEGSYVKRIVDGTLFDRENNGFAGVSNVGDSVNW
148270004   409  FDTFAKGEGSYVKRIVDGTLFDRKNNGFAGVSNVGDSVNW
15613624    415  FDTFANGKESPVKSIVDGSQYDYKVSGITAVSNVGNDENW
118725970   432  FDTMAKGRNTSVKKIITGSVFNNKLGGMAAVTNIGNDLNW
RAAC02661   424  FDTHARGPGSTVAEIASGRLFGRPHGGVAGVANVGDDVNW
116621784   431  FDMQAGG.TTPVKALAAGKVFHRPIGGFVGVSNIGLDDNW 15642830    449  TGHDLAQANLYAFGRLAWNPDEEIERIVEEWIKLTFGDDE
148270004   449  TGHDLAQANLYAFGRLAWNPDEEIERIVEEWIKLTFGDDE
15613624    455  TGHLLAQANLYGYGRLTWNPNLSTEEVTTEWTRATFGDNE
118725970   472  TGHQMAQSNTYGYARLCWNPDLSAEKITDEWVRMTYSNYE
RAAC02661   464  TGHSLAQANLYAFGRLAWDPSLDPAGIAREWARLTYGDDP
116621784   470  SGNQLSQANLYGFGRLAWNPDLTSQQIIDEWTRLTFGNEP 15642830    489  KVLENVSYMLMKSHRTYEKYTTPFGLGWMVN.PGHHYGPN
148270004   489  KVLENVSYMLMKSHRTYEKYTTPFGLGWMVN.PGHHYGPN
15613624    495  EVIQTIHEMLLQSWLIYESYTAPLGVGWMVE.PGHHYGPN
118725970   512  KVVNTVKEMLLGSWRTYENYTSPLGIGWMVN.PNHHYGPN
RAAC02661   504  DVVRTVVGILMASWPAYEAYTAPLGVGWMVN.PGHHDGPN
116621784   510  KTVETITAMQLASWPVFEKYTGPLGLQTLTDIVGDHYGVA
```

FIG 21C

```
15642830    528  PEGYEYSKWGTYHRANWEAIGVDRTSR.GTGYTLQYHSPW
148270004   528  PEGYEYSKWGTYHRANWEAIGVDRTSR.GTGYTLQYHSPW-
15613624    534  VDGYEYSVWGTYHYADCHGIGVDRTVATGTGYTAQYFAEN
118725970   551  VDGYEYDKWGTYHRADHKGIGVDRTVKSGTGYAGQYHKDV
RAAC02661   543  PEGYEYSKWGTYHYADWRGVGVDRTMATGTGYTGQYHEPM
116621784   550  VEASEHNGWGQWHNADEKGVGMDRTVATGTGYIGQYRPPV
```

```
15642830    567  KEIYDDINTCPEDLLLFFHRVRYDHRLKSGKTLLQTMYDL
148270004   567  KEIYDDINTCPEDLLLFFHRVRYDHRLKSGKTLLQTIYDL
15613624    574  YELYEHLETCPDSLLLFFHHVPYTHKLKSGVTVIQHIYDT
118725970   591  AGIYEDMDKCPEELLLFFHHMPYDYILKSGETLIQYIYNT
RAAC02661   583  RSLYEHLETCPDELLLFFHHVPYTHVLHSGKTVIQHIYDA
116621784   590  AKMYESLETCPDDLLLFLHHVPYTYKLHSGKTVIQYLYDS
```

```
15642830    607  HFEGVEEVEEFIKKWEELKDRVSPDIFERVKERLHMQLEH
148270004   607  HFEGVEEVEEFIKKWEELKDRVPPDIFERVKERLHMQLEH
15613624    614  HFSGAEQAEQLLESWRSLEGKVDSERFQQVLERLEHQAEH
118725970   631  HFKGVEEVEELRNKWFSLKGWISEEIFLHVLERLDGQLEH
RAAC02661   623  HFDGVEAVAWMIEAWRRLQGRIDPVRFERVLARLEDQMQR
116621784   630  HYEGADAVAAWVRDFQSLRGHIDDQRYNEVLAQLRYQAAH
```

```
15642830    647  AKEWRDVINTYFYRRTGIPDEKGRK...............
148270004   647  AKEWRDVINTYFYRRTGIPDEKGRK...............
15613624    654  AKEWRDVINTYFYRKSGIPDEKKRT...............
118725970   671  SKEWRDVINTYFYRKTGISDELGRK...............
RAAC02661   663  AVEWRDVINTYFYRKCGIPDARGLH...............
116621784   670  VEVWRDAVNNWFHRESGIADAKGRVGNHPGRSEAEAMKLE
```

```
15642830    672  ......IYP
148270004   672  ......IYP
15613624    679  ......IYPI
118725970   696  ......IY
RAAC02661   688  ......IYP
116621784   710  GYTVAEITPWESASGGKAVTCPASKCTASMQFSGAPGWYT
```

```
15642830
148270004
15613624
118725970
RAAC02661
116621784   750  LRVQYFDLNGPVSSFKLWVGNQLVDEWSATDHLPARKLDA
```

```
15642830
148270004
15613624
118725970
RAAC02661
116621784   790  SSSTRREVSGIALRPGDQVRIEAIPEGRELAALDYLEILP
```

FIG 21D

```
15642830
148270004
15613624
118725970
RAAC02661
116621784    830 NEPRQ
```

FIG 22A

```
RAAC02925
52080473
17552962
15292329
66851010    1  MFKPPLCSEFRCRTARNRGIGDVLGSKTVHLVQLPAEENQ
40739053
```

```
RAAC02925
52080473
17552962
15292329
66851010   41  TARKTPRSSVHPKRRNDFLSRVISTNFLHFHSLSLSPQRR
40739053
```

```
RAAC02925
52080473
17552962    1              MAATVRNLPALFR.........
15292329    1              MGPIQRLVYTFGHRTCSQLPMIGG.........
66851010   81  TVVCLDVTSTQFLPLTNAGELDLAGFITNASPRQSDESSF
40739053    1              MPLR..AKVTNPGFAATSN.........
```

```
RAAC02925    1                         MDSVLFRQTG
52080473     1                         MSDDVLFSVNQ
17552962    14  ...........GLHSKEVCQKMSFSVSAAAKSEILVDTHG
15292329    25  ...........ATISQTKPTTMALSVRQSS.SSVLATESS
66851010   121  RGCCEGMLYSLSLFAMSTAPELPKELPGDEPDDVLFSSLY
40739053    18  .............MSTASNPDIPKAQHGDEPDDVLFNSLF
```

```
RAAC02925   11  .TVAWLGLNRPKQLNALSLEMIRLLRRHLDEMAQDPSVEL
52080473    12  NGAAAIVLNRPKALNSLTYDMVRLIGEKLNEWETDQNVSI
17552962    43  .SKKVVTLNRPKALNALNLEMVREFYPKLQAWNSSSDVDL
15292329    53  .NKGMIILNRPKALNAINLEMVRKIYKHLKKCEKSK..SL
66851010   161  .GVRLIELNRPKKLNSLNGSMARKILPRLKEWEKSQLANI
40739053    45  .GVRLVELNRPKKLNSLNGSMVRKILPRLKEWEKSQLANI
```

```
RAAC02925   50  VVLYGEGDRAFCAGGDIRALYDAKD.EPNLETAA...AFF
52080473    52  VVIKGAGPKGLCAGGDIKALYEARSSKQALQDAE...RFF
17552962    82  VILKGSDKAFCAGGDVLAVVRSFKDSESGKECTMHKDFF
15292329    90  VIIKGTGDKAFCAGGDVRALVEAGPTDES.......KSFF
66851010   200  VMLSGAGTKALCAGGDVASLALQNEQGPEGQQKS..TDFF
40739053    84  IMVAGAGTKALCAGGDVAALALQNEKGPEGQQAS..TDFF
```

```
RAAC02925   86  SEEYALDDRVARFPKPVVALWDGIVMGGGVGLTYGATWKV
52080473    89  ETEYEVDMAVHRFSKPIIACLDGIVMGGGVGLTYGASHRI
17552962   122  REEYILNHLIGTLNKQYVCLIDGIVMGGGCGLSVNGRFRV
15292329   123  REEYSTNALIGNYKIPYIAIIDGITMGGGVGLSVHGKYRV
66851010   238  GLEYRLDHIIATYTKPFISVMDGITMGGGVGLSVHAPFRI
40739053   122  GLEYKLDHVIATYSKPFISVMDGITMGGGVGLSVHAPFRI
```

FIG 22B

```
RAAC02925   126  ATDRTRFAMPETGIGFFPDVGMCHALSRMQGGLGHYLALT
52080473    129  VTERTKWAMPEMNIGFFPDVGAAYFLNKAPGRLGRYLGLT
17552962    162  ATEKTMLAMPETALGLFPDVGGSYFLSRLKGNLGMYLALT
15292329    163  ASDRTLFAMPETAIGLFPDVGGSYFLPRLQGKLGLYLGLT
66851010    278  ATERTVFAMPETTIGFFPDVGGSFFLPRLDGEIGTYLALT
40739053    162  ATERTVFAMPETTIGFFPDVGGSFFLPRLDGEIGTYLALT
```

```
RAAC02925   166  GESVGADVLLAAGLANGWLPSGERPSFEAELVKRGEQGE.
52080473    169  ASVIHAADVLYINGADAYMESGALERLLQAVEQTDWRLA.
17552962    202  GYRLLGADAFHAGLATHFVESSELAKLEKELVNIKDVTEN
15292329    203  GYRLRGADVYYSGIATHYCESSKIPDLETALLNCPDADD.
66851010    318  SERLNGVQALYAGIATHYFHSSVLSNLTARLAELVFRDHA
40739053    202  SARLTGVQALYAGIATHYFDSSVLGNLTQRLSELVFRDSA
```

```
RAAC02925   205  TAEQLQRWLAARLAVEHR.........PSEAVADFLRRVQ
52080473    208  SVEEKLDQLIRESKTEPS.........QESTLARDQQAID
17552962    242  SVDEVIRSFEPKKIPEFS.............LSKNLAQIR
15292329    242  .VPELLQKYHSPPEKPFS.............LQPVLEQIN
66851010    358  SLAERLDLVN.KTMAEFSVGLPPVEQEPIQLAGSLRSAID
40739053    242  TLQERLDLIN.RTMAEFATGLP....EEPQLAGQLRSAID
```

```
RAAC02925   236  AYFDSPSLSDILARLREGSSRDPFAAQALEILRQRSPLSL
52080473    239  RHFKYDKLEEILQSLE..SEGSTFSSNVKKTMLSKSPFSL
17552962    269  DSFKAKSVEEILASLEKDG..SDWAKKQAATLGKMSPTSL
15292329    268  KNFSADSVEGILENLQNDG..SEWAKKTLETLSKMSPTSM
66851010    397  RCFKHNTVEEIFRALEQETVHKEWAQKTLETLSSRSPTSL
40739053    277  RCFRHDTVEQIMKALEREKKCKKWAQETLETMSQRSPTSL
```

```
RAAC02925   276  AVTFEALRRAGNATYREVLETDLTLALQFIRRGDFVEGVR
52080473    277  KITLKQLADGRQKTLEECFATDLVLAKNFLKHNDFFEGVR
17552962    307  KVTHRQITEGSKMSYAKIFTMEYRLTQRFLADKDFHEGCR
15292329    306  KVTFRQLELGSQLSLAQCLIMEYRLAVRHLERSDFKEGVR
66851010    437  KVTLRQMRVGKKWSISETFQREYQIAAQFMKHPDFVEGVK
40739053    317  KVALRQMRVGQAWGIRETFQREYEIAARFMQHPDFVEGVK
```

```
RAAC02925   316  AQLVDKD.RRPRWRHADLASVTAEEVEAFFEPIAHLSIPF
52080473    317  SVLIDRD.QSPNYKYRNVSDVTDEAVDRFFQPSE..SVRF
17552962    347  AILVDKD.RKPKWNPATLADVKDSVVDNYFSPLPNNSDLK
15292329    346  ALLIDKD.QKPQWQPTKLADVTEEHVQWFFRKLPDTEELK
66851010    477  ARLMSKPPRQATWQPATLEEVTNDAVDAFFKLPADKSRLT
40739053    357  ARLMSKPPRQASWQPATLAEVSEKDVDEFFKIPQGKERIQ
```

```
RAAC02925   355  AD
52080473
17552962    386  L
15292329    385  L
66851010    517  LFNKTDYKQYPHAYGLPSEAEIEKFVRDSS....ESASKT
40739053    397  LLSQENWRSYPHSYGLPSEKAIEKFIREADPKSRASKGEV
```

FIG 22C

```
RAAC02925
52080473
17552962
15292329
66851010    553  VADFVEKWGHKEGVREKVAEVLARRTVQTPEGLRWE
40739053    437  IEHFVKEFEHKEGVKEKVAEVLARKTTKSAEGLIWQGEGA

RAAC02925
52080473
17552962
15292329
66851010
40739053    477  ETDGQ
```

FIG 23A

```
125973771    1   MAVDIKKIIKQMTLEEKAGLCSGLDFWHTKPVERLGIPS
RAAC03001    1       MSYRDLVSRLTLEEKASLCSGLNFWQTKPIERLGIPS
116334524    1   MDIERTL...AELTLPEKAALVSGKNNWYTAAVDRLDLPA
116617985    1   MSTEFNLSFVQGLTVREKAELVTGKDFWFTAENIENDIPK
116494248    1   MGVVVSNFHLAKITAEEKVKLTSGKDFWTSEHLADKGIPS
66851551     1   MVQLDVEKTIEELTLGEKVALTAGIDFWHTAAVPRLNIPS 125973771    40  IMMTDGPHGLRKQREDAEIADINNSVPATCFPSAAGLACS
RAAC03001    38  LCMTDGPHGVRLQRQGGSFTDSE...PATCFPTAAALASS
116334524    38  LMMTDGPSGLRKQINSGTTN.INDAIQAITYPAAALSAST
116617985    41  IMVTDGPSGLRKQASSADALGLNQSVEAIAFPSSALMASS
116494248    41  FRMSDGPHGLRYQALAADHLGINDSVPSTSFPTASASAAA
66851551     41  LRMSDGPNGVRGTR.......FFNGVPAACFPCATALGAT 125973771    80  WDRELVERVGAALGEECQAENVSILLGPGANIKRSPLCGR
RAAC03001    75  WDPALVERIGQALGDECRALGVHVLLGPGANIKRSPLCGR
116334524    77  WNESLMHQLGEHLGIEARAEQVSLLLGPGVNMKRSPLGGR
116617985    81  FNVDMLYQLGQNLGTASRAENVSVLLGPGINIKRSPLAGR
116494248    81  WDPDLIQAMGKAIGLEAQSLGVDMVLGPGVNMKRNPLCGR
66851551     74  WDTKLLYEVGRLMGEESIAKGAHVVLGPTINTQRSPLGGR 125973771    120 NFEYFSEDPYLSSELAASHIKGVQSQGVGACLKHFAANNQ
RAAC03001    115 NFEYFSEDPLLSSEMAAAHIRGVQSRGVGSSLKHFAANNQ
116334524    117 NFEYLAEDPLVAGKLGSAYVQGVQSQHVGVAVKHFAANNR
116617985    121 NFEYFSEDPYLTGELGSAYVKGVQSQGVGVSVKHFAANNR
116494248    121 NFEYFSEDPFLAGKLGAAWINGIQSQGIAACLKHFAANNQ
66851551     114 GFESFAEDGVLSGILAGHYCKGLQETGVAATLKHFVCNDQ 125973771    160 EHRRMTVDTIVDERTLREIYFASFENAVKKARPWVVMCAY
RAAC03001    155 EYRRMTTSAEVDERTLREIYLASFEGAVKGGRPWTVMCAY
116334524    157 ENQRFTASSDMSERTLRELYLRTFEIIVKSAYPATIMTSY
116617985    161 EDQRFTSSSNVDERALREIYLLAFEKIVKEAHPATLMCSY
116494248    161 ENDRLSSDSLVDPTALHEIYLEAFRIAVTESHPEAVMCSY
66851551     154 EHERLAVDSIVTMRAMREIYLLPFQLMRICKTACVMTAY 125973771    200 NKLNGEYCSENRYLLTEVLKNEWMHDGFVVSDWGAVNDRV
RAAC03001    195 NRLNGTYCSEHPWLLTQVLRREWGFDGVVVSDWGAVNDRV
116334524    197 NKINGVLNSQNERLLRRILRDEWGFHGAVMSDWGAVANTV
116617985    201 NAINGVLNSQNYRLLTEILRNEWGYTGVVMSDWGAVADNI
116494248    201 NKINGTYASDNLYLMTQVLRQQFGFGGAVITDWGALNDKV
66851551     194 NKVNGTHVSENKQIITDILRKEWGWDGLVMSDWFGTYSTC 125973771    240 SGLDAGLDLEMPTSHGITDKKIVEAVKSGKLSENILNRAV
RAAC03001    235 QGLAAGLDLEMPGGPYAQDAEIVQAVRDGRLDEAVLDAAV
116334524    237 QALKAGLDLEMPGKGQASINDIIRAVHTGELDEGTLNKAV
116617985    241 ASLKAGLDLEMPGNGAYSIDRIVSAVQNGQLEESKLDISV
116494248    241 AALNAGTDLEMPGDDHLFDGEALQAYQQGTLKLASLDRAV
66851551     234 DAINAGLDLEMPGPTRWRGTALAHAVSSNKAFEFVMDERV
```

FIG 23B

```
125973771   280  ERILKVIFMAL....ENKKENAQYDKDAHHRLARQAAAES
RAAC03001   275  ERLLALIDRAY....RPQGDSA..DLDAHHRLARQAAAES
116334524   277  RHLLHVVDDW.....LPADHAQPYDHAAHHQFARKLADDG
116617985   281  LRVLALVEKFR....VSEDDSTDYDKNNQHEFARKAAEDS
116494248   281  TKIAEIARKQR....PKFQGSREQLLQANGQLAQKIAESA
66851551    274  RNILNLHNFVEPLGIPENAPEKALNRPEDQALLRRAAAES
```

```
125973771   316  MVLLKNEDDVLPLK..KSGTIALIGAFVKKPRYQGSGSSH
RAAC03001   309  MVLLKNDGAVLPIA..PGRRVAVIGAFAVSPRYQGGGSSH
116334524   312  IILLKNHEDELPLDPQTTGKVVVIGELAENPRFQGSGSSH
116617985   317  IALLKNDDDVLPIK..QTEKIALIGELAQNPRYQGGGSSH
116494248   317  IVLLKNEAALLPLQ..ATDTVAVIGELAKATRFQGAGSSH
66851551    314  VVLIKNQDNILPLK..KEKPILVIGPNAKTAAYCGGGSAS
```

```
125973771   354  ITPTRLDDIYEEIKKAGG......................
RAAC03001   347  VNPARLDEPLAEMRRAFG......................
116334524   352  VNPTKLVSPLDELAGS........................
116617985   355  VNAYKVVTPHEVASNS........................
116494248   355  INASEIVSVLDGLKQK........................
66851551    352  LDAYYTVTPFEGVAAQSQGEVTFSQGVYSYKELPLLGPLL
```

```
125973771   372  .........................DKVNLVYSEGYRLE
RAAC03001   365  ............................DQL.VLYAPGYALD
116334524   368  ...........................GLKADYYPGYRLD
116617985   371  ............................DYNVTYTAGYSLS
116494248   371  ............................KVSFDYAAGYRLD
66851551    392  KTDDGKKGFKFRVYNEPPSEPNRQLIDELHLESSSGFLMD
```

```
125973771   386  ........................................
RAAC03001   378  ........................................
116334524   381  ........................................
116617985   384  ........................................
116494248   384  ........................................
66851551    432  YKHPKIKTFTFYVDMEGYFTPEEDGIYDFGVTVVGTKLF
```

```
125973771   386  ........................................
RAAC03001   378  ........................................
116334524   381  ........................................
116617985   384  ........................................
116494248   384  ........................................
66851551    472  VDDELVVDNSKNQRQGTAMFGNATVEEKGSKELKAGQTYK
```

```
125973771   386  ...............................NDGIDEELI
RAAC03001   378  ...............................DDAPRLELI
116334524   381  ...............................QSETNGDLA
116617985   384  ...............................EEKGNLDLE
116494248   384  ...............................DQD.DSQAT
66851551    512  VVLQFGTAPTSDLDMRGVVIFGPGGFRFGAARRVSQEELI
```

FIG 23C

```
125973771   395  NEAKKAASSSDVAVVFAGLPDEYESEGFDRTHMSIPENQN
RAAC03001   387  EEAVRAAAQADVAAIFAGLPESWESEGYDRPHMRMPDAHV
116334524   390  EAALTAAKTADHVIIFAGYPEAAESEGFDKASLMLPENQS
116617985   393  QQAESIAELSDKIIFFAGVPEQDESEGFDKKTIDLPENQV
116494248   392  AEALALARNHDKVVFVAGLPDNYESEGFDRQNMALPKVQN
66851551    552  SKAAELASQTSQVVIFAGLTSEWETEGYDRDHMDLPPGSD 125973771   435  RLIEAVAEVQSNIVVVLLNGSPVEMPWIDKVKSVLEAYLG
RAAC03001   427  ALIEAVTSAQPRTVVVLSNGAPVEMPWIHRVPAVIEAYLA
116334524   430  DLIGSLAKANVHTTVVLQNGSAVEMPWIHSVAAVVETYLA
116617985   433  NLIQKLSAINPNIIVVLQNGSAVATPWRNKVKAIVETYLA
116494248   432  DLLQAVTAVNPNVIVLLVAGAPVELPWVDQVKAVVNLSLG
66851551    592  EMISRVLDANPDTVVVIQSGTPVTMPWAHKAKALLQAWFG 125973771   475  GQALGGALADVLFGEVNPSGKLAETFPVKLSHNPSYLNFP
RAAC03001   467  GQAFGGAIADVLSGAVNPSGKLAETFPLRLEHNPSHPYFP
116334524   470  GEAVGEATWDIITGAVNPSGHLTETFPRRLTDTPMAPTFG
116617985   473  GEAVGEATWNILTGQTNPSGKLAETFPEKIEDTPAYGTFN
116494248   472  GERIGAAAANVLTGAVNPSGKLAESYPLKYQDVPSADVYD
66851551    632  GNECGNGIADVLYGNVNPAAKLPLSFPVRLQDNPSYLNFR 125973771   515  GEDDRVEYKEGLFVGYRYYDTKGIEPLFPFGHGLSYTKFE
RAAC03001   507  GEGDRSEYREGVFVGYRYYDTKEMDVLFPFGHGLSYTTFE
116334524   510  QDPHHEYYTEGIFMGYRYYDTHEMHVLFPFGHGLSYTTFE
116617985   513  ASVDEENYHEGIFVGYRHYDLKRKEVAFPFGHGLSYTDFK
116494248   512  KKPRSVPYVESTYIGYRYYDKAKVPVAFPFGFGLSYTSFA
66851551    672  SERGRVLYGEDIYVGYRYYEKVDLAPLFPFGHGLSYTTFS 125973771   555  YSDISVDKKDVS....DNSIINVSVKVKNVGKMAGKEIVQ
RAAC03001   547  YEAIRMSREQVR....DDDVLTVQVDVRNTGQRAGKEVVQ
116334524   550  YTNLKLTQN........ERGATVTFDVTNTGARSGQAVPQ
116617985   553  YDDLEIVANT.......KKHVTGKIKITNVGSIYGKETAQ
116494248   552  LKNIQLSSDHVT....DDQPLTISLQVTNTGQVDGAEVVQ
66851551    712  RSDLSLATTPEKPQLEDGEPITVTSVTNTGSVAGAEIVQ 125973771   591  LYVKDVKSSVRRPEKELKGFEKVFLNPGEEKTVTFTLDKR
RAAC03001   583  VYVEPRSSRVVRPRRELRAFAKVALAPGETRTVEFQLGKR
116334524   582  LYIANHASHVPMPTKELRAFTKVAIAPGETETVTLALDRR
116617985   586  IYIQNLESRVEKPRQELKAFVKVGLNPGESKTVEFFLDRR
116494248   588  VYVQEQQPRPLRPEKSLKAFKKVFVKAGQTVNVALELKAQ
66851551    752  LWVAPPPTGVNRPVRELKGFTKVFLQPGETKKVEIVVEKK 125973771   631  .AFAYYNTQIKDWHVESGEFLILIGRSSR..DIVLKESVR
RAAC03001   623  .AFAYYDVDAGDFAVESGWYEIRVGSSSR..DLRLTASVE
116334524   622  .DFSWWCEPKARWQADSGDYEVMIGESSR..DIRLQVKLT
116617985   626  .SFAWYNVKKSIWQVDQGDYNLKIGSSSR..DIRLEKTVS
116494248   628  .AFKEWREQTQTWVLPEAQKAIAVGTSVTNIDAVLPVSFT
66851551    792  LATSWWDEQREKWASEKGTYEVLVTGTGD...........
```

FIG 23D

```
125973771   668 .............................VNSTVKIR.KR
RAAC03001   660 ............................VTSAAPRRPVS
116334524   659 .........................MDFKNSP.APITTET
116617985   663 ........................LEMGTTNNRPISGDT
116494248   667 GETFNNFATIPNWYTTLSGKPSVQDFEQLTDQKVPAPHEF
66851551    821 ........................................
```

```
125973771   678 FTVNSAVEDVMSDSSAAAVLGPVLKEITDALQID....MD
RAAC03001   671 VHANAALGDLLDDPATGPVLRELLKEKLADSPLG....SE
116334524   673 YMAAIVKNPQLRDLFKQVVLAPEYAGPENFLAIT...DDQ
116617985   678 YISEIIN....RDGLHESLVASGLQTAIESISAS...DSN
116494248   707 VPGEFTRLNTPREMKKHSLLLRLVAWITVKIRTKDYIDKQ
66851551    821 .................EVLKSSFEVEKTRYWLGL
```

```
125973771   714 N.AHDMMAANIKNMPLR...SLVGYSQGRLSEEMLEELVD
RAAC03001   707 MDANPMFEAFMRFTPIGRVTTLFGVPRD.ENERVLAKLRA
116334524   710 GSLQIFQDRMFMNMPLR...AVVALGG...PQALITDFIT
116617985   711 R.......ELMENLPLR...AIIMIGA...NVDQVNKFIE
116494248   747 GPEAKFQQAIVLDTPLI...RLAQQASGALKLSMVDRLVA
66851551
```

```
125973771   750 KINNVE
RAAC03001   746 AQEEGQPEEGRG
116334524   744 RANTLLRQ
116617985   738 LANN
116494248   784 AANHQYVKMIFR
66851551
```

FIG 24A

| | | |
|---|---|---|
| RAAC02913 | 1 | MTTRLWRHPNPRVMRMEGCLMKPRQLALGLCAGACAWMFG |
| 15614969 | 1 | MKKILIHGCVFAIILLMTYGAVQNPFSSQYI |
| 124523066 | 1 | MNKAKR.LIALGLIAILALLLAGNPLSTRYL |
| 114843671 | 1 | MKIFYIKYPKKSFWIIFSLAILLLI |
| 89101184 | 1 | MKKLAG....MLLIGAFSLMLVNNPFTDLYV |
| 2634042 | 1 | MYKKFVPFAVFLFLFFVSFEMMENPHALDYI |

| | | |
|---|---|---|
| RAAC02913 | 41 | AGLWIRADAPPQPTPAPSERVWEEVSRAWANPPIDARRDR |
| 15614969 | 32 | GQLKEEALPVAKMTDSLYEEIKDRAPE.YEQPAIDAKIDR |
| 124523066 | 31 | ....QERAAFSTKENELQEKIEQAAER.FYRPPENAKIDR |
| 114843671 | 26 | FLIYIITRSVS............................ |
| 89101184 | 28 | SQLKMDSLAVTAESDSLLQRIEKESEN.YYIAPQDARIDP |
| 2634042 | 32 | GAMKKDTVTVTASKDPLYEELQKAPE.YEVKPQNARIDK |

| | | |
|---|---|---|
| RAAC02913 | 81 | VWHNIPGLSGFALDTAASERETARF.HDGALHLVWRTVPP |
| 15614969 | 71 | VWKAIPGYNGLEVDVESSYNRMKQEGRFDERYLVFRETKP |
| 124523066 | 66 | VWKAIPGYNGVEVDKKASYSKMKQDGRYDERKLVFKQIPP |
| 114843671 | 37 | ................................VFNSNEP |
| 89101184 | 67 | VWKAIPGYNGVKVDVEASYKKMKGEKKFDPDKLVLEQIEP |
| 2634042 | 71 | VWKSIPGYNGLKVNIEQSYKKMKQHGKFREKDLVYSQVKP |

| | | |
|---|---|---|
| RAAC02913 | 120 | RVRLRDLPPDVIYRGPAEEKSVALMVNVSWGEAYVPRMLQ |
| 15614969 | 111 | SVHLDDLPPSPVFRGNPEKPMVTLLVNVAWGNEHLPTMLK |
| 124523066 | 106 | AVHLKDLDPAPVYTGNPDKPMVAFLINVAWGNEYLPDMLK |
| 114843671 | 44 | ..........IYKGDTKEKKIAFACNVAWGDEYIPKMLD |
| 89101184 | 107 | EKKLGDLPPAPIYKGNPDKPMVSFIINVAWGNEYLSGMLA |
| 2634042 | 111 | SVHLESLQPEPIYKGNPDKPMVAFLINVAWGNEYLEKMLP |

| | | |
|---|---|---|
| RAAC02913 | 160 | ILRDAHVKATFFVDGAWAKKFPDLVRAMAQDGHAVESHGS |
| 15614969 | 151 | TMNKYDVKSTFFLDGSWVKKHPQLATMIVEEGHEIGNHAY |
| 124523066 | 146 | TLKKHHLHATFFLEGRWAKENPELARMIVSGGHETGNHSY |
| 114843671 | 73 | IFKDNNIHITFFFEGKWAEKNPDVVKDIYQKGHEIGSHGY |
| 89101184 | 147 | TLKKHKVTATFFLEGRWVQQNPELAKMITEAGHEAGNHSF |
| 2634042 | 151 | ILQKHQVKATFFLEGNWVRNNVQLAKKIAKDGHEIGNHSY |

| | | |
|---|---|---|
| RAAC02913 | 200 | GHPDFRRLNDAKLAAQIDETNRVLAAITGRAPRLIAPPAG |
| 15614969 | 191 | SHPDMQRLTRERMDEEIVQTNEVIKATIEVTPKWFAPPSG |
| 124523066 | 186 | THPDFSTLPESKIKSQLVKTNRVLEAITEEKVKWFAPPSG |
| 114843671 | 113 | THVKYTNLSRQQYEEDIKKSGEILEKITGTKPTLFAPPYG |
| 89101184 | 187 | THPDMKTISSARIREEIEKTNQVIKATTGQEVTWFAPPSG |
| 2634042 | 191 | NHPDMSKLTTGRISEQLDKTNEQIEQTIGVKPKWFAPPSG |

| | | |
|---|---|---|
| RAAC02913 | 240 | SYDARLAPLAKSRGMYAILWTADTVDWKNPPPAAIVERVQ |
| 15614969 | 231 | SYNDLVVQRAAEHGMRTIMWSVDTIDWRNPDPNEMVDRVL |
| 124523066 | 226 | SYRDEAVSIAKSMGMETIMWTVDTVDWQNPSPETIVERVT |
| 114843671 | 153 | DFNDEVVKVAEQLGYKVILWSLDTIDWNNPSPQTIVDRVM |
| 89101184 | 227 | SYRDETVRIAAEKKLKTVMWSLDTVDWRKPSPEELLNRVV |
| 2634042 | 231 | SFRKAVIDIAAEKQMGTVMWTVDTIDWQKPAPSVLQTRVL |

FIG 24B

```
RAAC02913   280  RGAEPGALVLMHPTASTVEALPVMIRWLEARGYRMKTVED
15614969    271  SKVHPGAMILMHPTESSAAGLENLIRGIQDRGLHIGTVSD
124523066   266  AKAQGGSLILMHPTASTAKALEPLIARLEKKNLQVGTVSK
114843671   193  TKYHNGAIVLMHPTQNTVEALPQIIKQLKEKGYKITKVSE
89101184    267  PKVHNGAIILMHPTDSTAKSLDSMITQIKGKDFEIASVSR
2634042     271  SKIHNGAMILMHPTDPTAESLEALITQIKDKGYALGTVTE

RAAC02913   320  VIDERPAVTPPTILARETIRL
15614969    311  LMDESRINAGVTP
124523066   306  LLDEERIIKNEDGTFLNSEKDPADTKDGTE
114843671   233  VIVDNN
89101184    307  LLSEERIMDKK
2634042     311  LMDETRLLK
```

FIG 25A

| | | |
|---|---|---|
| 595264 | 1 | MNELIPL |
| 20803949 | 1 | MRRLDDR |
| 17380381 | 1 | MKHLDYI |
| 128438 | 1 | MKRPAYM |
| 1001913 | 1 | MKNLNII |
| RAAC02839 | 1 | MFDASYIHRGDLCGREGRHVSRRMGSALIGLLAASSFVTY |

| | | |
|---|---|---|
| 595264 | 8 | SAVRCNYGDVSGSRSVYLTFDDGPNPFCTPLVLDVLTQHR |
| 20803949 | 8 | WEVQSECADGTGRRSVYLTFDDGPNPCFTPQILDVLAQNR |
| 17380381 | 8 | HEVPSNCDYGTEDRSIYLTFDDGPNPHCTPEILDVLAEYG |
| 128438 | 8 | SEVPVNHTSGQEARCVYLTFDDGPNPFCTPQILDVLAEHR |
| 1001913 | 8 | DSVDVDAG..ADDPCVYLTFDDGPNPFCTPHILDVLAQHA |
| RAAC02839 | 41 | GTPIVHATPSGQAKVVYLTFDDGPSQRYTPKLLDILRNQH |

| | | |
|---|---|---|
| 595264 | 48 | VPATFFVIGTYAADQPELIRRMIAEGHEVANHTMTHPDLS |
| 20803949 | 48 | VPATFFVIGAYAAEHPDLIQRMIAEGHEVGNHTMSHPDLS |
| 17380381 | 48 | VPATFFVIGTYAKSQPELIRRIVAEGHEVANHTMTHPDLS |
| 128438 | 48 | VPATFFAIGSYVKDHPELIRRLVAEGHDVANHTMTHPDLA |
| 1001913 | 46 | VSATFFVIGANAEVHPGLVQRIVSEGHGVANHTMTHPDLA |
| RAAC02839 | 81 | ISATFFVVGYRCEQFPDIVRRIQREGHEIGNHGFSHLDPK |

| | | |
|---|---|---|
| 595264 | 88 | RCEAAEIHDEVLTASRAIRLACPQALPRHMRAPYGIWTED |
| 20803949 | 88 | KCGLGEVQREVFEANQAIMLACPQASIRYIRAPYGAWSEE |
| 17380381 | 88 | TCGPHEVEREIVEASEAIIAACPQAAVRHIRAPYGVWSEE |
| 128438 | 88 | TCDPKDVKREIDEAHQAIVSACPQALVRHLRAPYGVWTED |
| 1001913 | 86 | TCSRPQVEREIDEANRAIISACPGASIRHIRAPYGKWTEE |
| RAAC02839 | 121 | KHALEEFILDIRKTDTAVVKACG.TKPLYYRPPYGSIDAS |

| | | |
|---|---|---|
| 595264 | 128 | VLATSAKAGLAAVHWSVDPRDWSRPGVDSIVKSVLAAVRP |
| 20803949 | 128 | VLTASEIAGLAALHWSIDPRDWSRPGTDAIVDAVLASVRP |
| 17380381 | 128 | ALTRSASAGLTAIHWSADPRDWSRPGANAIVDAVLDSVRP |
| 128438 | 128 | VLSASVRAGLGAVHWSADPRDWSCPGVDVIVDEVLAAARP |
| 1001913 | 126 | ALVKSASLGLAPVHWSVDPRDWSCPGVDAIVDRVLAAAKP |
| RAAC02839 | 160 | EIDCVHKLGHPIALWTVDSMDWKAKSANAIVSQVERHAQP |

| | | |
|---|---|---|
| 595264 | 168 | GAIVLLHDGYPPGEEASCIDS..............TSREQ |
| 20803949 | 168 | GAIVLLHDGCPPDESTRSTQA..............SLRNQ |
| 17380381 | 168 | GAIVLLHDGCPPD..ESGALT..............GLRDQ |
| 128438 | 168 | GAIVLLHDGCPPDEVEQCSLA..............GLRDQ |
| 1001913 | 166 | GSIVLLHEDGPPGAADPTKLP..............TLRDQ |
| RAAC02839 | 200 | GSIILFHDGISSSRYTIEAMPRIIRDFRRDGYTFKTLPIR |

| | | |
|---|---|---|
| 595264 | 194 | TVRALAYLIPALQLRGFEIHPLPQLH |
| 20803949 | 194 | TVMALSNLIPALDACGYEIRSLPEHH |
| 17380381 | 192 | TLMALSRIVPALHERGFAIRPLPPHH |
| 128438 | 194 | TLIALSRIIPALHSRGFEIRSLP |
| 1001913 | 192 | TLAAISAIIKSLRSRGLTIRSLP |
| RAAC02839 | 240 | DSLRIEAFVPKTDDDAILPRDTHDVQRKHRPSVGTRCIGR |

FIG 25B

```
595264
20803949
17380381
128438
1001913
RAAC02839    280 QSRD
```

FIG 26A

| | | |
|---|---|---|
| RAAC00961 | 1 | MGVVHPRVGHAVPHHLWPQSSTGAPLLRDSERARPRVRVY |
| 124523411 | | |
| 15806097 | | |
| 21219643 | | |
| 13475158 | | |
| 21219455 | | |

| | | |
|---|---|---|
| RAAC00961 | 41 | QRDREVHGDGGSHRHEAGRADADGVHRDAPAPPHLSADSR |
| 124523411 | | |
| 15806097 | | |
| 21219643 | | |
| 13475158 | | |
| 21219455 | | |

| | | |
|---|---|---|
| RAAC00961 | 81 | SGGGECAVRRAGGCGGVREVSGGSSGVLALGARRPVHPEP |
| 124523411 | | |
| 15806097 | | |
| 21219643 | | |
| 13475158 | | |
| 21219455 | | |

| | | |
|---|---|---|
| RAAC00961 | 121 | HARGVQRDAELWRGGAHRAKDHAVCHEEASVPLRVAGVAA |
| 124523411 | | |
| 15806097 | | |
| 21219643 | 1 | MNRPEAPR |
| 13475158 | | |
| 21219455 | | |

| | | |
|---|---|---|
| RAAC00961 | 161 | RASSDVRGSAVIGWLVAVVLAVLVVYAGLPFVWTRGLGRS |
| 124523411 | 1 | MEVIIWVLILFILIYAIIPYVLAAKLGFW |
| 15806097 | 1 | MKRGVRGLLLGAALYIGLPYLLVQVGNLG |
| 21219643 | 9 | TRHGFPTGRAVYAVAPVVAAALAHIGPAATWLPELRRRRF |
| 13475158 | 1 | MRRLDDRWKVQSE |
| 21219455 | 1 | MR........SEP |

| | | |
|---|---|---|
| RAAC00961 | 201 | CIRRTPKP.GCVALTFDDGPHPVYTPRLLNALREAGARAT |
| 124523411 | 30 | VCWKGKKD.AEIALTFDDGPDPVYTPVLLDLLKRERIKAT |
| 15806097 | 30 | LVREGRRARREVALTFDDGPDPQTTPAVLAALREADMHAT |
| 21219643 | 49 | PGLAGRGSPGHVALTFDDGPDPASTPRFLDTLDGLGVRAT |
| 13475158 | 14 | CADGTGR..RSVYLTFDDGPNPCFTPQILDVLAQNRVPAT |
| 21219455 | 6 | ILRMTGRG.RTMLLTFDDGPHPEYTPKILDTLAKYEVRAT |

| | | |
|---|---|---|
| RAAC00961 | 240 | FFVIAEHALRHPEIVERMLAEGHEVQVHGYRHWFVPLLPP |
| 124523411 | 69 | FFLVGERAARYPELVLRMSREGHCIGLHNYKHQCNWLISP |
| 15806097 | 70 | FFVIAGKAQAHPDLIRQMLEEGHEVEAHADKHVHAWIRTP |
| 21219643 | 89 | FFVLGENALRHPALTRELVRRGHELAVHGWTHDRPWWPSP |
| 13475158 | 52 | FFVIGAYAAEHPELIQRMIAEGHEVGNHTMSHPDLSKCGL |
| 21219455 | 45 | FFVCGEMADYNRDLLTRMADEGHVVGNHTWSHPLLTKLTR |

FIG 26B

```
RAAC00961   280 GLTARQCVGARDILAQRFGIDP.RVYRPTWGACNLATLVM
124523411   109 WKNARTLEQSARIIENITGERP.VFYRPPWGMMHLLDFFL
15806097    110 WGAALDPLRAVRAVG.AMTGRPVRFHRPPHGAYTLSTWLG
21219643    129 ARDTRELLRAVRVVDEVSGRAP.RWYRPPYGILTSGRWAA
13475158     92 GEVQREVFEANQAIMLACPQASIRYIRAPYGAWSEEVFTA
21219455     85 RRIRSEMERTSEVVEQAYGEAP.RWFRAPYGAWNRAAFQL

RAAC00961   319 LRRSRMSMLLWSVMVGDWRRTP.PEELARRILAKLDARSV
124523411   148 HK..QFRMVHWSKMFRDWKRKGGSKKVSNGLITRVESGDV
15806097    149 QRLAGVRGAHWSIEGCDWHPESIPDTVRERLAALLVPGAV
21219643    168 ARRAGLRPVLWTAWGKDWRHDATPASVRATVAADLCGGGT
13475158    132 SEIAGLAALHWSIDPRDWSRPG.TDAIVDAVLASVRPGAI
21219455    124 GSELGMEPLAWTVDTLDWTTPG.TGTIVDRVEEGAAPGVV

RAAC00961   358 IVLHDSDESP....GAERGAPESVIAAIPAVVEEVRRRGY
124523411   186 ILLHDCGVTP....GADEDAPQYTIEGLRVAIPALKARGF
15806097    189 IVLHDAGPG..........ARVTVPLLPSLLADLKARGY
21219643    208 VLLHDTDHAS......APGSWRATLGALPDIVRDCREAGL
13475158    171 VLLHDGCPPDESTRSTQASLRNQTVMALSNLIPALDACGY
21219455    163 VLSHDAGGD...........RSQSVRALRRYLPELLDSGY

RAAC00961   394 TFVLASECE
124523411   222 RFVRMDEMFDKHFSIKTSHRRKEIEP
15806097    218 RSVTLAELGGAAPQDWPGLKRRGFLALDAVFDRLGHIHFA
21219643    242 AVGPLGEHGAGGATGTPGTAAVAGTAGTAGTAASFRSPAP
13475158    211 EIRSLPEHH
21219455    192 HL.TVPRRRLI

RAAC00961
124523411
15806097    258 GGRADNLFRIARVPFPLEGARLADGTPIPHGAPALEFHVN
21219643    282 G
13475158
21219455

RAAC00961
124523411
15806097    298 NPILVDLGPRASVRQARREDFRVVARELQTRPEYADVGYV
21219643
13475158
21219455

RAAC00961
124523411
15806097    338 FCLSAVSPLLGLLGFENHDLPAADARRLRRWANVLRRAYG
21219643
13475158
21219455
```

FIG 26C

```
RAAC00961
124523411
15806097    378 NDPNAKAPRLSVLTREEFLALYGS
21219643
13475158
21219455
```

FIG 27A

```
RAAC00361    1  MFPTRGPESRQLLPTARSRPPRSPPARGPRALLRSRPLQR
52078651
16077225
89100305
15612806
121535454
```

```
RAAC00361   41  AKKRLRERLVSLVRRMNRIAEQAQIPELPTSVVLDIGRLV
52078651
16077225
89100305
15612806
121535454
```

```
RAAC00361   81  PAKRLVGLHHHEPVTKRDPADAIVVLLRHLLGQGEIRKGI
52078651     1                       MNHFYVWHIKRIKQLIIIM
16077225     1                       MNHFYVWHIKRVKQLIIIL
89100305     1                       MNFFYVVNGKAIKQGLLIM
15612806     1                       MKFFWVLRAKKIKQLTIIL
121535454    1                        MIVDLRRFMGHRHLFFGI
```

```
RAAC00361  121  VEGRNTERAVRAFAPFHQALHVLLRAAHDVLNEIGSPRED
52078651    20  IAA.....................................
16077225    20  IAA.....................................
89100305    20  IAS.....................................
15612806    20  LTA.....................................
121535454   19  IG......................................
```

```
RAAC00361  161  RRRASQEIVSADHERDDLGLLDDTGREVLKRFEQLPRRPP
52078651    23  ........................................
16077225    23  ........................................
89100305    23  ........................................
15612806    23  ........................................
121535454   21  ........................................
```

```
RAAC00361  201  RLRLDMQRRADLAGEAGAKALRKALLRRTRTVAICNGVAE
52078651    23  ........................................
16077225    23  ........................................
89100305    23  ........................................
15612806    23  ........................................
121535454   21  ........................................
```

```
RAAC00361  241  REHQHDHRLLGESLIVSYGLSRRLVTRGAHAPVARSHRRC
52078651    23  ........................................
16077225    23  ........................................
89100305    23  ........................................
15612806    23  ........................................
121535454   21  ........................................
```

FIG 27B

```
RAAC00361   281  GRCKHCRQNHKGGWPMRSFWKRLRAGVAALTAACVCAVSC
52078651     23  ................................FATASF
16077225     23  ................................FAAASF
89100305     23  ................................FFTAWF
15612806     23  ................................FFCASL
121535454    21  ................................IFAIST

RAAC00361   321  MSLQAGSVRAADTKAQAPKAVYKVDTKEKVVALTFDISWG
52078651     29  FYVQNLLPLPVFSTEGGAKAVYRGDSDTNEVALTFNISWG
16077225     29  FYIQRAVPLPVFSTDTGPKAIYKGETDSKDISLTFDISWG
89100305     29  LYMENIIHMPVFSANDGPKAIYKGE...KDAALTFNIGWG
15612806     29  LYLERS.HLMVFSTPEGPQAFHKAETDEKVAALTFNISWG
121535454    27  LYVQAANIIAG.....GPIAIAGTNTDHKVVALTFDHSWG

RAAC00361   361  HRTPEPVLETLKKCGVTKATFFLSGPWTMHHPEIAKKIKA
52078651     69  DQKAMPILDTLKANGIKDATFFLSASWAERHPDVVERIRK
16077225     69  DERAEPILNTLKANGIKNATFFLSASWAERHPDTVARIVK
89100305     66  DEKAEPILDVLKKQNVKAATFFLSGSWAERHPELVARIVK
15612806     68  EQRVKPIIDVLQSKKVEEATFFISASWAERHPELVELIQE
121535454    62  NKFTPSILDTLKRHNL.KVTFFIMGPWAKKYPEVAQRMVA

RAAC00361   401  MGYEIGSHGYLHKDYSNYPDSWIREQAMLADKAIQQVTGV
52078651    109  DGHQIGSMGYAYKNYSQMKKSEIKKDLAKARHSFQKLGLD
16077225    109  DGHQIGSMGYAYKNYANLESSEIKKDMNRAQTAFEKLGVK
89100305    106  EGYEIGMLGYDYKDYTDLEESKIRQDLAKGQEAFKKLNVK
15612806    108  AGYHIGSHGYQYKNYTTWEDEKIRKDLRQSQQVISSITGE
121535454   101  DGHEIASHGYRHENYGDMTTEWVKEDILKAHALIKEVTGV

RAAC00361   441  KPKLFRTPNGDLNLRVIRCLTSMGYTVVQWNTDSLDWKNP
52078651    149  DLTLLRPPTGQFNKDVLDVAKQYGYTVVHYSINSDDWTNP
16077225    149  DIQLLRPPTGQFNKNVLKVAKQYNYTVVHYSVNSQDWTNP
89100305    146  DIKLVRAPTGHFDQKTLNVAEKMGYTVVHWSIDSKDWTNP
15612806    148  KPTLLRPPNGDFDKRVLNLAESYDYTVVHWSINSRDYENP
121535454   141  DPTLIRPPNGHYSQRSLKAADELGYKTIIWNVDSLDWKNP

RAAC00361   481  GVDAIVNRVTKRVVPGDIVLMHASDSSKQIVEALPRIVEN
52078651    189  GVQKIVQNVNGTVNAGDIVLFHASDSAKQTKEALPEIVHH
16077225    189  GVEKIIDNVTKQVSGGDIILLHASDSAKQTEEALPDIIHQ
89100305    186  GVERIAENAAKAGK.GDIILLHASDSAKQTAKALPAIIGN
15612806    188  GVDAIVRQVVDHISPGDIVLMHASDSAKQTHKALPIIIDQ
121535454   181  GRDVIIERVMKRLKPGAIILMHASDPVQTAEALPILLEK

RAAC00361   521  LRQQGYRFVTVSELLAGANVQSKVQ
52078651    229  LRSKGLKNVTVSELIANTDAKSSEVK
16077225    229  LKEKGLKNVTVGDLIANSDAKSAEVK
89100305    225  YKDKGLKLVSVSEMMANASTKSNEIK
15612806    228  LKGKGYHFRSIEELMADAHPTHDEIK
121535454   221  IKAEGYQIVTVSELLSKYSEKGIQRH
```

US 7,858,353 B2

THERMOPHILIC AND THERMOACIDOPHILIC BIOPOLYMER-DEGRADING GENES AND ENZYMES FROM *ALICYCLOBACILLUS ACIDOCALDARIUS* AND RELATED ORGANISMS, METHODS

RELATED APPLICATIONS

This application claims the benefit of the filing date of U.S. Provisional Patent Application Ser. No. 61/025,136, filed Jan. 31, 2008, for "THERMOPHILIC AND THERMOACIDOPHILIC BIOPOLYMER-DEGRADING GENES AND ENZYMES FROM *ALICYCLOBACILLUS ACIDOCALDARIUS* AND RELATED ORGANISMS, METHODS."

GOVERNMENT RIGHTS

This invention was made with government support under Contract Number DE-AC07-99ID13727 and Contract Number DE-AC07-05ID14517 awarded by the United States Department of Energy. The government has certain rights in the invention.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "SEQ LIST III.ST25.txt" which is 1,829 KB and created on Jan. 29, 2009.

TECHNICAL FIELD

The present invention relates generally to biotechnology. More specifically, the present invention relates to isolated and/or purified polypeptides and nucleic acid sequences encoding polypeptides from *Alicyclobacillus acidocaldarius* and methods for their use.

BACKGROUND

Dilute acid hydrolysis to remove hemicellulose from lignocellulosic materials is one of the most developed pretreatment techniques for lignocellulose and is currently favored (Hemelinck et al., 2005) because it results in fairly high yields of xylose (75-90%). Conditions that are typically used range from 0.1 to 1.5% sulfuric acid and temperatures above 160° C. The high temperatures used result in significant levels of thermal decomposition products that inhibit subsequent microbial fermentations (Lavarack et al., 2002). High temperature hydrolysis requires pressurized systems, steam generation, and corrosion resistant materials in reactor construction due to the more corrosive nature of acid at elevated temperatures.

Low temperature acid hydrolyses are of interest because they have the potential to overcome several of the above shortcomings (Tsao et al., 1987). It has been demonstrated that 90% of hemicellulose can be solubilized as oligomers in a few hours of acid treatment in the temperature range of 80-100° C. It has also been demonstrated that the sugars produced in low temperature acid hydrolysis are stable under those same conditions for at least 24 hours with no detectable degradation to furfural decomposition products. Finally, sulfuric acid typically used in pretreatments is not as corrosive at lower temperatures. The use of lower temperature acid pretreatments requires much longer reaction times to achieve acceptable levels of hydrolysis. Although 90% hemicellulose solubilization has been shown (Tsao, 1987), the bulk of the sugars are in the form of oligomers and are not in the monomeric form. The organisms currently favored in subsequent fermentation steps cannot utilize sugar oligomers (Garrote et al., 2001) and the oligomer-containing hydrolysates require further processing to monomers, usually as a second acid or alkaline hydrolysis step (Garrote et al., 2001).

Other acidic pretreatment methods include autohydrolysis and hot water washing. In autohydrolysis, biomass is treated with steam at high temperatures (~240° C.), which cleaves acetyl side chains associated with hemicellulose to produce acetic acid that functions in a similar manner to sulfuric acid in acid hydrolysis. Higher pretreatment temperatures are required as compared to dilute acid hydrolysis because acetic acid is a much weaker acid than sulfuric. At temperatures below 240° C., the hemicellulose is not completely hydrolyzed to sugar monomers and has high levels of oligomers (Garrote et al., 2001). In hot water washing, biomass is contacted with water (under pressure) at elevated temperatures 160-220° C. This process can effectively hydrolyze greater than 90% of the hemicellulose present and the solubilized hemicellulose was typically over 95% in the form of oligomers (Liu and Wyman, 2003).

BRIEF SUMMARY OF THE INVENTION

Embodiments of the invention relate to purified and/or isolated nucleotide sequences of the genome of *Alicyclobacillus acidocaldarius*, or a homologue or fragment thereof. In one embodiment of the invention, the nucleotide sequence is selected from SEQ ID Nos. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, 463 or a homologue or fragment thereof. In another embodiment of the invention, the homologue is selected from the group consisting of a nucleotide sequence having at least 80% sequence identity to SEQ ID No. 1, 18, 51, 68, 85, 101, 118, 135, 152, 167, 184, 201, 218, 235, 252, 269, 286, 303, 320, 336, 353, 370, 387, 404, 421, or 438; at least 93% sequence identity to SEQ ID No. 461; at least 94% sequence identity to SEQ ID No. 35; at least 96% sequence identity to SEQ ID No. 459; at least 99% sequence identity to SEQ ID No. 463; at least 99.6% sequence identity to SEQ ID No. 457; and at least 99.7% sequence identity to SEQ ID No. 455.

Embodiments of the invention may further relate to an isolated and/or purified nucleic acid sequence comprising a nucleic acid sequence encoding a polypeptide selected from the group consisting of a polypeptide having at least 90% sequence identity to SEQ ID No. 2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID No. 462; at least 94% sequence identity to SEQ ID No. 36; at least 96% sequence identity to SEQ ID No. 460; at least 99% sequence identity to SEQ ID No. 464; at least 99.6% sequence identity to SEQ ID No. 458; and at least 99.7% sequence identity to SEQ ID No. 456.

Embodiments of the invention also relate to isolated and/or purified polypeptides encoded by a nucleotide sequence of the genome of *Alicyclobacillus acidocaldarius*, or a homologue or fragment thereof. In one embodiment, the nucleotide sequence is selected from the group consisting of a nucleotide sequence having at least 80% sequence identity to SEQ ID No. 1, 18, 51, 68, 85, 101, 118, 135, 152, 167, 184, 201, 218, 235, 252, 269, 286, 303, 320, 336, 353, 370, 387, 404, 421, or 438; at least 93% sequence identity to SEQ ID No. 461; at least 94% sequence identity to SEQ ID No. 35; at least 96% sequence identity to SEQ ID No. 459; at least 99% sequence identity to SEQ ID No. 463; at least 99.6% sequence identity to SEQ ID No. 457; and at least 99.7% sequence identity to SEQ ID No. 455.

In another embodiment of the invention, the nucleotide sequence is selected from SEQ ID No. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, 463 or a homologue or fragment thereof. In still another embodiment, the polypeptide has the amino acid sequence of SEQ ID Nos. 2, 19, 52, 69, 86, 102, 119, 136, 153, 168, 185, 202, 219, 236, 253, 270, 287, 304, 321, 337, 354, 371, 388, 405, 422, 439, 456, 458, 460, 462, or 464. In yet another embodiment, the polypeptide is selected from the group consisting of a polypeptide having at least 90% sequence identity to SEQ ID No. 2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID No. 462; at least 94% sequence identity to SEQ ID No. 36; at least 96% sequence identity to SEQ ID No. 460; at least 99% sequence identity to SEQ ID No. 464; at least 99.6% sequence identity to SEQ ID No. 458; and at least 99.7% sequence identity to SEQ ID No. 456.

In embodiments of the invention, the polypeptides may be acidophilic and/or thermophilic. In further embodiments, the polypeptides may be glycosylated, pegylated, and/or otherwise posttranslationally modified.

Embodiments of the invention include methods of at least partially degrading, cleaving, or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups. Such methods may comprise placing a polypeptide selected from the group consisting of a polypeptide having at least 90% sequence identity to SEQ ID No. 2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID No. 462; at least 94% sequence identity to SEQ ID No. 36; at least 96% sequence identity to SEQ ID No. 460; at least 99% sequence identity to SEQ ID No. 464; at least 99.6% sequence identity to SEQ ID No. 458; and at least 99.7% sequence identity to SEQ ID No. 456 in fluid contact with a polysaccharide, lignocellulose, cellulose, hemicellulose, lignin, starch, chitin, polyhydroxybutyrate, heteroxylans, glycoside, xylan-, glucan-, galactan-, and/or mannan-decorating group.

These and other aspects of the invention will become apparent to the skilled artisan in view of the teachings contained herein.

BRIEF DESCRIPTION OF THE SEVERAL VIEWS OF THE DRAWINGS

FIGS. 1A and 1B depict a sequence alignment between SEQ ID NO:2 (RAAC00169), an esterase of the alpha-beta hydrolase superfamily, and gi:121533815, gi:89099582, gi:16078568, gi:15615150, and gi:124524344 (SEQ ID NOs: 3-7 respectively) which are all esterases of the alpha-beta hydrolase superfamily. Amino acids common to three or more of the sequences aligned are indicated in bold.

FIGS. 2A and 2B depict a sequence alignment between SEQ ID NO: 19 (RAAC00501), an alpha beta hydrolase, gi:125974699, gi:15613871, gi:5457696, gi:14520481, and gi:40744233 and (SEQ ID NOs:20-24 respectively) which are all alpha beta hydrolases. Amino acids common to three or more of the sequences aligned are indicated in bold.

FIGS. 3A, 3B, and 3C depict a sequence alignment between SEQ ID NO:36 (RAAC00568), an alpha-glucosidase, and gi:6686567, gi:4586418, gi|89098051, and gi|114844717 (SEQ ID NOs:37-40 respectively) which are all alpha-glucosidases. Amino acids common to three or more of the sequences aligned are indicated in bold.

FIGS. 4A, 4B, and 4C depict a sequence alignment between SEQ ID NO:52 (RAAC00594) and gi|16131527, gi|52081844, gi|52787233, gi|16504867, and gi|16422318 (SEQ ID NOs:53-57 respectively) which are all alpha-xylosidases. Amino acids common to three or more of the sequences aligned are indicated in bold.

FIGS. 5A and 5B depict a sequence alignment between SEQ ID NO:69 (RAAC00602), an alpha-L-arabinofuranosidase, and gi:6079924, gi:89095985, gi:15614424, gi:52081375, and gi:52786751 (SEQ ID NOs:70-74 respectively) which are all alpha-L-arabinofuranosidases. Amino acids common to three or more of the sequences aligned are indicated in bold.

FIGS. 6A and 6B depict a sequence alignment between SEQ ID NO:86 (RAAC00798), a cell wall-associated hydrolase, and gi|15893601, gi|15896196, gi|15893600, and gi|116513351 (SEQ ID NOs:87-90 respectively) which are all cell wall-associated hydrolases. Amino acids common to three or more of the sequences aligned are indicated in bold.

FIGS. 7A and 7B depict a sequence alignment between SEQ ID NO:102 (RAAC001076), an altronate hydrolase, and gi|15613053, gi|121533397, gi|52081816, gi|52787203, and gi|15893984 (SEQ ID NOs:103-107 respectively) which are all altronate hydrolases. Amino acids common to three or more of the sequences aligned are indicated in bold.

FIGS. 8A and 8B depict a sequence alignment between SEQ ID NO: 119 (RAAC04341) and gi|125973125, gi|76796625, gi|20515428, gi|114843317, and gi|76795342 (SEQ ID NOs: 120-124 respectively) which are all cellulase/endoglucanase Ms. Amino acids common to three or more of the sequences aligned are indicated in bold.

FIGS. 9A and 9B depict a sequence alignment between SEQ ID NO:136 (RAAC04342) and gi|125973126, gi|20515429, gi|76796624, gi|114843316, and gi|15893508 (SEQ ID NOs:137-141 respectively) which are all cellulase/endoglucanase Ms. Amino acids common to three or more of the sequences aligned are indicated in bold.

FIG. 10 depicts a sequence alignment between SEQ ID NO:153 (RAAC04343), a cellulase/endoglucanase M, and gi:20515430, gi:76796623, gi:125973127, and gi:125973126 (SEQ ID NOs:154-156 and 137 respectively) which are all cellulase/endoglucanase Ms. Amino acids common to three or more of the sequences aligned are indicated in bold.

FIGS. 11A-11C depict a sequence alignment between SEQ ID NO:168 (RAAC01275), a polygalacturonase, and gi:89098529, gi:116623151, gi:116620373, gi:52081815, and gi:52787202 (SEQ ID NOs:169-173 respectively) which are all polygalacturonases. Amino acids common to three or more of the sequences aligned are indicated in bold.

FIGS. 12A-12C depict a sequence alignment between SEQ ID NO:185 (RAAC01615), an alpha-galactosidase, and gi|15614786, gi|90961985, gi|148544139, gi|76796346, and gi:114844315 (SEQ ID NOs:186-190 respectively) which are all alpha-galactosidases. Amino acids common to three or more of the sequences aligned are indicated in bold.

FIGS. 13A-13K depict a sequence alignment between SEQ ID NO:202 (RAAC01621), a cellobiose phosphorylase, and gi|125973736, gi|114844102, gi|20517160, gi|76795700, and gi|118725340 (SEQ ID NOs:203-207 respectively) which are all cellobiose phosphorylases. Amino acids common to three or more of the sequences aligned are indicated in bold.

FIGS. 14A-14C depict a sequence alignment between SEQ ID NO:219 (RAAC01755) and gi|15616253, gi|89099466, gi|17227827, gi|72163378, and gi|13470878 (SEQ ID NOs: 220-224 respectively) which are all glycogen debranching enzymes. Amino acids common to three or more of the sequences aligned are indicated in bold.

FIGS. 15A and 15B depict a sequence alignment between SEQ ID NO:236 (RAAC01887), a cellulase/endoglucanase M, and gi|52081384, gi|124521982, gi|89098880, gi|121533826, and gi|15615819 (SEQ ID NOs:237-240 respectively) which are all cellulase/endoglucanase Ms. Amino acids common to three or more of the sequences aligned are indicated in bold.

FIGS. 16A and 16B depict a sequence alignment between SEQ ID NO:253 (RAAC01897), an acetyl esterase/acetyl hydrolase, and gi|21221842, gi|13470513, gi|13471782, gi|16329563, and gi|15600577 (SEQ ID NOs:254-258 respectively) which are all acetyl esterase/acetyl hydrolases. Amino acids common to three or more of the sequences aligned are indicated in bold.

FIGS. 17A and 17B depict a sequence alignment between SEQ ID NO:270 (RAAC01917), a beta-1,4-xylanase, and gi|114054545, gi|134266943, gi|39654242, gi|61287936, and gi|3201483 (SEQ ID NOs:271-275 respectively) which are all beta-1,4-xylanases. Amino acids common to three or more of the sequences aligned are indicated in bold.

FIGS. 18A and 18B depict a sequence alignment between SEQ ID NO:287 (RAAC02404), a cinnamoyl ester hydrolase, and gi|76796576, gi|114845181, gi|15896898, gi|15806073, and gi|58448090 (SEQ ID NOs:288-292 respectively) which are all cinnamoyl ester hydrolases. Amino acids common to three or more of the sequences aligned are indicated in bold.

FIGS. 19A and 19B depict a sequence alignment between SEQ ID NO:304 (RAAC02424), a carboxylesterase type B, and gi|56421584, gi|134105165, gi|124521931, gi|33311865, and gi|138896639 (SEQ ID NOs:305-309 respectively) which are all carboxylesterase type Bs. Amino acids common to three or more of the sequences aligned are indicated in bold.

FIGS. 20A-20D depict a sequence alignment between SEQ ID NO:321 (RAAC02616), a beta galactosidase/beta-glucuronidase, and gi|29377189, gi|116493950, gi|40745013, and gi|49176308 (SEQ ID NOs:322-325 respectively) which are all beta galactosidase/beta-glucuronidases. Amino acids common to three or more of the sequences aligned are indicated in bold.

FIGS. 21A-21D depict a sequence alignment between SEQ ID NO:337 (RAAC02661), a xylan alpha-1,2-glucuronidase, and gi|15613624, gi|118725970, gi|148270004, gi|15642830, and gi|116621784 (SEQ ID NOs:338-342 respectively) which are all xylan alpha-1,2-glucuronidases. Amino acids common to three or more of the sequences aligned are indicated in bold.

FIGS. 22A-22C depict a sequence alignment between SEQ ID NO:354 (RAAC02925), a 3-hydroxyisobutyryl-CoA hydrolase, and gi|52080473, gi|17552962, gi|15292329, gi|66851010, and gi|40739053 (SEQ ID NOs:355-359 respectively) which are all 3-hydroxyisobutyryl-CoA hydrolases. Amino acids common to three or more of the sequences aligned are indicated in bold.

FIGS. 23A-23D depict a sequence alignment between SEQ ID NO:371 (RAAC03001), a beta-glucosidase B-related glycosidase, and gi|125973771, gi|116617985, gi|116494248 gi|116334524, and gi|66851551 (SEQ ID NOs:372-376 respectively) which are all beta-glucosidase B-related glycosidases. Amino acids common to three or more of the sequences aligned are indicated in bold.

FIGS. 24A and 24B depict a sequence alignment between SEQ ID NO:388 (RAAC02913), a chitooligosaccharide deacetylase, and gi|15614969, gi|124523066, gi|114843671 gi|89101184, and gi|2634042 (SEQ ID NOs:389-393 respectively) which are all chitooligosaccharide deacetylases. Amino acids common to three or more of the sequences aligned are indicated in bold.

FIGS. 25A and 25B depict a sequence alignment between SEQ ID NO:405 (RAAC02839), a chitooligosaccharide deacetylase, and gi|1595264, gi|20803949, gi|17380381 gi|128438, and gi|1001913 (SEQ ID NOs:406-409 respectively) which are all chitooligosaccharide deacetylases. Amino acids common to three or more of the sequences aligned are indicated in bold.

FIGS. 26A-26C depict a sequence alignment between SEQ ID NO:422 (RAAC00961), a chitooligosaccharide deacetylase, and gi|124523411, gi|158060979, gi|21219643 gi|13475158, and gi|21219455 (SEQ ID NOs:423-427 respectively) which are all chitooligosaccharide deacetylases. Amino acids common to three or more of the sequences aligned are indicated in bold.

FIGS. 27A and 27B depict a sequence alignment between SEQ ID NO:439 (RAAC00361), a chitooligosaccharide deacetylase, and gi|52078651, gi|16077225, gi|89100395 gi|15612806, and gi|121535454 (SEQ ID NOs:440-444 respectively) which are all chitooligosaccharide deacetylases. Amino acids common to three or more of the sequences aligned are indicated in bold.

DETAILED DESCRIPTION OF THE INVENTION

Lignocellulose is a highly heterogeneous 3-dimensional matrix comprised primarily of cellulose, hemicellulose, and lignin. Many fuels and chemicals can be made from these lignocellulosic materials. To utilize lignocellulosic biomass for production of fuels and chemicals via fermentative processes, it is necessary to convert the plant polysaccharides to sugar monomers which are then fermented to products using a variety of microorganisms. Direct hydrolysis of lignocellulose by mineral acids to monomers is possible at high temperature and pressure, leading to yield losses due to thermal decomposition of the sugars. Utilizing existing commercially available enzymes, a first strategy to reduce these yield losses is to perform the pretreatment at reduced severity to produce soluble oligomers, followed by the use of use cellulases and hemicellulases to depolymerize the polysaccharides at moderate temperatures. In a second approach, the addition of acid stable thermotolerant hydrolytic enzymes including cellulases, xylanases and other hemicellulases to the biomass slurry during the pretreatment allows the use of further reduced temperatures and pressures during the pretreatment, as well as cheaper materials of construction, reducing both the capital and energy costs. An extension of this second approach is to combine the enzyme-assisted reduced severity pretreatment together with fermentation under the same conditions, which further reduces costs.

For commercially available enzymes to be utilized, strategy 1 must be used. The second approach represents a significant improvement in the art because the pretreatment and bioconversion of the polysaccharides to products can be achieved in fewer steps/vessels and without intermediately altering the process conditions.

Embodiments of the invention relate in part to the gene sequences and protein sequences encoded by genes of *Alicyclobacillus acidocaldarius*. Genes included are those necessary to depolymerize biopolymers including lignocellulosic polysaccharides, starches, chitin, polyhydroxybutyrate and the like to monomers or oligomers. Intracellular enzyme activities will be thermophilic in nature and general examples of similar genes are described in the literature. Extracellular enzyme activities will be thermoacidophilic (simultaneously thermophilic and acidophilic). The following classes of enzymes are included for polysaccharide depolymerization: glycosyl hydrolases (or glycoside hydrolases); esterases including acetylxylan esterases and p-cumaric acid esterases and ferulic acid esterases; and uronidases. An additional class of enzymes for biopolymer depolymerization includes polyhydroxybutyrate-degrading enzymes.

The present invention relates to isolated and/or purified nucleotide sequences of the genome of *Alicyclobacillus acidocaldarius* selected from the sequences SEQ ID Nos. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or one of their fragments.

The present invention likewise relates to isolated and/or purified nucleotide sequences, characterized in that they are selected from: a) a nucleotide sequence of a specific fragment of the sequence SEQ ID Nos. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or one of their fragments; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide, or nucleic acid sequence will be understood according to the present invention as meaning both a double-stranded or single-stranded DNA in the monomeric and dimeric (so-called in tandem) forms and the transcription products of said DNAs.

Aspects of the invention relate nucleotide sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning, and subcloning, it being possible for the sequences of the invention to be carried by vectors.

Isolated and/or purified nucleotide sequence fragment according to the invention will be understood as designating any nucleotide fragment of the genome of *Alicyclobacillus acidocaldarius*, and may include, by way of non-limiting examples, length of at least 8, 12, 20, 25, 50, 75, 100, 200, 300, 400, 500, 1000, or more, consecutive nucleotides of the sequence from which it originates.

Specific fragment of an isolated and/or purified nucleotide sequence according to the invention will be understood as designating any nucleotide fragment of the genome of *Alicyclobacillus acidocaldarius*, having, after alignment and comparison with the corresponding fragments of genomic sequences of *Alicyclobacillus acidocaldarius*, at least one nucleotide or base of different nature.

Homologous isolated and/or purified nucleotide sequence in the sense of the present invention is understood as meaning isolated and/or purified a nucleotide sequence having at least a percentage identity with the bases of a nucleotide sequence according to the invention of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

Specific homologous nucleotide sequence in the sense of the present invention is understood as meaning a homologous nucleotide sequence having at least one nucleotide sequence of a specific fragment, such as defined above. Said "specific" homologous sequences can comprise, for example, the sequences corresponding to the genomic sequence or to the sequences of its fragments representative of variants of the genome of *Alicyclobacillus acidocaldarius*. These specific homologous sequences can thus correspond to variations linked to mutations within strains of *Alicyclobacillus acidocaldarius*, and especially correspond to truncations, substitutions, deletions and/or additions of at least one nucleotide. Said homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotidic sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2: 482 (1981), by the homology alignment algorithm of Neddleman and Wunsch, *J. Mol. Biol.* 48: 443 (1970), by the search for similarity method of Pearson and Lipman, *Proc. Natl. Acad. Sci.* (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

In the BLAST N or BLAST P "BLAST 2 sequence", software which is available in the web ncbi.nlm.nih.gov/gorf/bl2.html, and habitually used by the inventors and in general by the skilled person for comparing and determining the identity between two sequences, gap cost which depends on the sequence length to be compared is directly selected by the software (i.e. 11.2 for substitution matrix BLOSUM-62 for length>85).

Complementary nucleotide sequence of a sequence of the invention is understood as meaning any DNA whose nucleotides are complementary to those of the sequence of the invention, and whose orientation is reversed (antisense sequence).

Hybridization under conditions of stringency with a nucleotide sequence according to the invention is understood as meaning hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2'SSC, 0.5% SDS at 65° C.; 2×0.5'SSC, 0.5% SDS; at 65° C. for 10 minutes each.

The conditions of intermediate stringency, using, for example, a temperature of 42° C. in the presence of a 2×SSC buffer, or of less stringency, for example a temperature of 37° C. in the presence of a 2×SSC buffer, respectively require a globally less significant complementarity for the hybridization between the two sequences.

The stringent hybridization conditions described above for a polynucleotide with a size of approximately 350 bases will be adapted by the person skilled in the art for oligonucleotides of greater or smaller size, according to the teaching of Sambrook et al., 1989.

Among the isolated and/or purified nucleotide sequences according to the invention, are those which can be used as a primer or probe in methods allowing the homologous sequences according to the invention to be obtained, these methods, such as the polymerase chain reaction (PCR), nucleic acid cloning, and sequencing, being well known to the person skilled in the art.

Among said isolated and/or purified nucleotide sequences according to the invention, those are again preferred which can be used as a primer or probe in methods allowing the presence of SEQ ID Nos. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463, one of their fragments, or one of their variants such as defined below to be diagnosed.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Such representative fragments can likewise be obtained by chemical synthesis according to methods well known to persons of ordinary skill in the art.

Modified nucleotide sequence will be understood as meaning any nucleotide sequence obtained by mutagenesis according to techniques well known to the person skilled in the art, and containing modifications with respect to the normal sequences according to the invention, for example mutations in the regulatory and/or promoter sequences of polypeptide expression, especially leading to a modification of the rate of expression of said polypeptide or to a modulation of the replicative cycle.

Modified nucleotide sequence will likewise be understood as meaning any nucleotide sequence coding for a modified polypeptide such as defined below.

The present invention relates to isolated and/or purified nucleotide sequences of *Alicyclobacillus acidocaldarius*, characterized in that they are selected from the sequences SEQ ID Nos. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or one of their fragments.

Embodiments of the invention likewise relate to isolated and/or purified nucleotide sequences characterized in that they comprise a nucleotide sequence selected from: a) a nucleotide sequence SEQ ID Nos. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or one of their fragments or one of their fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the isolated and/or purified nucleotide sequences according to the invention are the nucleotide sequences of SEQ ID Nos. 8-12, 25-29, 41-45, 58-62, 75-79, 91-95, 108-112, 125-129, 142-146, 157-161, 174-178, 191-195, 208-212, 225-229, 242-246, 259-263, 276-280, 293-297, 310-314, 326-330, 343-347, 360-364, 377-381, 394-398, 411-415, 428-432, or 445-449 or fragments thereof and any other isolated and/or purified nucleotide sequences which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the sequence SEQ ID Nos. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463 or fragments thereof. Said homologous sequences can comprise, for example, the sequences corresponding to the genomic sequences *Alicyclobacillus acidocaldarius*. In the same manner, these specific homologous sequences can correspond to variations linked to mutations within strains of *Alicyclobacillus acidocaldarius* and especially correspond to truncations, substitutions, deletions and/or additions of at least one nucleotide.

Embodiments of the invention comprise the isolated and/or purified polypeptides encoded by a nucleotide sequence according to the invention, or fragments thereof, whose sequence is represented by a fragment. Amino acid sequences corresponding to the isolated and/or purified polypeptides which can be encoded according to one of the three possible reading frames of the sequence SEQ ID Nos. 1, 18, 35, 51, 68, 85, 101, 118, 135, 152, 167, 184, 201, 218, 235, 252, 269, 286, 303, 320, 336, 353, 370, 387, 404, 421, 438, 455, 457, 459, 461, or 463.

Embodiments of the invention likewise relate to the isolated and/or purified polypeptides, characterized in that they comprise a polypeptide selected from the amino acid sequences SEQ Nos. 2, 19, 52, 69, 86, 102, 119, 136, 153, 168, 185, 202, 219, 236, 253, 270, 287, 304, 321, 337, 354, 371, 388, 405, 422, 439, 456, 458, 460, 462, or 464 or one of their fragments.

Among the isolated and/or purified polypeptides, according to embodiments of the invention, are the isolated and/or purified polypeptides of amino acid sequence SEQ ID Nos. 13-17, 30-34, 46-50, 63-67, 80-84, 96-100, 113-117, 130-134, 147-151, 162-166, 179-183, 196-200, 213-217, 230-234, 247-251, 264-268, 281-285, 298-302, 315-319, 331-335, 348-352, 365-369, 382-386, 399-403, 416-420, 433-437, or 450-454 or fragments thereof or any other isolated and/or purified polypeptides which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the sequence SEQ ID Nos. 2, 19, 52, 69, 86, 102, 119, 136, 153, 168, 185, 202, 219, 236, 253, 270, 287, 304, 321, 337, 354, 371, 388, 405, 422, 439, 456, 458, 460, 462, or 464 or fragments thereof.

Embodiments of the invention also relate to the polypeptides, characterized in that they comprise a polypeptide selected from: a) a specific fragment of at least 5 amino acids of a polypeptide of an amino acid sequence according to the invention; b) a polypeptide homologous to a polypeptide such as defined in a); c) a specific biologically active fragment of a polypeptide such as defined in a) or b); and d) a polypeptide modified by a polypeptide such as defined in a), b) or c).

In the present description, the terms polypeptide, peptide and protein are interchangeable.

In embodiments of the invention, the isolated and/or purified polypeptides according to the invention may be glycosylated, pegylated, and/or otherwise posttranslationally modified. In further embodiments, glycosylation, pegylation, and/or other posttranslational modifications may occur in vivo or in vitro and/or may be performed using chemical techniques. In additional embodiments, any glycosylation, pegylation and/or other posttranslational modifications may be N-linked or O-linked.

In embodiments of the invention the any one of the isolated and/or purified polypeptides according to the invention may enzymatically active at temperatures at or above about 25, 30, 35, 40, 45, 50, 55, 60, 65, 70, 75, 80, 85, 90, and/or 95 degrees Celsius and/or may be enzymatically active at a pH at, below, and/or above 7, 6, 5, 4, 3, 2, 1, and/or 0. In further embodiments of the invention, glycosylation, pegylation, and/or other posttranslational modification may be required for the isolated and/or purified polypeptides according to the invention to be enzymatically active at pH at or below 7, 6, 5, 4, 3, 2, 1, and/or 0 or at a temperatures at or above about 25, 30, 35, 40, 45, 50, 55, 60, 65, 70, 75, 80, 85, 90, and/or 95 degrees Celsius.

Aspects of the invention relate to polypeptides that are isolated or obtained by purification from natural sources, or else obtained by genetic recombination, or alternatively by chemical synthesis and that they may thus contain unnatural amino acids, as will be described below.

A "polypeptide fragment" according to the embodiments of the invention is understood as designating a polypeptide containing at least 5 consecutive amino acids, preferably 10 consecutive amino acids or 15 consecutive amino acids.

In the present invention, a specific polypeptide fragment is understood as designating the consecutive polypeptide fragment encoded by a specific fragment nucleotide sequence according to the invention.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 80% or 90%, homology with the sequences of amino acids of polypeptides according to the invention.

"Specific homologous polypeptide" will be understood as designating the homologous polypeptides such as defined above and having a specific fragment of polypeptide according to the invention.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. Examples of such substitutions in the amino acid sequences SEQ ID Nos. 2, 19, 52, 69, 86, 102, 119, 136, 153, 168, 185, 202, 219, 236, 253, 270, 287, 304, 321, 337, 354, 371, 388, 405, 422, 439, 456, 458, 460, 462, or 464 may include those isolated and/or purified polypeptides of amino acid sequence SEQ ID Nos. 13-17, 30-34, 46-50, 63-67, 80-84, 96-100, 113-117, 130-134, 147-151, 162-166, 179-183, 196-200, 213-217, 230-234, 247-251, 264-268, 281-285, 298-302, 315-319, 331-335, 348-352, 365-369, 382-386, 399-403, 416-420, 433-437, or 450-454.

These equivalent amino acids can be determined either by depending on their structural homology with the amino acids which they substitute, or on results of comparative tests of biological activity between the different polypeptides, which are capable of being carried out.

By way of nonlimiting example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

In a further embodiment, substitutions are limited to substitutions in amino acids not conserved among other proteins which have similar identified enzymatic activity. For example, the Figures herein provide sequence alignments between certain polypeptides of the invention and other polypeptides identified as having similar enzymatic activity, with amino acids common to three or more of the sequences aligned are indicated in bold. Thus, according to one embodiment of the invention, substitutions or mutation may be made at positions that are not indicated as in bold in figures. Examples of such polypeptides may include, but are not limited to, those found in amino acid sequence SEQ ID Nos. 13-17, 30-34, 46-50, 63-67, 80-84, 96-100, 113-117, 130-134, 147-151, 162-166, 179-183, 196-200, 213-217, 230-234, 247-251, 264-268, 281-285, 298-302, 315-319, 331-335, 348-352, 365-369, 382-386, 399-403, 416-420, 433-437, or 450-454. In a further embodiment, nucleic acid sequences may be mutated or substituted such that the amino acid they encode is unchanged (degenerate substitutions and/or mutations) and/or mutated or substituted such that any resulting amino acid substitutions or mutation are made at positions that are not indicated as in bold in figures. Examples of such nucleic acid sequences may include, but are not limited to, those found in are the nucleotide sequences of SEQ ID Nos. 13-17, 30-34, 46-50, 63-67, 80-84, 96-100, 113-117, 130-134, 147-151, 162-166, 179-183, 196-200, 213-217, 230-234, 247-251, 264-268, 281-285, 298-302, 315-319, 331-335, 348-352, 365-369, 382-386, 399-403, 416-420, 433-437, or 450-454 or fragments thereof.

The specific homologous polypeptides likewise correspond to polypeptides encoded by the specific homologous nucleotide sequences such as defined above and thus comprise in the present definition the polypeptides which are mutated or correspond to variants which can exist in *Alicyclobacillus acidocaldarius*, and which especially correspond to truncations, substitutions, deletions, and/or additions of at least one amino acid residue.

"Specific biologically active fragment of a polypeptide" according to an embodiment of the invention will be understood in particular as designating a specific polypeptide fragment, such as defined above, having at least one of the characteristics of polypeptides according to the invention. In certain embodiments the peptide is capable of acting as an Alpha beta hydrolase, Alpha-glucosidase, Glucan 1,4-alpha-maltohydrolase, Glycosidase, Amylase, Acetyl esterase, Beta-galactosidase, Alpha amylase, Acetyl esterase, Alpha-xylosidase, Cyclomaltodextrinase; Neopullulinase; Maltogenic alpha-amylase, Family 31 of glycosyl hydrolase, Alpha-L-arabinofuranosidase, Cell wall hydrolase, Altronate hydrolase, poly-1,4-alpha-D-galacturonide, Xylan alpha-1,2-glucuronosidase, Cellulase/Endoglucanase M, Polygalacturonase, Glycosyl hydrolase, Peptidoglycan hydrolase, N-acetylglucosaminidase, Endochitinase, Alpha-galactosidase, Endo-beta-1,4-mannanase, Cellobiose phosphorylase, Cyclic beta-1,2-glucan synthase, Glycogen debranching enzyme, Acetyl hydrolase, Beta-1,4-xylanase, Beta-glucosidase, 6-phospho-beta-glucosidase, Cinnamoyl ester hydrolase, Beta-glucuronidase, Xylan alpha-1,2-glucuronosidase, 3-hydroxyisobutyryl-CoA hydrolase, Beta-glucosidase B-related glycosidase, and/or Chitooligosaccharide deacetylase.

The polypeptide fragments according to embodiments of the invention can correspond to isolated or purified fragments naturally present in a *Alicyclobacillus acidocaldarius* or correspond to fragments which can be obtained by cleavage of said polypeptide by a proteolytic enzyme, such as trypsin or chymotrypsin or collagenase, or by a chemical reagent, such as cyanogen bromide (CNBr). Such polypeptide fragments can likewise just as easily be prepared by chemical synthesis, from hosts transformed by an expression vector according to the invention containing a nucleic acid allowing the expression of said fragments, placed under the control of appropriate regulation and/or expression elements.

"Modified polypeptide" of a polypeptide according to an embodiment of the invention is understood as designating a polypeptide obtained by genetic recombination or by chemical synthesis as will be described below, having at least one modification with respect to the normal sequence. These modifications may or may not be able to bear on amino acids at the origin of specificity, and/or of activity, or at the origin of the structural conformation, localization, and of the capacity of membrane insertion of the polypeptide according to the invention. It will thus be possible to create polypeptides of equivalent, increased, or decreased activity, and of equivalent, narrower, or wider specificity. Among the modified polypeptides, it is necessary to mention the polypeptides in which up to 5 amino acids can be modified, truncated at the N- or C-terminal end, or even deleted or added.

The methods allowing said modulations on eukaryotic or prokaryotic cells to be demonstrated are well known to the person of ordinary skill in the art. It is likewise well understood that it will be possible to use the nucleotide sequences coding for said modified polypeptides for said modulations, for example through vectors according to the invention and described below.

The preceding modified polypeptides can be obtained by using combinatorial chemistry, in which it is possible to systematically vary parts of the polypeptide before testing them on models, cell cultures or microorganisms for example, to select the compounds which are most active or have the properties sought.

Chemical synthesis likewise has the advantage of being able to use unnatural amino acids, or nonpeptide bonds.

Thus, in order to improve the duration of life of the polypeptides according to the invention, it may be of interest to use unnatural amino acids, for example in D form, or else amino acid analogs, especially sulfur-containing forms, for example.

Finally, it will be possible to integrate the structure of the polypeptides according to the invention, its specific or modified homologous forms, into chemical structures of polypeptide type or others. Thus, it may be of interest to provide at the N- and C-terminal ends compounds not recognized by proteases.

The nucleotide sequences coding for a polypeptide according to the invention are likewise part of the invention.

The invention likewise relates to nucleotide sequences utilizable as a primer or probe, characterized in that said sequences are selected from the nucleotide sequences according to the invention.

It is well understood that the present invention, in various embodiments, likewise relates to specific polypeptides of *Alicyclobacillus acidocaldarius*, encoded by nucleotide sequences, capable of being obtained by purification from natural polypeptides, by genetic recombination or by chemical synthesis by procedures well known to the person skilled in the art and such as described in particular below. In the same manner, the labeled or unlabeled mono- or polyclonal antibodies directed against said specific polypeptides encoded by said nucleotide sequences are also encompassed by the invention.

Embodiments of the invention additionally relate to the use of a nucleotide sequence according to the invention as a primer or probe for the detection and/or the amplification of nucleic acid sequences.

The nucleotide sequences according to embodiments of the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially at least 20 nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); the TMA technique (Transcription Mediated Amplification).

The polynucleotides of the invention can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al. as well as by Stone et al. in 1996.

In the case where the target polynucleotide to be detected is possibly an RNA, for example an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

Embodiments of the invention also comprise the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive element (32P, 35S, 3H, 125I) or with a nonradioactive molecule (biotin, acetylaminofluorene, digoxigenin, 5-bromodeoxyuridine, fluorescein) to obtain probes which are utilizable for numerous applications.

Examples of nonradioactive labeling of nucleotide sequences are described, for example, in French Patent No. 78.10975 or by Urdea et al. or by Sanchez-Pescador et al. in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention, in various embodiments, likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between said capture probe and the target nucleic acid is then detected with the aid of a second probe, a so-called detection probe, labeled with an easily detectable element.

Another aspect of the present invention is a vector for the cloning and/or expression of a sequence, characterized in that it contains a nucleotide sequence according to the invention.

The vectors according to the invention, characterized in that they contain the elements allowing the expression and/or the secretion of said nucleotide sequences in a determined host cell, are likewise part of the invention.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences according to the invention may be inserted into autonomous replication vectors within the chosen host, or integrated vectors of the chosen host.

Such vectors will be prepared according to the methods currently used by the person skilled in the art, and it will be possible to introduce the clones resulting therefrom into an appropriate host by standard methods, such as, for example, lipofection, electroporation, and thermal shock.

The vectors according to the invention are, for example, vectors of plasmid or viral origin. One example of a vector for the expression of polypeptides of the invention is baculovirus.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector such as defined above, then the culturing of said cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as plants cells, such as *Arabidopsis* sp., and animal cells, in particular the cultures of mammalian cells (Edwards and Aruffo, 1993), for example, Chinese hamster ovary (CHO) cells, but likewise the cells of insects in which it is possible to use procedures employing baculoviruses, for example sf9 insect cells (Luckow, 1993).

Embodiments of the invention likewise relate to organisms comprising one of said transformed cells according to the invention.

The obtainment of transgenic organisms according to the invention overexpressing one or more of the genes of *Alicyclobacillus acidocaldarius* or part of the genes may be carried out in, for example, rats, mice, or rabbits according to methods well known to the person skilled in the art, such as by viral or nonviral transfections. It will be possible to obtain the transgenic organisms overexpressing one or more of said genes by transfection of multiple copies of said genes under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of said chimeras.

The transformed cells as well as the transgenic organisms according to the invention are utilizable in procedures for preparation of recombinant polypeptides.

It is today possible to produce recombinant polypeptides in relatively large quantity by genetic engineering using the cells transformed by expression vectors according to the invention or using transgenic organisms according to the invention.

The procedures for preparation of a polypeptide of the invention in recombinant form, characterized in that they employ a vector and/or a cell transformed by a vector according to the invention and/or a transgenic organism comprising one of said transformed cells according to the invention are themselves comprised in the present invention.

As used herein, "transformation" and "transformed" relate to the introduction of nucleic acids into a cell, whether prokaryotic or eukaryotic. Further, "transformation" and "transformed," as used herein, need not relate to growth control or growth deregulation.

Among said procedures for preparation of a polypeptide of the invention in recombinant form, the preparation procedures employing a vector, and/or a cell transformed by said vector and/or a transgenic organism comprising one of said transformed cells, containing a nucleotide sequence according to the invention coding for a polypeptide of *Alicyclobacillus acidocaldarius*.

A variant according to the invention may consist of producing a recombinant polypeptide fused to a "carrier" protein (chimeric protein). The advantage of this system is that it may allow stabilization of and/or a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps: a) culture of transformed cells under conditions allowing the expression of a recombinant polypeptide of nucleotide sequence according to the invention; b) if need be, recovery of said recombinant polypeptide.

When the procedure for preparation of a polypeptide of the invention employs a transgenic organism according to the invention, the recombinant polypeptide is then extracted from said organism.

The invention also relates to a polypeptide which is capable of being obtained by a procedure of the invention such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques which are conventional in the field of the synthesis of peptides. This synthesis can be carried out in homogeneous solution or in solid phase.

For example, recourse can be made to the technique of synthesis in homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

Recourse may also be made to the technique described by Merrifield.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids which are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated, pegylated, and/or otherwise posttranslationally modified form used with a view to obtaining immunogenic compositions capable of inducing the synthesis of antibodies directed against multiple epitopes.

These hybrid molecules can be formed, in part, of a polypeptide carrier molecule or of fragments thereof according to the invention, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

Said hybrid nucleotide sequences coding for a hybrid polypeptide as well as the hybrid polypeptides according to the invention characterized in that they are recombinant polypeptides obtained by the expression of said hybrid nucleotide sequences are likewise part of the invention.

The invention likewise comprises the vectors characterized in that they contain one of said hybrid nucleotide sequences. The host cells transformed by said vectors, the transgenic organisms comprising one of said transformed cells as well as the procedures for preparation of recombinant polypeptides using said vectors, said transformed cells and/or said transgenic organisms are, of course, likewise part of the invention.

The polypeptides according to the invention, the antibodies according to the invention described below and the nucleotide sequences according to the invention can advantageously be employed in procedures for the detection and/or identification of *Alicyclobacillus acidocaldarius*, in a sample capable of containing them. These procedures, according to the specificity of the polypeptides, the antibodies and the nucleotide sequences according to the invention which will be used, will in particular be able to detect and/or to identify a *Alicyclobacillus acidocaldarius*.

The polypeptides according to the invention can advantageously be employed in a procedure for the detection and/or the identification of *Alicyclobacillus acidocaldarius* in a sample capable of containing them, characterized in that it comprises the following steps: a) contacting of this sample with a polypeptide or one of its fragments according to the invention (under conditions allowing an immunological reaction between said polypeptide and the antibodies possibly present in the biological sample); b) demonstration of the antigen-antibody complexes possibly formed.

Any conventional procedure can be employed for carrying out such a detection of the antigen-antibody complexes possibly formed.

By way of example, a preferred method brings into play immunoenzymatic processes according to the ELISA technique, by immunofluorescence, or radioimmunological processes (RIA) or their equivalent.

Thus, the invention likewise relates to the polypeptides according to the invention, labeled with the aid of an adequate label such as of the enzymatic, fluorescent or radioactive type.

Such methods comprise, for example, the following steps: deposition of determined quantities of a polypeptide composition according to the invention in the wells of a microtiter plate, introduction into said wells of increasing dilutions of serum, or of a biological sample other than that defined previously, having to be analyzed, incubation of the microplate, introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example at 550 nm, detection, by comparison with a control test, of the quantity of hydrolyzed substrate.

The polypeptides according to the invention allow monoclonal or polyclonal antibodies to be prepared which are characterized in that they specifically recognize the polypeptides according to the invention. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide which has served as an antigen has previously been immobilized. The polyclonal antibodies according to the invention can also be prepared by purification, on an affinity column on which a polypeptide according to the invention has previously been immobilized, of the antibodies contained in the serum of an animal immunoligically challenged by *Alicyclobacillus acidocaldarius*, or a polypeptide or fragment according to the invention.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of *Alicyclobacillus acidocaldarius* in a sample, characterized in that it comprises the following steps: a) contacting of the sample with a mono- or polyclonal antibody according to the invention (under conditions allowing an immunological reaction between said antibodies and the polypeptides of *Alicyclobacillus acidocaldarius* possibly present in the biological sample); b) demonstration of the antigen-antibody complex possibly formed.

The present invention likewise relates to a procedure for the detection and/or the identification of *Alicyclobacillus acidocaldarius* in a sample, characterized in that it employs a nucleotide sequence according to the invention.

More particularly, the invention relates to a procedure for the detection and/or the identification of *Alicyclobacillus acidocaldarius* in a sample, characterized in that it contains the following steps: a) if need be, isolation of the DNA from the sample to be analyzed; b) specific amplification of the DNA of the sample with the aid of at least one primer, or a pair of primers, according to the invention; c) demonstration of the amplification products.

These can be detected, for example, by the technique of molecular hybridization utilizing a nucleic probe according to the invention. This probe will advantageously be labeled with a nonradioactive (cold probe) or radioactive element.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in said biological sample.

A further embodiment of the invention comprises a method, characterized in that it comprises the following steps: a) contacting of a nucleotide probe according to the invention with a biological sample, the DNA contained in the biological sample having, if need be, previously been made accessible to hybridization under conditions allowing the hybridization of the probe with the DNA of the sample; b) demonstration of the hybrid formed between the nucleotide probe and the DNA of the biological sample.

The present invention also relates to a procedure according to the invention, characterized in that it comprises the following steps: a) contacting of a nucleotide probe immobilized on a support according to the invention with a biological sample, the DNA of the sample having, if need be, previously been made accessible to hybridization, under conditions allowing the hybridization of the probe with the DNA of the sample; b) contacting of the hybrid formed between the nucleotide probe immobilized on a support and the DNA contained in the biological sample, if need be after elimination of the DNA of the biological sample which has not hybridized with the probe, with a nucleotide probe labeled according to the invention; c) demonstration of the novel hybrid formed in step b).

According to an advantageous embodiment of the procedure for detection and/or identification defined previously, this is characterized in that, prior to step a), the DNA of the biological sample is first amplified with the aid of at least one primer according to the invention.

Further embodiments of the invention comprise methods of at least partially degrading, cleaving, and/or removing a polysaccharide, lignocellulose, cellulose, hemicellulose, lignin, starch, chitin, polyhydroxybutyrate, heteroxylan, glycosides, xylan-, glucan-, galactan, and/or mannan-decorating group. Degrading, cleaving, and/or removing these structures have art recognized utility such as those described in Mielenz 2001; Jeffries 1996; Shallom and Shoham 2003; Lynd et al. 2002; Vieille and Zeikus 2001; Bertoldo et al. 2004; and/or Malherbe and Cloete 2002.

Embodiments of methods include placing a recombinant, purified, and/or isolated polypeptide selected from the group consisting of a polypeptide having at least 90% sequence identity to SEQ ID No. 2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID No. 462; at least 94% sequence identity to SEQ ID No. 36; at least 96% sequence identity to SEQ ID No. 460; at least 99% sequence identity to SEQ ID No. 464; at least 99.6% sequence identity to SEQ ID No. 458; and at least 99.7% sequence identity to SEQ ID No. 456 in fluid contact with a polysaccharide, lignocellulose, cellulose, hemicellulose, lignin, starch, chitin, polyhydroxybutyrate, heteroxylans, glycoside, xylan-, glucan-, galactan, and/or mannan-decorating group.

Further embodiments of methods include placing a cell producing or encoding a recombinant, purified, and/or isolated polypeptide selected from the group consisting of a polypeptide having at least 90% sequence identity to SEQ ID No. 2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID No. 462; at least 94% sequence identity to SEQ ID No. 36; at least 96% sequence identity to SEQ ID No. 460; at least 99% sequence identity to SEQ ID No. 464; at least 99.6% sequence identity to SEQ ID No. 458; and at least 99.7% sequence identity to SEQ ID No. 456 in fluid contact with a polysaccharide, lignocellulose, cellulose, hemicellulose, lignin, starch, chitin, polyhydroxybutyrate, heteroxylans, glycoside, xylan-, glucan-, galactan, and/or mannan-decorating group.

As used herein, "partially degrading" relates to the rearrangement or cleavage of chemical bonds in the target structure.

In additional embodiments, methods of at least partially degrading, cleaving, and/or removing a polysaccharide, lignocellulose, cellulose, hemicellulose, lignin, starch, chitin, polyhydroxybutyrate, heteroxylan, glycosides, xylan-, glucan-, galactan, and/or mannan-decorating group may take place at temperatures at or above about 25, 30, 35, 40, 45, 50, 55, 60, 65, 70, 75, 80, 85, 90, and/or 95 degrees Celsius and/or at a pH at, below, and/or above 7, 6, 5, 4, 3, 2, 1, and/or 0.

Further embodiments of the invention may comprise a kit for at least partially degrading, cleaving, and/or removing a polysaccharide, lignocellulose, cellulose, hemicellulose, lignin, starch, chitin, polyhydroxybutyrate, heteroxylan, glycosides, xylan-, glucan-, galactan, and/or mannan-decorating group, the kit comprising a cell producing or encoding a recombinant, purified, and/or isolated a polypeptide selected from the group consisting of a polypeptide having at least 90% sequence identity to SEQ ID No. 2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID No. 462; at least 94% sequence identity to SEQ ID No. 36; at least 96% sequence identity to SEQ ID No. 460; at least 99% sequence identity to SEQ ID No. 464; at least 99.6% sequence identity to SEQ ID No. 458; and at least 99.7% sequence identity to SEQ ID No. 456 and/or a recombinant, purified, and/or isolated a polypeptide selected from the group consisting of a polypeptide having at least 90% sequence identity to SEQ ID No. 2, 19, 52, 69, 86, 102, 119, 136, 153, 168, 185, 202, 219, 236, 253, 270, 287, 304, 321, 337, 354, 371, 388, 405, 422, or 439; at least 93% sequence identity to SEQ ID No. 462; at least 94% sequence identity to SEQ ID No. 36; at least 96% sequence identity to SEQ ID No. 460; at least 99% sequence identity to SEQ ID No. 464; at least 99.6% sequence identity to SEQ ID No. 458; and at least 99.7% sequence identity to SEQ ID No. 456.

The invention is described in additional detail in the following illustrative examples. Although the examples may represent only selected embodiments of the invention, it should be understood that the following examples are illustrative and not limiting.

In embodiments of the invention the any one of the isolated and/or purified polypeptides according to the invention may enzymatically active at temperatures at or above about 25, 30, 35, 40, 45, 50, 55, 60, 65, 70, 75, 80, 85, 90, and/or 95 degrees Celsius and/or may be enzymatically active at a pH at, below, and/or above 7, 6, 5, 4, 3, 2, 1, and/or 0. In further embodiments of the invention, glycosylation, pegylation, and/or other posttranslational modification may be required for the isolated and/or purified polypeptides according to the invention to be enzymatically active at pH at or below 7, 6, 5, 4, 3, 2, 1, and/or 0 or at a temperatures at or above about 25, 30, 35, 40, 45, 50, 55, 60, 65, 70, 75, 80, 85, 90, and/or 95 degrees Celsius.

EXAMPLES

Example 1

RAAC00169: an Esterase of the Alpha-Beta Hydrolase Superfamily

Provided in SEQ ID NO:1 is a nucleotide sequence isolated from *Alicyclobacillus acidocaldarius* and encoding the polypeptide of SEQ ID NO:2. As can be seen in FIGS. 1A and 1B, SEQ ID NO:2 aligns well with other proteins identified as esterases of the alpha-beta hydrolase superfamily. Of particular importance, it is noted that where amino acids are conserved in other esterases of the alpha-beta hydrolase superfamily, those amino acids are generally conserved in SEQ ID NO:2. Thus, the polypeptide provided in SEQ ID NO:2 is properly classified as an esterase of the alpha-beta hydrolase superfamily.

The polypeptides of SEQ ID NOs:13-17 are representative examples of conservative substitutions in the polypeptide of SEQ ID NO:2 and are encoded by nucleotide sequences of SEQ ID NOs:8-12, respectively.

The nucleotide sequences of SEQ ID NOs:1 and 8-12 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 1 and 8-12 produce the polypeptides of SEQ ID NOs: 2 and 13-17. The polypeptides of SEQ ID NOs: 2 and 13-17 are then isolated and/or purified. The isolated and/or purified polypeptides of SEQ ID NOs: 2 and 13-17 are then demonstrated to have activity as esterases.

The isolated and/or purified polypeptides of SEQ ID NOs: 2 and 13-17 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 2 and 13-17 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 2

RAAC00501: an Alpha-Beta Hydrolase

Provided in SEQ ID NO:18 is a nucleotide sequence isolated from *Alicyclobacillus acidocaldarius* and encoding the polypeptide of SEQ ID NO:19. As can be seen in FIGS. 2A and 2B, SEQ ID NO:19 aligns well with other proteins identified as alpha-beta hydrolases. Of particular importance, it is noted that where amino acids are conserved in other alpha-beta hydrolases, those amino acids are generally conserved in SEQ ID NO:19. Thus, the polypeptide provided in SEQ ID NO:19 is properly classified as an alpha-beta hydrolase.

The polypeptides of SEQ ID NOs:30-34 are representative examples of conservative substitutions in the polypeptide of SEQ ID NO:19 and are encoded by nucleotide sequences of SEQ ID NOs:25-29, respectively.

The nucleotide sequences of SEQ ID NOs:18 and 25-29 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 18 and 25-29 produce the polypeptides of SEQ ID NOs:19 and 30-34. The polypeptides of SEQ ID NOs: 19 and 30-34 are then isolated and/or purified. The isolated and/or purified polypeptides of SEQ ID NOs: 19 and 30-34 are then demonstrated to have activity as alpha-beta hydrolases.

The isolated and/or purified polypeptides of SEQ ID NOs: 19 and 30-34 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 19 and 30-34 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 3

RAAC00568: an Alpha-Glucosidase

Provided in SEQ ID NO:35 is a nucleotide sequence isolated from *Alicyclobacillus acidocaldarius* and encoding the polypeptide of SEQ ID NO:36. As can be seen in FIGS. 3A, 3B, and 3C, SEQ ID NO:36 aligns well with other proteins identified as alpha-glucosidases. Of particular importance, it is noted that where amino acids are conserved in other alpha-glucosidases, those amino acids are generally conserved in SEQ ID NO:36. Thus, the polypeptide provided in SEQ ID NO:36 is properly classified as an alpha-glucosidase.

The polypeptides of SEQ ID NOs:46-50 are representative examples of conservative substitutions in the polypeptide of SEQ ID NO:36 and are encoded by nucleotide sequences of SEQ ID NOs:41-45, respectively.

The nucleotide sequences of SEQ ID NOs:35 and 41-45 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 35 and 41-45 produce the polypeptides of SEQ ID NOs:36 and 46-50. The polypeptides of SEQ ID NOs: 36 and 46-50 are then isolated and/or purified. The isolated and/or purified polypeptides of SEQ ID NOs: 36 and 46-50 are then demonstrated to have activity as alpha-glucosidases.

The isolated and/or purified polypeptides of SEQ ID NOs: 36 and 46-50 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 36 and 46-50 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 4

Production and Purification of RAAC00568: an Alpha-Glucosidase

The nucleotide sequence of SEQ ID NO:35 was cloned from *Alicyclobacillus acidocaldarius*. SEQ ID NO:35 encodes the polypeptide of SEQ ID NO:36. SEQ ID NO:35 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:36 was detected from both transformed *E. coli* and *P. pastoris* comprising SEQ ID NO:35 and RAAC00568 was affinity purified using a cobalt resin from these sources for activity testing.

Example 5

Alpha-Glucosidase Activity of RAAC00568

RAAC00568 purified from *P. pastoris* was tested for alpha-glucosidase activity using an assay summarized as follows:

A stock solution of α-glucopyranoside-p-nitrophenol (Sigma Cat. No N1377) was prepared by adding 90.375 mg to 10 mL of water. This stock was diluted 1:15 in 50 mM sodium acetate buffer at pH 2.0, 3.5, and 5.5.

Samples of purified RAAC00568 generated in Example 4 were diluted 1:5, 1:10; 1:20, and 1:50 in 50 mM sodium acetate buffer pH 2.0, 3.5 and 5.5. Samples (RAAC00568 samples and positive controls) were placed the wells of a 96 well plate in 10 μL aliquots. Blanks of buffer only were placed in some wells. 190 μL of α-glucopyranoside-p-nitrophenol solution, preheated to 60 or 80 degrees Celsius, was then added to each cell and the plate further incubated at 60 or 80 degrees Celsius for an additional 10 minutes. 100 μL of 2M sodium carbonate was then added to each well and the α-glucosidase activity measured in a 96 well plate reader (Molecular Devices UV-Vis) at a wavelength of 405 nm.

Specific activity for RAAC00568 as determined appears in Table 1.

TABLE 1

| ASSAY<br>Alpha-glucosidase: | SPECIFIC ACTIVITY<br>*P. pastoris* |
|---|---|
| pH 3.5, 60° C. | 2.5 μmol/min mg |
| pH 5.5, 60° C. | 1.4 μmol/min mg |
| pH 3.5, 80° C. | 2.8 μmol/min mg |
| pH 2.0, 60° C. | 2.4 μmol/min mg |

Example 6

Alpha-Xylosidase Activity of RAAC00568

RAAC00307 purified from *P. pastoris* was tested for xylosidase activity using a fluorescent assay summarized as follows:

A solution of α-xylopyranoside p-nitrophenol (Sigma Cat. No N1895) was created by diluting 50 mg of α-xylopyranoside p-nitrophenol in 2 mL methanol. Individual aliquots of this solution were then diluted 1:50 with 50 mM sodium acetate buffer of pH 2.0, 3.5 and 5.5

Samples of purified RAAC00568 generated in Example 5 were diluted 1:5, 1:10; 1:20, and 1:50 in 50 mM sodium acetate buffer pH 2.0, 3.5 and 5.5. Samples (RAAC00568 samples and positive controls) were placed the wells of a 96 well plate in 10 μL aliquots. Blanks of buffer only were placed in some wells. 190 μL of α-xylopyranoside solution, preheated to 60 or 80 degrees Celsius, was then added to each cell and the plate further incubated at 60 or 80 degrees Celsius for an additional 10 minutes. 100 μL of 2.0 M sodium carbonate was then added to each well and the α-xylosidase activity measured in a 96 well plate reader (Molecular Devices UV-Vis) at a wavelength of 405 nm.

Specific activity for RAAC00568 as determined appears in Table 2.

TABLE 2

| ASSAY<br>Alpha-xylosidase: | SPECIFIC ACTIVITY<br>*P. pastoris* |
| --- | --- |
| pH 3.5, 60° C. | 2.5 μmol/min mg |
| pH 5.5, 60° C. | 6.2 μmol/min mg |
| pH 3.5, 80° C. | 14 μmol/min mg |
| pH 2.0, 60° C. | 1.36 μmol/min mg |

Example 7

RAAC00594

Provided in SEQ ID NO:51 is a nucleotide sequence isolated from *Alicyclobacillus acidocaldarius* and encoding the polypeptide of SEQ ID NO:52. As can be seen in FIGS. 4A, 4B, and 4C, SEQ ID NO:52 aligns well with other proteins identified as alpha-xylosidases. Of particular importance, it is noted that where amino acids are conserved in other alpha-xylosidases, those amino acids are generally conserved in SEQ ID NO:52.

The polypeptides of SEQ ID NOs:63-67 are representative examples of conservative substitutions in the polypeptide of SEQ ID NO:52 and are encoded by nucleotide sequences of SEQ ID NOs:58-62, respectively.

The nucleotide sequences of SEQ ID NOs:51 and 58-62 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 51 and 58-62 produce the polypeptides of SEQ ID NOs:52 and 63-67. The polypeptides of SEQ ID NOs: 52 and 63-67 are then isolated and/or purified.

Example 8

Production and Purification of RAAC00594

The nucleotide sequence of SEQ ID NO:51 was cloned from *Alicyclobacillus acidocaldarius*. SEQ ID NO:51 encodes the polypeptide of SEQ ID NO:52. SEQ ID NO:51 was cloned into the pBAD/HIS A expression vector for *E. coli* and provided to *E. coli* via electroporation into competent cells, respectively. Expression of SEQ ID NO:52 was detected from both transformed *E. coli* comprising SEQ ID NO:51 and RAAC00594 was affinity purified using a cobalt resin from these sources for activity testing.

Example 9

RAAC00602: an Alpha-L-Arabinofuranosidase

Provided in SEQ ID NO:68 is a nucleotide sequence isolated from *Alicyclobacillus acidocaldarius* and encoding the polypeptide of SEQ ID NO:69. As can be seen in FIGS. 5A and 5B, SEQ ID NO:69 aligns well with other proteins identified as alpha-L-arabinofuranosidases. Of particular importance, it is noted that where amino acids are conserved in other alpha-L-arabinofuranosidases, those amino acids are generally conserved in SEQ ID NO:69. Thus, the polypeptide provided in SEQ ID NO:69 is properly classified as an alpha-L-arabinofuranosidase.

The polypeptides of SEQ ID NOs:80-84 are representative examples of conservative substitutions in the polypeptide of SEQ ID NO:69 and are encoded by nucleotide sequences of SEQ ID NOs:75-79, respectively.

The nucleotide sequences of SEQ ID NOs:68 and 75-79 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 68 and 75-79 produce the polypeptides of SEQ ID NOs:69 and 80-84. The polypeptides of SEQ ID NOs: 69 and 80-84 are then isolated and/or purified. The isolated and/or purified polypeptides of SEQ ID NOs: 69 and 80-84 are then demonstrated to have activity as alpha-L-arabinofuranosidases.

The isolated and/or purified polypeptides of SEQ ID NOs: 69 and 80-84 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 69 and 80-84 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 10

Production and Purification of RAAC00602: an Alpha-L-Arabinofuranosidase

The nucleotide sequence of SEQ ID NO:68 was cloned from *Alicyclobacillus acidocaldarius*. SEQ ID NO:68 encodes the polypeptide of SEQ ID NO:69. SEQ ID NO:68 was cloned into the pBAD/HIS A expression vector for *E. coli* and provided to *E. coli* via electroporation into competent cells, respectively. Expression of SEQ ID NO:69 was detected from both transformed *E. coli* comprising SEQ ID NO:68 and RAAC00602 was affinity purified using a cobalt resin from these sources for activity testing.

Example 11

Alpha-L-Arabinofuranosidase Activity of RAAC00602

RAAC00602 purified from *E. coli* and *P. pastoris* was tested for alpha-L-arabinofuranosidase activity using an assay summarized as follows:

A solution of α-arabinofuranoside p-nitrophenol (Sigma Cat. No. N3641) was created by diluting 271.2 mg of α-arabinofuranoside p-nitrophenol in 10 mL methanol. Individual aliquots of this solution were then diluted 1:50 with 50 mM sodium acetate buffer of pH 2.0 and 3.5.

Samples of purified RAAC00602 generated in Example 10 were diluted 1:5, 1:10; 1:20, and 1:50 in 50 mM sodium acetate buffer pH 2.0 and 3.5. Samples (RAAC00602 samples and positive controls) were placed the wells of a 96 well plate in 10 µL aliquots. Blanks of buffer only were placed in some wells. 190 µL of α-arabinofuranoside p-nitrophenol solution, preheated to 60 or 80 degrees Celsius, was then added to each cell and the plate further incubated at 60 or 80 degrees Celsius for an additional 10 minutes. 100 µL of 2.0 M sodium carbonate was then added to each well and the α-xylosidase activity measured in a 96 well plate reader (Molecular Devices UV-Vis) at a wavelength of 405 nm.

Specific activity for RAAC00692 as determined appears in Table 3.

TABLE 3

| ASSAY α-L-arabinofuranosidase | SPECIFIC ACTIVITY *P. pastoris* | SPECIFIC ACTIVITY *E. coli* |
| --- | --- | --- |
| pH 3.5 60 C. | 5.54 µmol/min mg | 15.2 µmol/min mg |
| pH 2.0 60 C. | 0.1 µmol/min mg | 0.07 µmol/min mg |
| pH 3.5 80 C. | 3.53 µmol/min mg | 9.77 µmol/min mg |
| pH 2.0 80 C. | 1.46 µmol/min mg | 0 µmol/min mg |

Example 12

Beta-Xylosidase Activity of RAAC00602

RAAC00602 purified from *E. coli* and *P. pastoris* was tested for beta-xylosidase activity using a fluorescent assay summarized as follows:

A solution of MUXyl (4-methylumbelliferyl β-D-Xylopyranoside) (Sigma M7008-1G CAS #6734-33-4) was created by diluting 10 mg (0.01 g) MUXyl in 1 mL Dimethyl Sulfoxide (DMSO). Individual aliquots of the DMSO solution were then diluted 1:100 with 50 mM sodium acetate buffer of pH 2.0 and 3.5.

Samples of purified RAAC00602 generated in Example 10 were diluted 1:5, 1:10; 1:20, and 1:50 in 50 mM sodium acetate buffer of pH 2.0 and 3.5. β-xylosidase from *A. niger* (Sigma X3501-5UN-CAS #9025-530) was diluted 1:100 in 50 mM sodium acetate buffer pH 2.0 and 3.5 as positive controls. Samples (RAAC00602 samples and positive controls) were placed the wells of a 96 well plate in 50 µL aliquots. Blanks of buffer only were placed in some wells. The plate as then preheated to 60 or 80 degrees Celsius for 5 minutes. 10 µL of MUXyl solution was then added to each cell and the plate further incubated at 60 or 80 degrees Celsius for an additional 10 minutes. 100 µL of 0.5 M sodium carbonate was then added to each well and the α-xylosidase activity measured in a 96 well plate reader (SpectraMAX Gemini) at Excitation 355 and Emission 460. Specific activity for RAAC00602 as determined appears in Table 4.

TABLE 4

| ASSAY β-xylosidase | SPECIFIC ACTIVITY *P. pastoris* | SPECIFIC ACTIVITY *E. coli* |
| --- | --- | --- |
| pH 3.5 60 C. |  | 2.5 µmol/min mg |
| pH 2.0 60 C. | 1.2 µmol/min mg |  |
| pH 2.0 80 C. | 0.7 µmol/min mg |  |

Example 13

RAAC00798: a Cell Wall-Associated Hydrolase

Provided in SEQ ID NO:85 is a nucleotide sequence isolated from *Alicyclobacillus acidocaldarius* and encoding the polypeptide of SEQ ID NO:86. As can be seen in FIGS. 6A and 6B, SEQ ID NO:86 aligns well with other proteins identified as cell wall-associated hydrolases. Of particular importance, it is noted that where amino acids are conserved in other cell wall-associated hydrolases, those amino acids are generally conserved in SEQ ID NO:86. Thus, the polypeptide provided in SEQ ID NO:86 is properly classified as an cell wall-associated hydrolase.

The polypeptides of SEQ ID NOs:96-100 are representative examples of conservative substitutions in the polypeptide of SEQ ID NO:86 and are encoded by nucleotide sequences of SEQ ID NOs:91-95, respectively.

The nucleotide sequences of SEQ ID NOs:85 and 91-95 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 85 and 91-95 produce the polypeptides of SEQ ID NOs:86 and 96-100. The polypeptides of SEQ ID NOs: 86 and 96-100 are then isolated and/or purified. The isolated and/or purified polypeptides of SEQ ID NOs: 86 and 96-100 are then demonstrated to have activity as cell wall-associated hydrolases.

The isolated and/or purified polypeptides of SEQ ID NOs: 86 and 96-100 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 86 and 96-100 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 14

RAAC01076: an Altronate Hydrolase

Provided in SEQ ID NO:101 is a nucleotide sequence isolated from *Alicyclobacillus acidocaldarius* and encoding the polypeptide of SEQ ID NO: 102. As can be seen in FIGS. 7A and 7B, SEQ ID NO:102 aligns well with other proteins identified as altronate hydrolases. Of particular importance, it is noted that where amino acids are conserved in other altronate hydrolases, those amino acids are generally conserved in SEQ ID NO: 102. Thus, the polypeptide provided in SEQ ID NO: 102 is properly classified as an altronate hydrolase.

The polypeptides of SEQ ID NOs:113-117 are representative examples of conservative substitutions in the polypeptide of SEQ ID NO: 102 and are encoded by nucleotide sequences of SEQ ID NOs:108-112, respectively.

The nucleotide sequences of SEQ ID NOs: 101 and 108-112 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 101 and 108-112 produce the polypeptides of SEQ ID NOs:102 and 113-117. The polypeptides of SEQ ID NOs: 102 and 113-117 are then isolated and/or purified. The isolated and/or purified polypeptides of SEQ ID NOs: 102 and 113-117 are then demonstrated to have activity as altronate hydrolases.

The isolated and/or purified polypeptides of SEQ ID NOs: 102 and 113-117 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 102 and 113-117 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 15

RAAC04341

Provided in SEQ ID NO:118 is a nucleotide sequence isolated from *Alicyclobacillus acidocaldarius* and encoding the polypeptide of SEQ ID NO:119. As can be seen in FIGS. 8A and 8B, SEQ ID NO:119 aligns well with proteins identified as cellulase/endoglucanase Ms. Of particular importance, it is noted that where amino acids are conserved in other cellulase/endoglucanase Ms, those amino acids are generally conserved in SEQ ID NO:119.

The polypeptides of SEQ ID NOs:130-134 are representative examples of conservative substitutions in the polypeptide of SEQ ID NO:119 and are encoded by nucleotide sequences of SEQ ID NOs: 125-129, respectively.

The nucleotide sequences of SEQ ID NOs:118 and 125-129 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 118 and 125-129 produce the polypeptides of SEQ ID NOs:119 and 130-134. The polypeptides of SEQ ID NOs: 119 and 130-134 are then isolated and/or purified.

The isolated and/or purified polypeptides of SEQ ID NOs: 119 and 130-134 are challenged with peptides, polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 119 and 130-134 are demonstrated to have activity in at least partially degrading, cleaving, and/or removing peptides, polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 16

Production and Purification of RAAC04341

The nucleotide sequence of SEQ ID NO:118 was cloned from *Alicyclobacillus acidocaldarius*. SEQ ID NO:118 encodes the polypeptide of SEQ ID NO:119. SEQ ID NO:118 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:119 was detected from both transformed *E. coli* and *P. pastoris* comprising SEQ ID NO:118 and RAAC04341 was affinity purified using a cobalt resin from these sources for activity testing.

Example 17

RAAC04342

Provided in SEQ ID NO:135 is a nucleotide sequence isolated from *Alicyclobacillus acidocaldarius* and encoding the polypeptide of SEQ ID NO:136. As can be seen in FIGS. 9A and 9B, SEQ ID NO:136 aligns well with other proteins identified as cellulase/endoglucanase Ms. Of particular importance, it is noted that where amino acids are conserved in other cellulase/endoglucanase Ms, those amino acids are generally conserved in SEQ ID NO:136.

The polypeptides of SEQ ID NOs:147-151 are representative examples of conservative substitutions in the polypeptide of SEQ ID NO:136 and are encoded by nucleotide sequences of SEQ ID NOs:142-146, respectively.

The nucleotide sequences of SEQ ID NOs:135 and 142-146 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 135 and 142-146 produce the polypeptides of SEQ ID NOs:136 and 147-151. The polypeptides of SEQ ID NOs: 136 and 147-151 are then isolated and/or purified.

The isolated and/or purified polypeptides of SEQ ID NOs: 136 and 147-151 are challenged with peptides, polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 136 and 147-151 are demonstrated to have activity in at least partially degrading, cleaving, and/or removing peptides, polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 18

Production and Purification of RAAC04342

The nucleotide sequence of SEQ ID NO:135 was cloned from *Alicyclobacillus acidocaldarius*. SEQ ID NO:135 encodes the polypeptide of SEQ ID NO:136. SEQ ID NO:135 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:136 was detected from both transformed *E. coli* and *P. pastoris* comprising SEQ ID NO:135 and RAAC04342 was affinity purified using a cobalt resin from these sources for activity testing.

Example 19

RAAC04343: a Cellulase/Endoglucanase M

Provided in SEQ ID NO:152 is a nucleotide sequence isolated from *Alicyclobacillus acidocaldarius* and encoding the polypeptide of SEQ ID NO:153. As can be seen in FIGS. 10A and 10B, SEQ ID NO:153 aligns well with other proteins identified as cellulase/endoglucanase Ms. Of particular importance, it is noted that where amino acids are conserved in other cellulase/endoglucanase Ms, those amino acids are generally conserved in SEQ ID NO:153. Thus, the polypeptide provided in SEQ ID NO:153 is properly classified as a cellulose/endoglucanase M.

The polypeptides of SEQ ID NOs:162-166 are representative examples of conservative substitutions in the polypeptide of SEQ ID NO:153 and are encoded by nucleotide sequences of SEQ ID NOs:157-161, respectively.

The nucleotide sequences of SEQ ID NOs:152 and 157-161 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 152 and 157-161 produce the polypeptides of SEQ ID NOs:153 and 162-166. The polypeptides of SEQ ID NOs: 153 and 162-166 are then isolated and/or purified. The isolated and/or purified polypeptides of SEQ ID NOs: 153 and 162-166 are then demonstrated to have activity as cellulase/endoglucanase Ms.

The isolated and/or purified polypeptides of SEQ ID NOs: 153 and 162-166 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 153 and 162-166 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 20

Production of RAAC04343

The nucleotide sequence of SEQ ID NO:152 was cloned from *Alicyclobacillus acidocaldarius*. SEQ ID NO:152 encodes the polypeptide of SEQ ID NO:153. SEQ ID NO:152 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:153 was detected from both transformed *E. coli* and *P. pastoris* comprising SEQ ID NO:152.

Example 21

RAAC01275: a Polygalacturonase

Provided in SEQ ID NO:167 is a nucleotide sequence isolated from *Alicyclobacillus acidocaldarius* and encoding the polypeptide of SEQ ID NO:168. As can be seen in FIGS. 11A-11C, SEQ ID NO:168 aligns well with other proteins identified as polygalacturonases. Of particular importance, it is noted that where amino acids are conserved in other polygalacturonases, those amino acids are generally conserved in SEQ ID NO:168. Thus, the polypeptide provided in SEQ ID NO:168 is properly classified as a polygalacturonase.

The polypeptides of SEQ ID NOs:179-183 are representative examples of conservative substitutions in the polypeptide of SEQ ID NO:168 and are encoded by nucleotide sequences of SEQ ID NOs: 174-178, respectively.

The nucleotide sequences of SEQ ID NOs:167 and 174-178 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 167 and 174-178 produce the polypeptides of SEQ ID NOs:168 and 179-183. The polypeptides of SEQ ID NOs: 168 and 179-183 are then isolated and/or purified. The isolated and/or purified polypeptides of SEQ ID NOs: 168 and 179-183 are then demonstrated to have activity as polygalacturonases.

The isolated and/or purified polypeptides of SEQ ID NOs: 168 and 179-183 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 168 and 179-183 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 22

RAAC01615: an Alpha-Galactosidase

Provided in SEQ ID NO:184 is a nucleotide sequence isolated from *Alicyclobacillus acidocaldarius* and encoding the polypeptide of SEQ ID NO:185. As can be seen in FIGS. 12A-12C, SEQ ID NO:185 aligns well with other proteins identified as alpha-galactosidase Of particular importance, it is noted that where amino acids are conserved in other alpha-galactosidases, those amino acids are generally conserved in SEQ ID NO:185. Thus, the polypeptide provided in SEQ ID NO:185 is properly classified as a alpha-galactosidase.

The polypeptides of SEQ ID NOs:196-200 are representative examples of conservative substitutions in the polypeptide of SEQ ID NO:185 and are encoded by nucleotide sequences of SEQ ID NOs:191-195, respectively.

The nucleotide sequences of SEQ ID NOs:184 and 191-195 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 184 and 191-195 produce the polypeptides of SEQ ID NOs:185 and 196-200. The polypeptides of SEQ ID NOs: 185 and 196-200 are then isolated and/or purified. The isolated and/or purified polypeptides of SEQ ID NOs: 185 and 196-200 are then demonstrated to have activity as alpha-galactosidases.

The isolated and/or purified polypeptides of SEQ ID NOs: 185 and 196-200 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 185 and 196-200 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 23

RAAC01621: a Cellobiose Phosphorylase

Provided in SEQ ID NO:201 is a nucleotide sequence isolated from *Alicyclobacillus acidocaldarius* and encoding the polypeptide of SEQ ID NO:202. As can be seen in FIGS. 13A-13K, SEQ ID NO:202 aligns well with other proteins identified as cellobiose phosphorylases. Of particular importance, it is noted that where amino acids are conserved in other cellobiose phosphorylases, those amino acids are generally conserved in SEQ ID NO:202. Thus, the polypeptide provided in SEQ ID NO:202 is properly classified as a cellobiose phosphorylase.

The polypeptides of SEQ ID NOs:213-217 are representative examples of conservative substitutions in the polypeptide of SEQ ID NO:202 and are encoded by nucleotide sequences of SEQ ID NOs:208-212, respectively.

The nucleotide sequences of SEQ ID NOs:201 and 208-212 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 201 and 208-212 produce the polypeptides of SEQ ID NOs:202 and 213-217. The polypeptides of SEQ ID NOs: 202 and 213-217 are then isolated and/or purified. The isolated and/or purified polypeptides of SEQ ID NOs: 202 and 213-217 are then demonstrated to have activity as cellobiose phosphorylases.

The isolated and/or purified polypeptides of SEQ ID NOs: 202 and 213-217 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 202 and 213-217 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 24

RAAC01755: an Alpha-Glucosidase

Provided in SEQ ID NO:218 is a nucleotide sequence isolated from *Alicyclobacillus acidocaldarius* and encoding the polypeptide of SEQ ID NO:219. As can be seen in FIGS. 14A-14C, SEQ ID NO:219 aligns well with proteins identified as glycogen debranching enzymes. Of particular importance, it is noted that where amino acids are conserved in other glycogen debranching enzymes, those amino acids are generally conserved in SEQ ID NO:219.

The polypeptides of SEQ ID NOs:230-234 are representative examples of conservative substitutions in the polypeptide of SEQ ID NO:219 and are encoded by nucleotide sequences of SEQ ID NOs:225-229, respectively.

The nucleotide sequences of SEQ ID NOs:218 and 225-229 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 218 and 225-229 produce the polypeptides of SEQ ID NOs:219 and 230-234. The polypeptides of SEQ ID NOs: 219 and 230-234 are then isolated and/or purified. The isolated and/or purified polypeptides of SEQ ID NOs: 219 and 230-234 are then demonstrated to have activity.

The isolated and/or purified polypeptides of SEQ ID NOs: 219 and 230-234 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 219 and 230-234 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 25

Production and Purification of RAAC01755

The nucleotide sequence of SEQ ID NO:218 was cloned from *Alicyclobacillus acidocaldarius*. SEQ ID NO:218 encodes the polypeptide of SEQ ID NO:219. SEQ ID NO:218 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:219 was detected from both transformed *E. coli* and *P. pastoris* comprising SEQ ID NO:218 and RAAC01755 was affinity purified using a cobalt resin from these sources for activity testing.

Example 26

RAAC01887: a Cellulase/Endoglucanase M

Provided in SEQ ID NO:235 is a nucleotide sequence isolated from *Alicyclobacillus acidocaldarius* and encoding the polypeptide of SEQ ID NO:236. As can be seen in FIGS. 15A and 15B, SEQ ID NO:236 aligns well with other proteins identified as cellulase/endoglucanase Ms. Of particular importance, it is noted that where amino acids are conserved in other cellulase/endoglucanase Ms, those amino acids are generally conserved in SEQ ID NO:236. Thus, the polypeptide provided in SEQ ID NO:236 is properly classified as a cellulase/endoglucanase M.

The polypeptides of SEQ ID NOs:247-251 are representative examples of conservative substitutions in the polypeptide of SEQ ID NO:236 and are encoded by nucleotide sequences of SEQ ID NOs:242-246, respectively.

The nucleotide sequences of SEQ ID NOs:235 and 242-246 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 235 and 242-246 produce the polypeptides of SEQ ID NOs:236 and 247-251. The polypeptides of SEQ ID NOs: 236 and 247-251 are then isolated and/or purified. The isolated and/or purified polypeptides of SEQ ID NOs: 236 and 247-251 are then demonstrated to have activity as cellulase/endoglucanase Ms.

The isolated and/or purified polypeptides of SEQ ID NOs: 236 and 247-251 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 236 and 247-251 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 27

Production of RAAC01887

The nucleotide sequence of SEQ ID NO:235 was cloned from *Alicyclobacillus acidocaldarius*. SEQ ID NO:235 encodes the polypeptide of SEQ ID NO:236. SEQ ID NO:235 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:236 was detected from both transformed *E. coli* and *P. pastoris* comprising SEQ ID NO:235.

Example 28

RAAC01897: an Acetyl Esterase/Acetyl Hydrolase

Provided in SEQ ID NO:252 is a nucleotide sequence isolated from *Alicyclobacillus acidocaldarius* and encoding the polypeptide of SEQ ID NO:253. As can be seen in FIGS. 16A and 16B, SEQ ID NO:253 aligns well with other proteins identified as acetyl esterase/acetyl hydrolases. Of particular importance, it is noted that where amino acids are conserved in other acetyl esterase/acetyl hydrolases, those amino acids are generally conserved in SEQ ID NO:253. Thus, the polypeptide provided in SEQ ID NO:253 is properly classified as an acetyl esterase/acetyl hydrolase.

The polypeptides of SEQ ID NOs:264-268 are representative examples of conservative substitutions in the polypeptide of SEQ ID NO:253 and are encoded by nucleotide sequences of SEQ ID NOs:259-263, respectively.

The nucleotide sequences of SEQ ID NOs:252 and 259-263 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 252 and 259-263 produce the polypeptides of SEQ ID NOs:253 and 264-268. The polypeptides of SEQ ID NOs: 253 and 264-268 are then isolated and/or purified. The isolated and/or purified polypeptides of SEQ ID NOs: 253 and 264-268 are then demonstrated to have activity as acetyl esterase/acetyl hydrolases.

The isolated and/or purified polypeptides of SEQ ID NOs: 253 and 264-268 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 253 and 264-268 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 29

RAAC01917: a Beta-1,4-Xylanase

Provided in SEQ ID NO:269 is a nucleotide sequence isolated from *Alicyclobacillus acidocaldarius* and encoding the polypeptide of SEQ ID NO:270. As can be seen in FIGS. 17A and 17B, SEQ ID NO:270 aligns well with other proteins identified as beta-1,4-xylanases. Of particular importance, it is noted that where amino acids are conserved in other beta-1,4-xylanases, those amino acids are generally conserved in SEQ ID NO:270. Thus, the polypeptide provided in SEQ ID NO:270 is properly classified as a beta-1,4-xylanase.

The polypeptides of SEQ ID NOs:281-285 are representative examples of conservative substitutions in the polypeptide of SEQ ID NO:270 and are encoded by nucleotide sequences of SEQ ID NOs:276-280, respectively.

The nucleotide sequences of SEQ ID NOs:269 and 276-280 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 269 and 276-280 produce the polypeptides of SEQ ID NOs:270 and 281-285. The polypeptides of SEQ ID NOs: 270 and 281-285 are then isolated and/or purified. The isolated and/or purified polypeptides of SEQ ID NOs: 270 and 281-285 are then demonstrated to have activity as beta-1,4-xylanases.

The isolated and/or purified polypeptides of SEQ ID NOs: 270 and 281-285 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 270 and 281-285 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 30

Production of RAAC01917

The nucleotide sequence of SEQ ID NO:269 was cloned from *Alicyclobacillus acidocaldarius*. SEQ ID NO:269 encodes the polypeptide of SEQ ID NO:270. SEQ ID NO:269 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:270 was detected from both transformed *E. coli* and *P. pastoris* comprising SEQ ID NO:269.

Example 31

RAAC02404: a Cinnamoyl Ester Hydrolase

Provided in SEQ ID NO:286 is a nucleotide sequence isolated from *Alicyclobacillus acidocaldarius* and encoding the polypeptide of SEQ ID NO:287. As can be seen in FIGS. 18A and 18B, SEQ ID NO:287 aligns well with other proteins identified as cinnamoyl ester hydrolases. Of particular importance, it is noted that where amino acids are conserved in other cinnamoyl ester hydrolases, those amino acids are generally conserved in SEQ ID NO:287. Thus, the polypeptide provided in SEQ ID NO:287 is properly classified as a cinnamoyl ester hydrolase.

The polypeptides of SEQ ID NOs:298-302 are representative examples of conservative substitutions in the polypeptide of SEQ ID NO:287 and are encoded by nucleotide sequences of SEQ ID NOs:293-297, respectively.

The nucleotide sequences of SEQ ID NOs:286 and 293-297 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 286 and 293-297 produce the polypeptides of SEQ ID NOs:287 and 298-302. The polypeptides of SEQ ID NOs: 287 and 298-302 are then isolated and/or purified. The isolated and/or purified polypeptides of SEQ ID NOs: 287 and 298-302 are then demonstrated to have activity as cinnamoyl ester hydrolases.

The isolated and/or purified polypeptides of SEQ ID NOs: 287 and 298-302 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 287 and 298-302 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 32

RAAC02424: a Carboxylesterase Type B

Provided in SEQ ID NO:303 is a nucleotide sequence isolated from *Alicyclobacillus acidocaldarius* and encoding the polypeptide of SEQ ID NO:304. As can be seen in FIGS. 19A and 19B, SEQ ID NO:304 aligns well with other proteins identified as carboxylesterase type Bs. Of particular importance, it is noted that where amino acids are conserved in other carboxylesterase type Bs, those amino acids are generally conserved in SEQ ID NO:304. Thus, the polypeptide provided in SEQ ID NO:304 is properly classified as a carboxylesterase type B.

The polypeptides of SEQ ID NOs:315-319 are representative examples of conservative substitutions in the polypeptide of SEQ ID NO:304 and are encoded by nucleotide sequences of SEQ ID NOs:310-314, respectively.

The nucleotide sequences of SEQ ID NOs:303 and 310-314 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 303 and 310-314 produce the polypeptides of SEQ ID NOs:304 and 315-319. The polypeptides of SEQ ID NOs: 304 and 315-319 are then isolated and/or purified. The isolated and/or purified polypeptides of SEQ ID NOs: 304 and 315-319 are then demonstrated to have activity as carboxylesterase type Bs.

The isolated and/or purified polypeptides of SEQ ID NOs: 304 and 315-319 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 304 and 315-319 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 33

Production and Purification of RAAC02424

The nucleotide sequence of SEQ ID NO:303 was cloned from *Alicyclobacillus acidocaldarius*. SEQ ID NO:303 encodes the polypeptide of SEQ ID NO:304. SEQ ID NO:303 was cloned into the pBAD/HIS A expression vector for *E. coli* and provided to *E. coli* via electroporation into competent cells, respectively. Expression of SEQ ID NO:304 was detected from both transformed *E. coli* comprising SEQ ID NO:303 and RAAC002424 was affinity purified using a cobalt resin from these sources for activity testing.

Example 34

RAAC02616: a Beta Galactosidase/Beta-Glucuronidase

Provided in SEQ ID NO:320 is a nucleotide sequence isolated from *Alicyclobacillus acidocaldarius* and encoding the polypeptide of SEQ ID NO:321. As can be seen in FIGS. 20A-20D, SEQ ID NO:321 aligns well with other proteins identified as beta galactosidase/beta-glucuronidases. Of particular importance, it is noted that where amino acids are conserved in other beta galactosidase/beta-glucuronidases, those amino acids are generally conserved in SEQ ID NO:321. Thus, the polypeptide provided in SEQ ID NO:321 is properly classified as a beta galactosidase/beta-glucuronidase.

The polypeptides of SEQ ID NOs:331-335 are representative examples of conservative substitutions in the polypeptide of SEQ ID NO:321 and are encoded by nucleotide sequences of SEQ ID NOs:326-330, respectively.

The nucleotide sequences of SEQ ID NOs:320 and 326-330 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 320 and 326-330 produce the polypeptides of SEQ ID NOs:321 and 331-335. The polypeptides of SEQ ID NOs: 321 and 331-335 are then isolated and/or purified. The isolated and/or purified polypeptides of SEQ ID NOs: 321 and 331-335 are then demonstrated to have activity as beta galactosidase/beta-glucuronidases.

The isolated and/or purified polypeptides of SEQ ID NOs: 321 and 331-335 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 321 and 331-335 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 35

RAAC02661: a Xylan Alpha-1,2-Glucuronidase

Provided in SEQ ID NO:336 is a nucleotide sequence isolated from *Alicyclobacillus acidocaldarius* and encoding the polypeptide of SEQ ID NO:337. As can be seen in FIGS. 21A-21D, SEQ ID NO:337 aligns well with other proteins identified as xylan alpha-1,2-glucuronidases. Of particular importance, it is noted that where amino acids are conserved in other xylan alpha-1,2-glucuronidases, those amino acids are generally conserved in SEQ ID NO:337. Thus, the polypeptide provided in SEQ ID NO:337 is properly classified as a xylan alpha-1,2-glucuronidase.

The polypeptides of SEQ ID NOs:348-352 are representative examples of conservative substitutions in the polypeptide of SEQ ID NO:337 and are encoded by nucleotide sequences of SEQ ID NOs:343-347, respectively.

The nucleotide sequences of SEQ ID NOs:336 and 343-347 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 336 and 343-347 produce the polypeptides of SEQ ID NOs:337 and 348-352. The polypeptides of SEQ ID NOs: 337 and 348-352 are then isolated and/or purified. The isolated and/or purified polypeptides of SEQ ID NOs: 337 and 348-352 are then demonstrated to have activity as xylan alpha-1,2-glucuronidases.

The isolated and/or purified polypeptides of SEQ ID NOs: 337 and 348-352 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 337 and 348-352 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 36

RAAC02925: a 3-Hydroxyisobutyryl-CoA Hydrolase

Provided in SEQ ID NO:353 is a nucleotide sequence isolated from *Alicyclobacillus acidocaldarius* and encoding the polypeptide of SEQ ID NO:354. As can be seen in FIGS. 22A-22C, SEQ ID NO:354 aligns well with other proteins identified as 3-hydroxyisobutyryl-CoA hydrolases. Of particular importance, it is noted that where amino acids are conserved in other 3-hydroxyisobutyryl-CoA hydrolases, those amino acids are generally conserved in SEQ ID NO:354. Thus, the polypeptide provided in SEQ ID NO:354 is properly classified as a 3-hydroxyisobutyryl-CoA hydrolase.

The polypeptides of SEQ ID NOs:365-369 are representative examples of conservative substitutions in the polypeptide of SEQ ID NO:354 and are encoded by nucleotide sequences of SEQ ID NOs:360-364, respectively.

The nucleotide sequences of SEQ ID NOs:353 and 360-364 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 353 and 360-364 produce the polypeptides of SEQ ID NOs:354 and 365-369. The polypeptides of SEQ ID NOs: 354 and 365-369 are then isolated and/or purified. The isolated and/or purified polypeptides of SEQ ID NOs: 354 and 365-369 are then demonstrated to have activity as 3-hydroxyisobutyryl-CoA hydrolases.

The isolated and/or purified polypeptides of SEQ ID NOs: 354 and 365-369 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 354 and 365-369 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 37

RAAC03001: a Beta-Glucosidase

Provided in SEQ ID NO:370 is a nucleotide sequence isolated from *Alicyclobacillus acidocaldarius* and encoding the polypeptide of SEQ ID NO:371. As can be seen in FIGS. 23A-23D, SEQ ID NO:371 aligns well with other proteins identified as beta-glucosidases. Of particular importance, it is noted that where amino acids are conserved in other beta-glucosidases, those amino acids are generally conserved in SEQ ID NO:371. Thus, the polypeptide provided in SEQ ID NO:371 is properly classified as a beta-glucosidase.

The polypeptides of SEQ ID NOs:382-386 are representative examples of conservative substitutions in the polypeptide of SEQ ID NO:371 and are encoded by nucleotide sequences of SEQ ID NOs:377-381, respectively.

The nucleotide sequences of SEQ ID NOs:370 and 377-381 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 370 and 377-381 produce the polypeptides of SEQ ID NOs:371 and 382-386. The polypeptides of SEQ ID NOs: 371 and 382-386 are then isolated and/or purified. The isolated and/or purified polypeptides of SEQ ID NOs: 371 and 382-386 are then demonstrated to have activity as beta-glucosidases.

The isolated and/or purified polypeptides of SEQ ID NOs: 371 and 382-386 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs: 371 and 382-386 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 38

Production and Purification of RAAC03001: a Beta-Glucosidase

The nucleotide sequence of SEQ ID NO:370 was cloned from *Alicyclobacillus acidocaldarius*. SEQ ID NO:370 encodes the polypeptide of SEQ ID NO:371. SEQ ID NO:370 was cloned into the pBAD/HIS A expression vector for *E. coli* and the pPIC6α A expression vector for *P. pastoris* and provided to *E. coli* and *P. pastoris* via electroporation and heat shock into competent cells, respectively. Expression of SEQ ID NO:370 was detected from both transformed *E. coli* and *P. pastoris* comprising SEQ ID NO:370 and RAAC03001 was affinity purified using a cobalt resin from these sources for activity testing.

Example 39

Beta-Glucosidase Activity of RAAC03001

RAAC03001 purified from both *E. coli* was tested for beta-glucosidase activity using the assay summarized as follows: A solution of β-glucopyranoside p-nitrophenol (Sigma Cat. No. N7006) was created by diluting 301.25 mg of p-glucopyranoside p-nitrophenol in 20 mL water. Individual aliquots of this solution were then diluted 1:25 with 50 mM sodium acetate buffer of pH 2.0, 3.5, and 5.5.

Samples of purified RAAC03001 generated in Example 39 were diluted 1:5, 1:10; 1:20, and 1:50 in 50 mM sodium acetate buffer pH 2.0, 3.5, and 5.5. Samples (RAAC03001 samples and positive controls) were placed the wells of a 96 well plate in 10 μL aliquots. Blanks of buffer only were placed in some wells. 190 μL of β-glucopyranoside p-nitrophenol solution, preheated to 60 or 80 degrees Celsius, was then added to each cell and the plate further incubated at 60 or 80 degrees Celsius for an additional 10 minutes. 100 μL of 2.0 M sodium carbonate was then added to each well and the α-xylosidase activity measured in a 96 well plate reader (Molecular Devices UV-Vis) at a wavelength of 405 nm.

The above assay demonstrated that RAAC03001 protein isolated from *E. coli* had beta-glucosidase activity at pHs of 3.5 and 5.5 and a temperature of 60 degrees Celsius; and the RAAC03001 protein isolated from *P. pastoris* had beta-glucosidase activity at pH 5.5 and 60 degrees Celsius.

Example 40

RAAC02913: a Chitooligosaccharide Deacetylase

Provided in SEQ ID NO:387 is a nucleotide sequence isolated from *Alicyclobacillus acidocaldarius* and encoding the polypeptide of SEQ ID NO:388. As can be seen in FIGS. 24A and 24B, SEQ ID NO:388 aligns well with other proteins identified as chitooligosaccharide deacetylases. Of particular importance, it is noted that where amino acids are conserved in other chitooligosaccharide deacetylases, those amino acids are generally conserved in SEQ ID NO:388. Thus, the polypeptide provided in SEQ ID NO:388 is properly classified as a chitooligosaccharide deacetylase.

The polypeptides of SEQ ID NOs:399-403 are representative examples of conservative substitutions in the polypeptide of SEQ ID NO:388 and are encoded by nucleotide sequences of SEQ ID NOs:394-398, respectively.

The nucleotide sequences of SEQ ID NOs:387 and 394-398 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 387 and 394-398 produce the polypeptides of SEQ ID NOs:388 and 399-403. The polypeptides of SEQ ID NOs: 388 and 399-403 are then isolated and/or purified. The isolated and/or purified polypeptides of SEQ ID NOs: 388 and 399-403 are then demonstrated to have activity as chitooligosaccharide deacetylases.

The isolated and/or purified polypeptides of SEQ ID NOs: 388 and 399-403 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 388 and 399-403 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 41

RAAC02839: a Chitooligosaccharide Deacetylase

Provided in SEQ ID NO:404 is a nucleotide sequence isolated from *Alicyclobacillus acidocaldarius* and encoding the polypeptide of SEQ ID NO:405. As can be seen in FIGS. 25A and 25B, SEQ ID NO:405 aligns well with other proteins identified as chitooligosaccharide deacetylases. Of particular importance, it is noted that where amino acids are conserved in other chitooligosaccharide deacetylases, those amino acids are generally conserved in SEQ ID NO:405. Thus, the polypeptide provided in SEQ ID NO:405 is properly classified as a chitooligosaccharide deacetylase.

The polypeptides of SEQ ID NOs:416-420 are representative examples of conservative substitutions in the polypeptide of SEQ ID NO:405 and are encoded by nucleotide sequences of SEQ ID NOs:411-415, respectively.

The nucleotide sequences of SEQ ID NOs:404 and 411-415 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 404 and 411-415 produce the polypeptides of SEQ ID NOs:405 and 416-420. The polypeptides of SEQ ID NOs: 405 and 416-420 are then isolated and/or purified. The isolated and/or purified polypeptides of SEQ ID NOs: 405 and 416-420 are then demonstrated to have activity as chitooligosaccharide deacetylases.

The isolated and/or purified polypeptides of SEQ ID NOs: 405 and 416-420 are challenged with polysaccharides, lignocellulose, cellulose, hernicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 405 and 416-420 are demonstrated to have activity in at least partially degrading, cleaving, and/or removing polysaccharides, lignocellulose, cellulose, hernicellulose, lignin, starch, chitin, polyhydroxybutyrate, heteroxylans, glycosides, xylan-, glucan-, galactan, and/or mannan-decorating groups.

Example 42

RAAC00961: a Chitooligosaccharide Deacetylase

Provided in SEQ ID NO:421 is a nucleotide sequence isolated from *Alicyclobacillus acidocaldarius* and encoding the polypeptide of SEQ ID NO:422. As can be seen in FIGS. 26A-26C, SEQ ID NO:422 aligns well with other proteins identified as chitooligosaccharide deacetylases. Of particular importance, it is noted that where amino acids are conserved in other chitooligosaccharide deacetylases, those amino acids are generally conserved in SEQ ID NO:422. Thus, the polypeptide provided in SEQ ID NO:422 is properly classified as a chitooligosaccharide deacetylase.

The polypeptides of SEQ ID NOs:433-437 are representative examples of conservative substitutions in the polypeptide of SEQ ID NO:422 and are encoded by nucleotide sequences of SEQ ID NOs:428-432, respectively.

The nucleotide sequences of SEQ ID NOs:421 and 428-432 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 421 and 428-432 produce the polypeptides of SEQ ID NOs:422 and 433-437. The polypeptides of SEQ ID NOs: 422 and 433-437 are then isolated and/or purified. The isolated and/or purified polypeptides of SEQ ID NOs: 422 and 433-437 are then demonstrated to have activity as chitooligosaccharide deacetylases.

The isolated and/or purified polypeptides of SEQ ID NOs: 422 and 433-437 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 422 and 433-437 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 43

RAAC00361: a Chitooligosaccharide Deacetylase

Provided in SEQ ID NO:438 is a nucleotide sequence isolated from *Alicyclobacillus acidocaldarius* and encoding the polypeptide of SEQ ID NO:439. As can be seen in FIGS. 27A and 27B, SEQ ID NO:439 aligns well with other proteins identified as chitooligosaccharide deacetylases. Of particular importance, it is noted that where amino acids are conserved in other chitooligosaccharide deacetylases, those amino acids are generally conserved in SEQ ID NO:439. Thus, the polypeptide provided in SEQ ID NO:439 is properly classified as a chitooligosaccharide deacetylase.

The polypeptides of SEQ ID NOs:450-454 are representative examples of conservative substitutions in the polypeptide of SEQ ID NO:439 and are encoded by nucleotide sequences of SEQ ID NOs:445-449, respectively.

The nucleotide sequences of SEQ ID NOs:438 and 445-449 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOs: 438 and 445-449 produce the polypeptides of SEQ ID NOs:439 and 450-454. The polypeptides of SEQ ID NOs: 439 and 450-454 are then isolated and/or purified. The isolated and/or purified polypeptides of SEQ ID NOs: 439 and 450-454 are then demonstrated to have activity as chitooligosaccharide deacetylases.

The isolated and/or purified polypeptides of SEQ ID NOs: 439 and 450-454 are challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NOs: 439 and 450-454 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 44

RAAC00569: a Glucan 1,4-Alpha-Maltohydrolase

Provided in SEQ ID NO:455 is a nucleotide sequence isolated from *Alicyclobacillus acidocaldarius* and encoding the polypeptide of SEQ ID NO:456. SEQ ID NO:456 aligns at about 99% identity with gi:6686566, a glucan 1,4-alpha-maltohydrolase. Thus, the polypeptide provided in SEQ ID NO:456 is properly classified as a glucan 1,4-alpha-maltohydrolase.

The nucleotide sequences of SEQ ID NOs:455 is placed into an expression vector using techniques standard in the art. The vector is then provided to cells such as bacteria cells or eukaryotic cells such as Sf9 cells or CHO cells. In conjunction with the normal machinery in present in the cells, the vector comprising SEQ ID NOs: 455 produces the polypeptide of SEQ ID NO:456. The polypeptides of SEQ ID NO:456 is then isolated and/or purified. The isolated and/or purified polypeptides of SEQ ID NO:456 is then demonstrated to have activity as glucan 1,4-alpha-maltohydrolase.

The isolated and/or purified polypeptide of SEQ ID NOs: 456 is then challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NO:456 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 45

RAAC00574: a Glycosidase

Provided in SEQ ID NO:457 is a nucleotide sequence isolated from *Alicyclobacillus acidocaldarius* and encoding the polypeptide of SEQ ID NO:458. SEQ ID NO:458 aligns at about 99% identity with gi:39301, a glycosidase. Thus, the polypeptide provided in SEQ ID NO:458 is properly classified as a glycosidase.

The nucleotide sequences of SEQ ID NOs:457 is placed into an expression vector using techniques standard in the art. The vector is then provided to cells such as bacteria cells or eukaryotic cells such as Sf9 cells or CHO cells. In conjunction with the normal machinery in present in the cells, the vector comprising SEQ ID NOs: 457 produces the polypeptide of SEQ ID NO:458. The polypeptides of SEQ ID NO:458 is then isolated and/or purified. The isolated and/or purified polypeptides of SEQ ID NO:458 is then demonstrated to have activity as glycosidase.

The isolated and/or purified polypeptide of SEQ ID NOs: 458 is then challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NO:458 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 46

RAAC00575: an Acetyl Esterase

Provided in SEQ ID NO:459 is a nucleotide sequence isolated from *Alicyclobacillus acidocaldarius* and encoding the polypeptide of SEQ ID NO:460. SEQ ID NO:460 aligns at about 95% identity with gi:151567607, a acetyl esterase. Thus, the polypeptide provided in SEQ ID NO:460 is properly classified as a acetyl esterase.

The nucleotide sequences of SEQ ID NOs:459 is placed into an expression vector using techniques standard in the art. The vector is then provided to cells such as bacteria cells or eukaryotic cells such as Sf9 cells or CHO cells. In conjunction with the normal machinery in present in the cells, the vector comprising SEQ ID NOs: 459 produces the polypeptide of SEQ ID NO:460. The polypeptides of SEQ ID NO:460 is then isolated and/or purified. The isolated and/or purified polypeptides of SEQ ID NO:460 is then demonstrated to have activity as acetyl esterase.

The isolated and/or purified polypeptide of SEQ ID NOs: 460 is then challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NO:460 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 47

RAAC01618: a Endo-Beta-1,4-Mannanase

Provided in SEQ ID NO:461 is a nucleotide sequence isolated from *Alicyclobacillus acidocaldarius* and encoding the polypeptide of SEQ ID NO:462. SEQ ID NO:462 aligns at about 92% identity with gi:110611196, a endo-beta-1,4-mannanase. Thus, the polypeptide provided in SEQ ID NO:462 is properly classified as a endo-beta-1,4-mannanase.

The nucleotide sequences of SEQ ID NOs:461 is placed into an expression vector using techniques standard in the art. The vector is then provided to cells such as bacteria cells or eukaryotic cells such as Sf9 cells or CHO cells. In conjunction with the normal machinery in present in the cells, the vector comprising SEQ ID NOs: 461 produces the polypeptide of SEQ ID NO:462. The polypeptides of SEQ ID NO:462 is then isolated and/or purified. The isolated and/or purified polypeptides of SEQ ID NO:462 is then demonstrated to have activity as endo-beta-1,4-mannanase.

The isolated and/or purified polypeptide of SEQ ID NOs: 462 is then challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NO:462 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

Example 48

RAAC01994: a Beta-Glucosidase

Provided in SEQ ID NO:463 is a nucleotide sequence isolated from *Alicyclobacillus acidocaldarius* and encoding the polypeptide of SEQ ID NO:464. SEQ ID NO:464 aligns at about 92% identity with gi:110611196, a beta-glucosidase. Thus, the polypeptide provided in SEQ ID NO:464 is properly classified as a beta-glucosidase.

The nucleotide sequences of SEQ ID NOs:463 is placed into an expression vector using techniques standard in the art. The vector is then provided to cells such as bacteria cells or eukaryotic cells such as Sf9 cells or CHO cells. In conjunction with the normal machinery in present in the cells, the vector comprising SEQ ID NOs: 463 produces the polypeptide of SEQ ID NO:464. The polypeptides of SEQ ID NO:464 is then isolated and/or purified. The isolated and/or purified polypeptides of SEQ ID NO:464 is then demonstrated to have activity as beta-glucosidase.

The isolated and/or purified polypeptide of SEQ ID NOs: 464 is then challenged with polysaccharides, lignocellulose, cellulose, hemicellulose, lignin, starch, chitin, polyhydroxybutyrate, heteroxylans, glycosides, xylan-, glucan-, galactan, and/or mannan-decorating groups. The isolated and/or purified polypeptides of SEQ ID NO:464 is demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan, and/or mannan-decorating groups.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims and their legal equivalents.

BIBLIOGRAPHIC REFERENCES

Barany, F., 1911, PNAS. USA, 88:189-193.
Bertoldo et al., 2004, Eng. Life Sci., 4, No. 6
Buckholz, R. G., 1993, Yeast systems for the expression of heterologous gene products. Curr. Op. Biotechnology 4: 538-542.
Burg, J. L. et al., 1996, Mol. and Cell. Probes, 10: 257-271.

Chu, B. C. F. et al., 1986, NAR, 14: 5591-5603.
Duck, P. et al., 1990, Biotechniques, 9: 142-147.
Edwards, C. P., and Aruffo, A., 1993, Current applications of COS cell based transient expression systems. Curr. Op. Biotechnology 4: 558-563.
Garrote, G, H Dominguez, and J C Parajo, 2001, Manufacture of xylose-based fermentation media from corncobs by posthydrolysis of autohydrolysis liquors, *Appl. Biochem. Biotechnol.*, 95:195-207.
Guateli, J. C. et al., 1990, PNAS. USA, 87: 1874-1878.
Hamelinck, C N, G van Hooijdonk, and A P C Faaij, 2005, Ethanol from lignocellulosic biomass: techno-economic performance in short-, middle-, and long-term, *Biomass Bioenergy*, 28:384-410.
Houben-Weyl, 1974, in Methode der Organischen Chemie, E. Wunsch Ed., Volume 15-I and 15-II, Thieme, Stuttgart.
Huygen, K. et al., 1996, Nature Medicine, 2(8): 893-898.
Innis, M. A. et al., 1990, in PCR Protocols. A guide to Methods and Applications, San Diego, Academic Press.
Jeffries, 1996, Curr. Op. in Biotech., 7:337-342.
Kievitis, T. et al., 1991, J. Virol. Methods, 35: 273-286.
Kohler, G. et al., 1975, Nature, 256(5517): 495497.
Kwoh, D. Y. et al., 1989, PNAS. USA, 86:1173-1177.
Liu C, and C E Wyman, 2003, The effect of flow rate of compressed hot water on xylan, lignin, and total mass removal from corn stover, Ind. Eng. Chem. Res., 42:5409-5416.
Luckow, V. A., 1993, Baculovirus systems for the expression of human gene products. Curr. Op. Biotechnology 4: 564-572.
Lynd et al., 2002, Micro. and Mol. Biol. Rev., Vol. 66, No. 3, P. 506-577.
Malherbe and Cloete, 2002, Re/View in Environmental Science and Bio/Technology, 1: 105-114.
Matthews, J. A. et al., 1988, Anal. Biochem., 169: 1-25.
Merrifield, R. D., 1966, J. Am. Chem. Soc., 88(21): 5051-5052.
Miele, E. A. et al., 1983, J. Mol. Biol., 171: 281-295.
Mielenz, 2001, Curr. Op. in Micro., 4:324-329.
Olins, P. O., and Lee, S. C., 1993, Recent advances in heterologous gene expression in *E. coli*. Curr. Op. Biotechnology 4: 520-525.
Rolfs, A. et al., 1991, In PCR Topics. Usage of Polymerase Chain reaction in Genetic and Infectious Disease. Berlin: Springer-Verlag.
Sambrook, J. et al., 1989, In Molecular cloning: A Laboratory Manual. Cold Spring Harbor, N.Y.: Cold Spring Harbor Laboratory Press.
Sanchez-Pescador, R., 1988, J. Clin. Microbiol., 26(10): 1934-1938.
Segev D., 1992, in "Non-radioactive Labeling and Detection of Biomolecules". Kessler C. Springer Verlag, Berlin, New-York: 197-205.
Shallom and Shoham, 2003, Curr. Op, in Micro., 6:219-228.
Tsao, G T, M R Ladisch, and H R Bungay, 1987. Biomass Refining, In *Advanced Biochemical Engineering*, Wiley Interscience, N.Y., 79-101.
Urdea, M. S., 1988, Nucleic Acids Research, II: 4937-4957.
Vieille and Zeikus, 2001, Micro. and Mol. Biol. Rev., Vol. 65, No. 1, P. 1-43.
Walker, G. T. et al., 1992, NAR 20: 1691-1696.
Walker, G. T. et al., 1992, PNAS. USA, 89: 392-396.
White, B. A. et al., 1997, Methods in Molecular Biology, 67, Humana Press, Totowa, N.J.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07858353B2). An electronic copy of the "Sequence Listing" will also be available from the USPTO upon request and payment of the fee set forth in 37 CFR 1.19(b)(3).

What is claimed is:

1. An isolated or purified nucleic acid sequence comprising a nucleic acid sequence encoding a polypeptide having at least 90% sequence identity to the polypeptide of SEQ ID No. 69 and wherein the polypeptide exhibits Alpha-L-Arabinofuranosidase activity.

2. The isolated or purified nucleic acid sequence of claim 1, wherein the encoded polypeptide has enzymatic activity at or below about pH 7.

3. The isolated or purified nucleic acid sequence of claim 1, wherein the encoded polypeptide has enzymatic activity at a temperature at or above about 50 degrees Celsius.

4. The isolated or purified nucleic acid sequence of claim 1, wherein the nucleic acid sequence is present in a vector.

5. The isolated or purified nucleic acid sequence of claim 1, wherein the nucleic acid sequence comprises a nucleotide sequence having at least 90% identity to SEQ ID No. 68.

6. An isolated or purified nucleic acid sequence comprising a nucleic acid sequence encoding a polypeptide having at least 95% sequence identity to the polypeptide of SEQ ID No. 69 and wherein the polypeptide exhibits Alpha-L-Arabinofuranosidase activity.

7. A method of at least partially degrading, cleaving, or removing polysaccharides, lignocellulose, cellulose, hemicellulose, lignin, starch, chitin, polyhydroxybutyrate, heteroxylans, glycosides, xylan-, glucan-, galactan-, or mannan-decorating groups, the method comprising:
translating the nucleic acid of claim 1 to produce a polypeptide having at least 90% sequence identity to SEQ ID No. 69, and placing the polypeptide in fluid contact with a polysaccharide, lignocellulose, cellulose, hemicellulose, lignin, starch, chitin, polyhydroxybutyrate, heteroxylans, glycoside, xylan-, glucan-, galactan-, or mannan-decorating group.

8. The method according to claim 7, wherein placing the polypeptide in fluid contact with a polysaccharide, lignocellulose, cellulose, hemicellulose, lignin, starch, chitin, polyhydroxybutyrate, heteroxylans, glycoside, xylan-, glucan-, galactan-, or mannan-decorating group occurs at or below about pH 4.

9. The method according to claim 7, wherein placing the polypeptide in fluid contact with a polysaccharide, lignocellulose, cellulose, hemicellulose, lignin, starch, chitin, polyhydroxybutyrate, heteroxylans, glycoside, xylan-, glucan-, galactan-, or mannan-decorating group occurs at a temperature at or above 50 degrees Celsius.

10. The method according to claim 7, wherein the polypeptide is glycosylated, pegylated, or otherwise posttranslationally modified.

* * * * *

UNITED STATES PATENT AND TRADEMARK OFFICE
CERTIFICATE OF CORRECTION

PATENT NO. : 7,858,353 B2  Page 1 of 1
APPLICATION NO. : 12/322359
DATED : December 28, 2010
INVENTOR(S) : David N. Thompson et al.

It is certified that error appears in the above-identified patent and that said Letters Patent is hereby corrected as shown below:

On the title page:
In ITEM (56) References Cited
OTHER PUBLICATIONS
Page 2, 1st column, after the 9th entry
Create new entry (line 28),   --Pearson and Lipman, Proc. Natl. Acad. Sci. (U.S.A.) 85: 2444 (1988).--

Page 2, 1st column, after the 9th entry
Create new entry (line 28),   --Sanchez-Pescador, R., 1988, J. Clin. Microbiol., 26(10): 1934-1938.--

Signed and Sealed this
Twenty-seventh Day of August, 2013

Teresa Stanek Rea
*Acting Director of the United States Patent and Trademark Office*